(12) United States Patent
Dziegiel et al.

(10) Patent No.: US 7,811,569 B2
(45) Date of Patent: Oct. 12, 2010

(54) **RECOMBINANT ANTI-*PLASMODIUM FALCIPARUM* ANTIBODIES**

(75) Inventors: Morten Steen Hanefeld Dziegiel, Roskilde (DK); Rasmus Lundquist, Copenhagen (DK); Leif Kofoed Nielsen, Ishoj (DK); Pierre Druilhe, Paris (FR)

(73) Assignee: Institut Pasteur, Paris (FR)

( * ) Notice: Subject to any disclaimer, the term of this patent is extended or adjusted under 35 U.S.C. 154(b) by 1286 days.

(21) Appl. No.: 10/486,703

(22) PCT Filed: Aug. 16, 2002

(86) PCT No.: PCT/IB02/03995

§ 371 (c)(1),
(2), (4) Date: Aug. 23, 2004

(87) PCT Pub. No.: WO03/016354

PCT Pub. Date: Feb. 27, 2003

(65) Prior Publication Data

US 2005/0004346 A1 Jan. 6, 2005

(30) Foreign Application Priority Data

Aug. 16, 2001 (GB) .................................. 0120057.5

(51) Int. Cl.
*A61K 39/395* (2006.01)
*A61K 39/00* (2006.01)
(52) U.S. Cl. .............. 424/151.1; 424/130.1; 424/133.1; 424/139.1; 424/141.1
(58) Field of Classification Search .................. None
See application file for complete search history.

(56) References Cited

U.S. PATENT DOCUMENTS

| 4,897,354 | A | | 1/1990 | Siddiqui | |
|---|---|---|---|---|---|
| 6,017,538 | A | * | 1/2000 | Druilhe et al. | ........... 424/191.1 |
| 6,114,598 | A | | 9/2000 | Kucherlapati et al. | |
| 6,949,627 | B2 | * | 9/2005 | Druilhe et al. | ........... 530/387.1 |

FOREIGN PATENT DOCUMENTS

| WO | WO 9211383 | * | 7/1992 |
|---|---|---|---|
| WO | WO 9605229 | * | 2/1996 |
| WO | WO 96/37234 | | 11/1996 |
| WO | WO 0012562 A1 | * | 3/2000 |
| WO | WO 00/20460 | | 4/2000 |
| WO | WO01/36587 | | 5/2001 |

OTHER PUBLICATIONS

Badell Edgar et al: "Human malaria in immunocompromised mice: An in vivo model to study defense mechanisms against *Plasmodium falciparum*." Journal of Experimental Medicine, vol. 192, No. 11, Dec. 4, 2000, pp. 1653-1659.*
Paul, William E. Fundamental Immunology, 3rd Edition, 1993, Raven Press, New York, pp. 292-295.*
Rudikoff et al. Proc. Natl. Acad. Sci. USA 1982 vol. 79: p. 1979-1983.*
Abbas et al. Cellular and Molecular Immunology 4th edition, 2000, p. 42-43, 48, 55 and 477.*
Goni et al. J. Immunology 142:3158-3163, 1989.*
Sequence alignment—7 pages.*
Bendig et al Methods: A companion to Methods in Enzymology vol. 8 pp. 83, 85, 87,89,91 and 93 (1995).*
Badell, E. et al., "Human Malaria in Immunocompromised Mice: An In Vivo Model to Study Defense Mechanisms Against *Plasmodium falciparum*", Journal of Experimental Medicine, vol. 192, No. 11, pp. 1653-1659, (Dec. 4, 2000).
Oeuvray, C. et al., "A Novel Merozoite Surface Antigen of *Plasmodium falciparum* (MSP-3) Identified by Cellular-Antibody Cooperative Mechanism Antigenicity and Biological Activity of Antibodies", Memorias Do Instituto Oswaldo Cruz, Rio De Janeiro, BR, vol. 89, No. Supp. II, pp. 77-80, (1994).
Oeuvray, C. et al., "Merozoite Surface Protein-3: A Malaria Protein Inducing Antibodies That Promote *Plasmodium falciparum* Killing by Cooperation With Blood Monocytes", Blood, vol. 84, No. 5, pp. 1594-1602, (Sep. 1, 1994).
De Haard, H. J. et al., "A Large Non-Immunized Human Fab Fragment Phage Library That Permits Rapid Isolation and Kinetic Analysis of High Affinity Antibodies", Journal of Biological Chemistry, American Society of Biological Chemists, vol. 274, No. 26, pp. 18218-18230, (Jun. 25, 1999).
Roeffen, W. F. G. et al., "Recombinant Human Antibodies Specific for the Pfs48/45 Protein of the Malaria Parasite *Plasmodium falciparum*", Journal of Biological Chemistry, vol. 276, No. 23, pp. 19807-19811, (Jun. 8, 2001).
Dziegiel et al., "Recombinant human antibodies against the Plasmodium falciparum glutamate rich protein," Immunotechnology vol. 2(4), 1996, p. 299.
Sylvester et al., "Construction and in vitro characterization of a humanized monoclonal antibody against Plasmodium falciparum sporozoites," J. Cell. Biol. (Suppl.) 18D, 1994.

* cited by examiner

Primary Examiner—Robert Mondesi
Assistant Examiner—Oluwatosin Ogunbiyi
(74) *Attorney, Agent, or Firm*—Finnegan, Henderson Farabow, Garrett & Dunner LLP

(57) ABSTRACT

The present invention relates to a recombinant human antibody comprising an antibodysequence specific for the MSP-3 antigen of *Plasmodium falciparum*. In particular, the invention relates to a recombinant human antibody which is specific for the MSP-$3_{194-257}$ antigen. The invention further relates to nucleic acid encoding such antibodies and to uses of these antibodies, in particular in the treatment or prophylaxis of malaria.

27 Claims, 20 Drawing Sheets

Figure 1:
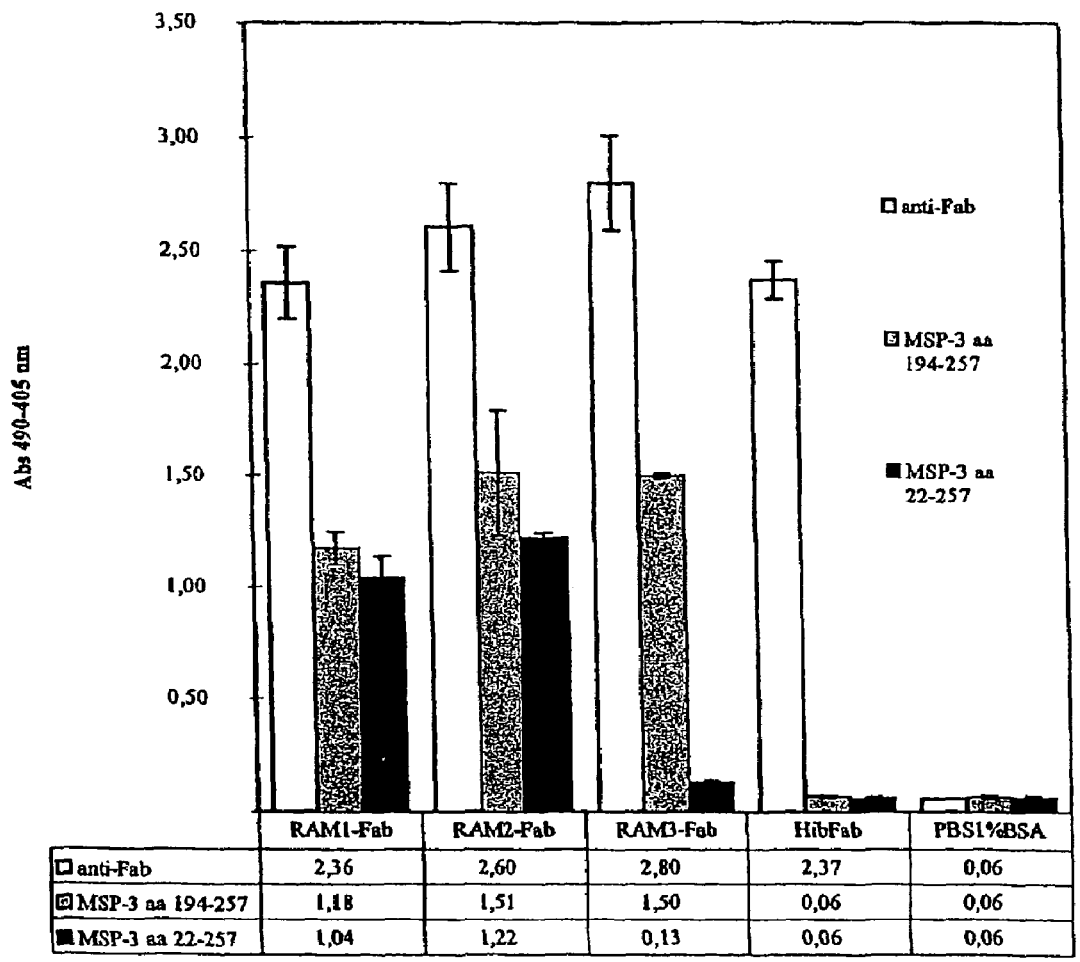

RAM1 VH.
QVQLVQSGGGVVQPGRSLRLSCAASGFTFS   SYAMH   WVRQAPGKGLEWVA   VISYDGSNKYYADSVKG   RFTISRDNSKNTLYLQMSSLRAEDTAVYYCVK   GASS   WSTGTLVTVSS A
                                 CDR1                    CDR2                                              CDR3

DIVMMQSPATLSASVGDRVTITC   RASQSISSWLA   WYQQKPGQAPNLLIY   KASSLES   GVPSRFSGSGSGTEFTLTISSLQPDDFATYC   QQYKSPYT   FGQGTRLEIK R
                          CDR1                           CDR2                                       CDR3

RAM1 Vk.

---

RAM2 VH.
QVQLQESGGGLVKPGGSLRLSCAASGFTFS   SYGMS   WVRQTPDKRLLEWVA   TISSGGSYTYYPDSVRG   RFTISRDNAKNTLYLQMSSLKSEDTAMYYCAR   LYYGYRYYFDY   WGQGTMVTVSS A
                                 CDR1                     CDR2                                               CDR3

DIQLTQSPSSLSASIGDRVTITC   QASQDINSIN   WYQQKPGQAPKLLIY   DAFTLKT   GVPSRFSGRGSGTSFTLAINSFQAEDIGTYFC   QQSERTPFT   FGGGTRVEIK R
                          CDR1                          CDR2                                       CDR3

RAM2 Vk.

---

RAM3 VH.
QVQLVQSGGGVVQPGRSLRLSCAASGFTFS   SYAMH   WVRQAPGKGLEWVA   VISYDGSNKYYADSVKG   RFTISRDNSKNTLYLQMNSLRAEDKAVYYCAR   DSGGLARLGGYFDL   WGRGTTVTVSS A
                                 CDR1                    CDR2                                                CDR3

DIRMTQSPSFLSASVGDRVTITC   RASQGISSYLA   WYQQKPGQAPKLLIY   AASTLQS   GVPSRFSGSGSGTEFTLTISSLQPEDFATYYC   QQGFT   FGGGTKVEIK R
                          CDR1                           CDR2                                        CDR3

RAM3 Vk.

Figure 6

Table I
Results of screening of single clones from the three series after the fourth panning.

| Series | Stringency Factor | Number of clones tested | Fab producers | Binders to MSP-3$_{193-256}$ | Distribution Numbers in brackets |
|---|---|---|---|---|---|
| A | 20 | 118 | 2 | 0 | NA |
| B | 10 | 132 | 9 | 8 | RAM1 (7) + RAM3 (1) |
| C | 5 | 126 | 12 | 9 | RAM1 (7) + RAM2 (2) |
| Total | | 376 | 23 | 17 | |

Table 1

RECOMBINANT ANTI-*PLASMODIUM FALCIPARUM* ANTIBODIES

The present invention relates to recombinant antibodies against the malaria parasite, e.g. *Plasmodium falciparum*, to methods of producing such antibodies, and to uses and methods of use of such antibodies. In particular, the invention relates to antibodies against a specific antigen; MSP-3.

PRIOR ART

Every year more than 2.5 million people, mostly children, die of malaria.

The mortality and morbidity of this disease places a devastating burden on the societies of the developing world. The United Nations has estimated that the loss of production due to malaria in many African countries equals 5% of the gross national product.

Resistance of the malaria parasite (*P. falciparum*) to the existing anti-malarial drug chloroquine emerged in the sixties and has been spreading since then. In addition, the malaria parasite has developed resistance to most other anti-malarial drugs over the past decade. This poses a major threat to public health. There is every reason to believe that the prevalence and degree of anti-malarial drug resistance will continue to increase. Furthermore, many anti-malaria drugs have been notorious for their toxic side effects, e.g. mefloquin.

It has been previously shown that anti-parasitic activity from an immune donor can be transferred by IgG into non-immune receivers (McGregor et al. 1963; McGregor 1964), and that such antibodies do not act directly, but act indirectly through a mechanism termed antibody-dependent cellular inhibition of growth (ADCI, Bouharoun et al. 1990). This mechanism works preferentially with IgG1 and IgG3 (Bouharoun-Tayoun et al. 1992; Shi et al. 1999); (Aribot et al. 1996).

Using an ADCI assay, the merozoite surface antigen (MSP-3) was previously identified (Oeuvray et al. 1994). Affinity purified human polyclonal anti-MSP-3 antibodies have also been used in a mouse model (Badell et al. 2000).

There are a number of difficulties in using the antibodies described above, i.e. those purified from an infected host in the prevention or treatment of malaria. From a practical point of view it is highly unlikely that serum from infected individuals would ever be approved for medical use (for obvious safety reasons). Neither would sufficient amounts of antibodies be available.

In principle, recombinant human antibodies with appropriate specificity and activity were desirable. However, there have been difficulties in the art in developing these. For example, Seehaus et al. (1992) describes problems associated with the occurrence of deletion mutants in phage display protocols, which, despite being undesirable, tend to replicate faster than "intact" phages and so become over-represented.

DISCLOSURE OF THE INVENTION

The present inventors have, for the first time, developed recombinant human antibodies specific for the MSP-3 antigen. These antibodies are able to passively induce naturally occurring non-sterile malaria immunity (termed premunition) and exert their effect via the ADCI mechanism. Additionally, the recombinant antibodies may stimulate phagocytosis of infected erythrocytes and free parasites. Yet another mechanism of action of the antibodies may be direct interference with the function of the MSP-3 and/or the MSP-6 molecules by binding to the epitope.

Specifically, the inventors generated a phage display system based on the amplification of genes from the human peripheral blood leukocytes of 13 malaria immune individuals which encode variable regions (V) of antibody. These genes were isolated by the polymerase chain reaction (PCR).

Following amplification of the V region genes, these genes were cloned into a compatible phagemid vector, which directs expression of antibody fragments. The resultant phage display library was screened using a fragment of the merozoite surface protein, MSP-3; MSP-$3_{194-257}$ (Oeuvray et al. 1994).

Specifically, the inventors developed a new panning strategy to screen the library. In this method, biotinylated MSP-$3_{194-257}$ antigen was coupled to streptavidin coated polystyrene beads (Dynabeads), and incubated with the phage library.

The inventors thought that good binders would be present in very low frequency in the initial stock. To recover a high proportion of rare good binders, a high initial concentration of antigen was thought to be needed. However, in subsequent steps the good binders were assumed to be present with increasing frequency. So, the inventors reduced the amount of antigen used in each panning. This avoided the survival of mediocre binders.

The inventors strategy involved reduction of the number of antigen coated beads in subsequent pannings. In this way, both the amount of antigen and the area of matrix (the beads) are reduced concomitantly.

This concomitant reduction of the surface area of the matrix and the amount of antigen avoids a selective advantage of deletion mutants surviving by non-specific adherence to matrix.

The selection procedure resulted in isolation of three distinct clones designated RAM1, RAM2 and RAM3. RAM1 was predominant in the 376 phage-clones examined. Epitope mapping performed on these clones revealed the relationship between these clones.

The reactivity of the clones with native malaria antigen was demonstrated by immunoblotting, immunofluorescence and flow cytometry.

The RAM1, RAM2 and RAM3 clones were produced as intact human IgG1 and intact IgG3 antibody in eukaryotic CHO cells. These antibodies have been purified to more than 99% purity.

Aspects of the Invention

Accordingly, in a first aspect the present invention provides a recombinant human antibody comprising an antibody sequence specific for the MSP-3 antigen of *Plasmodium falciparum*.

An antibody is specific for a particular antigen if it binds that particular antigen in preference to other antigens. In particular, the antibody may not show any significant binding to molecules other than that particular antigen, and specificity may be defined by the difference in affinity between the target antigen and other non-target antigens. An antibody may also be specific for a particular epitope which may be carried by a number of antigens, in which case the antibody will be able to bind to the various antigens carrying that epitope. For example, specific binding may exist when the dissociation constant for a dimeric complex of antibody and antigen is 1 µM, preferably 100 nM and most preferably 1 nM or lower.

The recombinant human antibody of the invention is preferably specific for the C-terminus of the MSP3 antigen, preferably the MSP-$3_{194-257}$ antigen.

The recombinant human antibody of the invention may be specific for the epitope having the amino acid sequence ILG-WEFGGGVP (SEQ ID NO: 10) which corresponds to residues 220-230 of the MSP-3 antigen. This sequence is also conserved in other antigens such as the MSP-6 antigen of *Plasmodium falciparum* (Trucco et al. 2001).

The recombinant human antibody may comprise a CDR sequence selected from: CDR1 of RAM1 VH; CDR2 of RAM1 VH; CDR3 of RAM1 VH; CDR1 of RAM1 VK; CDR2 of RAM1 VK; CDR3 of RAM1 VK; CDR1 of RAM2 VH; CDR2 of RAM2 VH; CDR3 of RAM2 VH; CDR1 of RAM2 VK; CDR2 of RAM2 VK; CDR3 of RAM2 VK; CDR1 of RAM3 VH; CDR2 of RAM3 VH; CDR3 of RAM3 VH; CDR1 of RAM3 VK; CDR2 of RAM3 VK; or CDR3 of RAM3 VK, having the sequences shown in FIG. 6 (the CDRs are marked and are underlined on FIG. 6).

Preferably, the antibody comprises the CDR3 from a heavy chain, that is a CDR selected from: CDR3 of RAM1 VH; CDR3 of RAM2 VH; or CDR3 of RAM3 VH, having the sequences as shown in FIG. 6.

More preferably, the antibody comprises two or more CDRs shown in FIG. 6, i.e. two or more CDRs selected from CDR1 of RAM1 VH; CDR2 of RAM1 VH; CDR3 of RAM1 VH; CDR1 of RAM1 VK; CDR2 of RAM1 VK; CDR3 of RAM1 VK; CDR1 of RAM2 VH; CDR2 of RAM2 VH; CDR3 of RAM2 VH; CDR1 of RAM2 VK; CDR2 of RAM2 VK; CDR3 of RAM2 VK; CDR1 of RAM3 VH; CDR2 of RAM3 VH; CDR3 of RAM3 VH; CDR1 of RAM3 VK; CDR2 of RAM3 VK; or CDR3 of RAM3 VK having the sequence shown in FIG. 6.

The antibody may comprise any one of CDR1, CDR2, and CDR3 of a heavy chain as shown in FIG. 6 and any one CDR1, CDR2 and CDR3 of a light chain as shown in FIG. 6. For example the antibody may comprise CDR3 of a heavy chain and CDR1 of a light chain. Or, the antibody may comprise two or more CDRs from a heavy chain, or two or more CDRs from a light chain as shown on FIG. 6.

Most preferred is that the antibody comprises CDR1, CDR2 and CDR3 of a light chain as shown in FIG. 6, and CDR1, CDR2 and CDR3 of a heavy chain as shown in FIG. 6.

It is preferred that, where the antibody comprise two or more CDRs, the two or more CDRs are from the same RAM clone, that is two or more CDRs from RAM1; two or more CDRs from RAM2 or two or more CDRs from RAM3.

It is most preferred that the antibody comprises the CDR1, CDR2, CDR3 of the light chain and CDR1, CDR2 and CDR3 of the heavy chain, wherein all six CDRs are from the same RAM clone, e.g. all six CDRs are from RAM1.

Although it is preferred that within a single antibody the CDRs are from a single RAM clone, e.g. RAM1, RAM2 or RAM3, any combination is possible, that is where the antibody comprises two or more CDRs as disclosed herein, a first CDR may be from any one of RAM1; RAM2 and RAM3 and the second CDR may be from any of RAM1; RAM2 or RAM3. To produce combinations in which CDRs derive from different RAM clones, CDR shuffling (Jirholt P, Ohlin M, Borrebaeck Calif., Soderlind E. (1998). Exploiting sequence space: shuffling in vivo formed complementarity determining regions into a master framework. Gene 1998 Jul 30; 215 (2) : 417-6) or DNA shuffling may be used (Crameri et al., 1996).

Preferably, the recombinant human antibody may comprise a $V_H$ domain (Variable domain of the heavy chain) selected from RAM1 VH; RAM2 VH or RAM3 VH having the amino acid sequence shown in FIG. 6 (the VH amino acid sequences are shown as the top line for each RAM clone in FIG. 6).

Preferably, the recombinant human antibody has a $V_L$ domain (Variable domain of the light chain) selected from RAM1 VK; RAM2 VK; or RAM3 VK having the amino acid sequence of RAM1, RAM2 or RAM3 shown in FIG. 6 (the VK amino acid sequences are shown as the bottom line for each RAM clone in FIG. 6). Any light chain may be combined with any heavy chain, e.g., by light and heavy chain shuffling (Marks et al. 1992).

However, it is preferred that the recombinant human antibody has the $V_L$ domain of RAM 1 VK and the VH domain of RAM1 VH; or the VL domain of RAM2 VK and the VH domain of RAM2 VH; or the VL domain of RAM3 VK and the VH domain of RAM3 VK, as shown in FIG. 6.

The variable heavy chain regions discussed above may be combined with any suitable constant region, including the constant region of gamma 1, gamma 2, gamma 3, gamma 4, my, alfa 1, alfa 2, delta or epsilon isotypes as well as any artificial constant region. It is preferred that the recombinant human antibody comprises a constant region of the gamma 1, gamma 2, gamma 3, or gamma 4 isotypes, to form an IgG molecule.

More preferably, the recombinant human antibody comprises a constant region of the gamma 1 or the gamma 3 isotypes, to form an IgG1 or IgG3 isotype.

For each isotype, any subclass and any allotype may be used. It is desirable that antibodies for therapeutic use should have as little immunogenic effect in the recipient as possible. Therefore it is desirable that the allotype of a therapeutic antibody is one which the recipient normally expresses. Therefore common allotypes are preferred. Preferred IgG1 and IgG3 allotypes include G1m(a,z) and G3m(b). Further preferred allotypes include G1m(f), G3m(c3c5), G3m(c3) and G3m(s).

Alternatively, other molecules capable of eliciting the desired effector functions or anti-parasitic effects may be coupled to the antigen-binding region of the antibodies, e.g. enzymes with anti-parasitic effects. For example, the use of such antibodies may confer target selectivity to an otherwise toxic drug or substance.

Preferably the antibodies of the present invention are capable of mediating antibody-dependent cellular inhibition (ADCI) of *P. falciparum* in vitro, resulting in *P. falciparum* killing by the methods described herein, or known in the art (e.g. Bouharoun-Tayoun et al., 1995).

Preferably the antibodies are capable of inducing an antigen specific decrease in *P. falciparum* parasitemia in a suitable immunocompromised animal model grafted with parasitised human red blood cells, e.g. the P. F.-HuRBC-BXN model described herein, or the mouse models described by Badell et al. (1995; 2000). In some embodiments a fast decrease is achieved.

Preferably the antibodies of the present invention are capable of clearing *P. falciparum* parasitemia from such an animal model.

In some embodiments, the antibodies of the present invention will exert effects either in vivo, or in vitro comparable to those obtained with polyclonal antibodies purified from immune human donors, e.g. total IgG, or antibodies affinity purified on MSP3 antigens, such as full length or C-terminal recombinant MSP3 protein, or the MSP3b peptide described herein. In some embodiments the effects are exerted in vivo and in vitro. In some embodiments the recombinant antibodies provide the same degree of *P. falciparum* killing as the antibodies obtained from donors. Thus some embodiments of the invention will provide a profound biological effect on *P. falciparum* under both in vivo and in vitro conditions.

The recombinant human antibodies of the invention may be produced by expression from a suitable nucleic acid molecule.

In addition to an antibody sequence, the antibody may comprise other amino acids, e.g. to impart to the molecule another functional characteristic in addition to ability to bind antigen. For example, the specific binding member may comprise a label, or enzyme and so on (as discussed in more detail below).

In addition to the complete antibody, fragments of the antibody may also have the ability to bind the appropriate antigen (such as MSP-3), and are therefore also encompassed by the invention. For example, it has been shown that fragments of a whole antibody can perform the function of binding antigens. Examples of binding fragments are (i) the Fab fragment consisting of VL, VH, CL and CH1 domains; (ii) the Fv fragment consisting of the VL and VH domains of a single antibody; (iii) isolated CDR regions; (iv) F(ab')2 fragments, a bivalent fragment comprising two linked Fab fragments (v) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (vi) bispecific single chain Fv dimers (PCT/US92/09965) and (vii) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

Accordingly, in a further aspect the present invention provides an isolated nucleic acid molecule comprising a nucleic acid sequence encoding a recombinant human antibody of the first aspect.

Such a nucleic acid molecule may be in the form of a recombinant and preferably replicable vector.

Such a 'vector' may be any plasmid, cosmid, or phage in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Any suitable host may be used, including bacteria, e.g. archaebacteria, plants, plant cells, fungi or animal cells.

Generally speaking, those skilled in the art are well able to construct vectors and design protocols for recombinant gene expression. For further details see, for example, *Molecular Cloning: a Laboratory Manual*: 2nd edition, Sambrook et al, 1989, Cold Spring Harbor Laboratory Press (or later editions of this work)and *Current Protocols in Molecular Biology*, Second Edition, Ausubel et al. eds., John Wiley & Sons, 1992, which are incorporated herein by reference.

Preferred vectors include the plasmids pLNOH2 or pLNOK which are described in Norderhaug et al. 1997 (and discussed in more detail later). Other suitable vectors for expresssion of antibodies are described in Sanna et al. 1999; Persic et al. 1997; Walls et al. 1993.

Plasmids pLNOH2 and pLNOK may be expressed by any suitable cell type, e.g. mammalian, yeast, insect or plant cells, especially mammalian cells such as BHK, CHO, or COS cells, using methods which are standard in the art. CHO or BHK cells are most preferred.

It is preferred that the antibody is secreted to the media by the cell from which it is expressed.

Further aspects of the invention relate to: a method of expressing in a host cell an antibody as described herein from a nucleic acid molecule described herein; a host cell capable of expressing an antibody as described herein in appropriate culture conditions for producing said antibody; a method of producing an antibody comprising culturing such a host cell under appropriate conditions, which method may further comprise isolating said antibody from the cell culture, and which method may further comprise admixing the isolated antibody with a suitable further component (which may, for example, be another antibody or an excipient or carrier).

Mammalian cells may be transfected by any suitable technique such as lipofection. One suitable method is described in the Examples. Alternatively, standard calcium phosphate transfection or electroporation may be used, which is well understood by the skilled person.

The recombinant antibodies produced from these expression systems and nucleic acid molecules of the invention are preferably provided in a substantially pure or homogeneous form. Recombinant antibodies may be purified by any suitable method such as ammonium sulphate precipitation, preferably followed by purification using a DEAE Sepaharose column and an ABx column (Baker Bond). This may optionally be followed by a gel filtration step, e.g. using Superdex200.

In a further aspect of the invention, there is provided a method for screening a phage display library, comprising the following steps:
(i) attaching a target molecule (such as an antigen) to a bead using a suitable linker;
(ii) admixing a first amount of such beads with attached target molecule with a first population of phage from a phage display library (which library expresses sequences (such as antibody sequences) which may bind to the target molecule;
(iii) selecting from the first population of phage a second population of phage, wherein the second population of phage is enriched in phage which bind to the target molecule;
(iv) admixing said second population of phage with a second amount of beads, wherein said second amount of beads is smaller than said first amount;
(v) selecting from said second population of phage a third population of phage, wherein said third population of phage enriched in phage which bind to the target molecule.

Steps (iv) and (v) may be repeated to produce fourth and fifth populations.

Using this method, the amount of target molecule and area of binding matrix (total bead surface area) are reduced concomitantly.

It is preferred that the target molecule is an antigen and the phage display library contains antibody sequences.

A suitable linker for attachment of the target molecule to the bead is an avidin-biotin linker.

A suitable reduction between the first and second amounts of beads is a reduction by a factor of 10. For example, where the first amount of beads is $7\times10^5$ the second amount of beads may be 70000. If steps (iv) to (v) are repeated then a third amount of beads may be around 7000.

Other reductions in the amount of beads are also possible and can be varied by the skilled person. The reductions do not need to be the same throughout the method. For example, the reduction between first and second amounts may be by a factor of 10, and between the second and third amounts may be a factor of 5. In another example, the reduction in between first and second amounts may be by a factor of 2 and between second and third amounts may be by a factor of 5.

The method of screening a phage display library may (where the phage display library contains antibody sequences) be followed by the further step of producing a complete antibody. Producing a complete antibody may comprise insertion of the antibody sequences isolated from the phage display library into a suitable vector (such as pLNOH2 and pLNOK, as described herein) and expressing the antibody from that vector in an appropriate cell type.

Antibodies produced or producible by such a method represent a further aspect of the invention.

Uses of Antibodies

The antibodies disclosed herein can be used for treatment or for prevention of a malarial disease.

The term "malarial disease" includes clinical, e.g. clinical symptomatic infection, clinical asymptomatic infection and cerebral malaria.

Accordingly, in a further aspect the present invention provides recombinant human antibodies disclosed herein for use in the treatment or prophylaxis of a malarial disease.

The invention further encompasses the use of recombinant human antibodies disclosed herein in the manufacture of a medicament (e.g. a vaccine) for the treatment or prophylaxis of malaria. The medicament may further comprise a suitable excipient or carrier.

Suitable excipient, carriers, buffers, stabilises are well known to those skilled in the art. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Methods of treatment or prophylaxis of malaria form further aspects of the invention, such methods may comprise administering a recombinant human antibody as described herein to an individual.

In the above methods and uses, the recombinant antibodies may be administered to the individual in any of the following ways: intravenous injection; intramuscular injection; subdermal injection; oral administration e.g. using capsules to protect the antibody during passage to the stomach; administration in toothpaste (whereby the antibody is transferred to the circulation by the abrasive effects in the oral mucosa); administration by the use of occlusive plasters or skin ointment for penetration through the skin; administration through the nasal mucosa by delivery with a spray; and rectal administration.

Suitable doses for treatment may be 10 μg to 10 mg of antibody per kg body weight or less depending on the affinity of the antibody, preferably 1 mg to 10 mg, more preferably 0.1 mg to 3.5 mg, more preferably 1.5 mg to 3.5 mg, most preferably 2 mg antibody per kg body weight.

Suitable doses for prevention may be smaller due to the lower load of parasites to be eliminated, such as 0.1 μg to 3 mg, preferably 0.1 mg to 2 mg, more preferably 0.5 mg to 1.5 mg, more preferably 0.75 mg to 1 mg most preferably 1 mg antibody per kg body weight.

Suitable administration schemes may be based upon an in vivo half-life for the antibodies of the IgG1 class of around to 23 days and an in vivo half-life for the IgG3 class of around 6 days.

Alternatively, or additionally, the nucleic acid molecule encoding the antibody may be used in the treatment or prevention of malarial disease. In this way the DNA is injected into the individual and the antibody is produced endogenously in that individual.

Accordingly, further aspects of the invention relate to: the nucleic acid molecules described herein for use in the treatment or prophylaxis of a malarial disease; the use of nucleic acid molecules described herein in the manufacture of a medicament (e.g. a vaccine) for the treatment or prophylaxis of malaria; and methods of treatment or prophylaxis of malaria comprising administering a nucleic acid molecule as described herein to an individual.

Suitable vectors for the administration of nucleic acid molecules to an individual include adenovirus and adeno-associated virus, and retrovirus vectors, in addition to other particles that introduce DNA into cells, such as liposomes.

A further aspect of the present invention provides a method which comprises causing or allowing binding of an antibody as provided herein to a target antigen.

Such binding may take place in vivo, e.g. following administration of an antibody, or nucleic acid encoding a antibody, or it may take place in vitro, for example in ELISA, Western blotting, immunocytochemistry, immuno-precipitation or affinity chromatography.

In vivo, this may be useful for vaccine where the antibodies disclosed herein may serve as an adjuvant to enhance the endogenous immune response. Alternatively, the antibodies disclosed herein may serve as transport molecule facilitating the uptake of the MSP-3 antigen, e.g. from the intestinal tract (for this latter function IgA is preferred). When the antibodies disclosed herein are administered in vivo during natural infection with P. falciparum a protective endogenous immune response is facilitated, i.e. passive immunization combined with infection facilitates active immunization (Zhang et al. 2002; Manca et al. 1988).

The amount or extent of binding of specific binding member to a target antigen may be determined. Quantitation may be related to the amount of the antigen in a test sample, which may be of diagnostic interest.

The reactivities of specific binding members on a sample may be determined by any appropriate means. Radioimmunoassay (RIA) is one possibility. Radioactive labelled antigen is mixed with unlabelled antigen (the test sample) and allowed to bind to the specific binding member. Bound antigen is physically separated from unbound antigen and the amount of radioactive antigen bound to the specific binding member determined. The more antigen there is in the test sample the less radioactive antigen will bind to the specific binding member. A binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

The present invention also provides the use of a specific binding member as above for measuring antigen levels in a competition assay, that is to say a method of measuring the level of antigen in a sample by employing a specific binding member as provided by the present invention in a competition assay. This may be where the physical separation of bound from unbound antigen is not required. Linking a reporter molecule to the specific binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

Thus a further aspect of the invention is a method of diagnosis of malaria. Such a method may comprise taking a sample of bodily fluid from an individual, contacting the sample with an antibody as described herein and determining the binding of that antibody to the sample, thereby determining the presence or absence of a target antigen in the sample. Thus the binding of an anti-MSP-3 antibody described herein would show the presence of the MSP-3 antigen in the sample.

In addition, antibodies according to the invention may be used in methods to assist in the identification or production of molecules with anti-parasitic, e.g. anti *Plasmodium falciparum* activity. In this way, antibodies may be used to guide the selection of novel antibodies against the MSP-3 antigen or cross reactive antigen (Ohlin et al, 1996; Jirholt et al, 1998), or the antibodies may be used to identify the single components in the protective mechanisms responsible for the anti-parasitic effects and to identify other substances enhancing or interfering with these effects.

The invention will now be described in detail with reference to the following figures and examples, which are non-limiting.

BRIEF DESCRIPTION OF THE DRAWINGS AND TABLE I

FIG. 1 shows ELISA reactivity with various truncated versions of MSP-3. Fab-ΔpIII fragments produced from the three distinct clones were analysed in ELISA. Truncated recombinantly produced, MSP-$3_{22-257}$ (black bars) , MSP-$3_{194-257}$ (grey bars) were used as coating antigens in separate analyses. An ELISA for detection of Fab fragments (Anti-Fab) was included to ensure use of comparable amounts of the various Fab fragments (white bars). Background was measured as reactivity with the control Fab against HibCP and as reactivity with buffer. Reactivities are indicated as $OD_{405}$-$OD_{490}$. Bars indicated median values and error-bars indicated 2 times standard deviation of triplicates.

Figure 2:
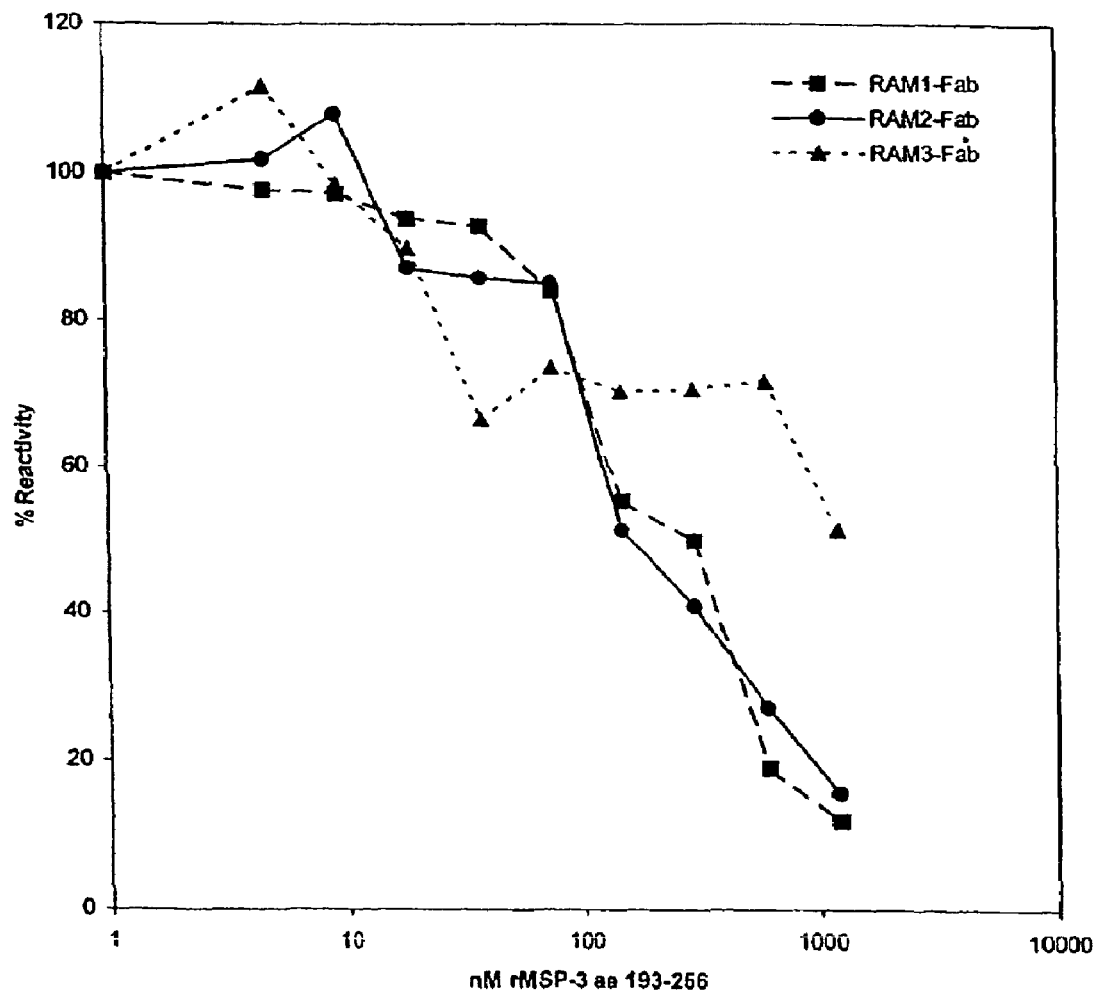

FIG. 2 shows results of the antigen competition experiments. Fab-ΔpIII from the three distinct clones were competed with soluble panning antigen in ELISA. All three clones were susceptible to competition with soluble MSP-$3_{194-257}$. A constant amount of Fab-ΔpIII produced from each of the three distinct clones was mixed with varying amounts of competition antigen, MSP-$3_{194-257}$, and applied to ELISA wells coated with the same antigen. Percent reactivity in the ELISA was calculated taking the reactivity with no antigen added as 100%.

Figure 3:
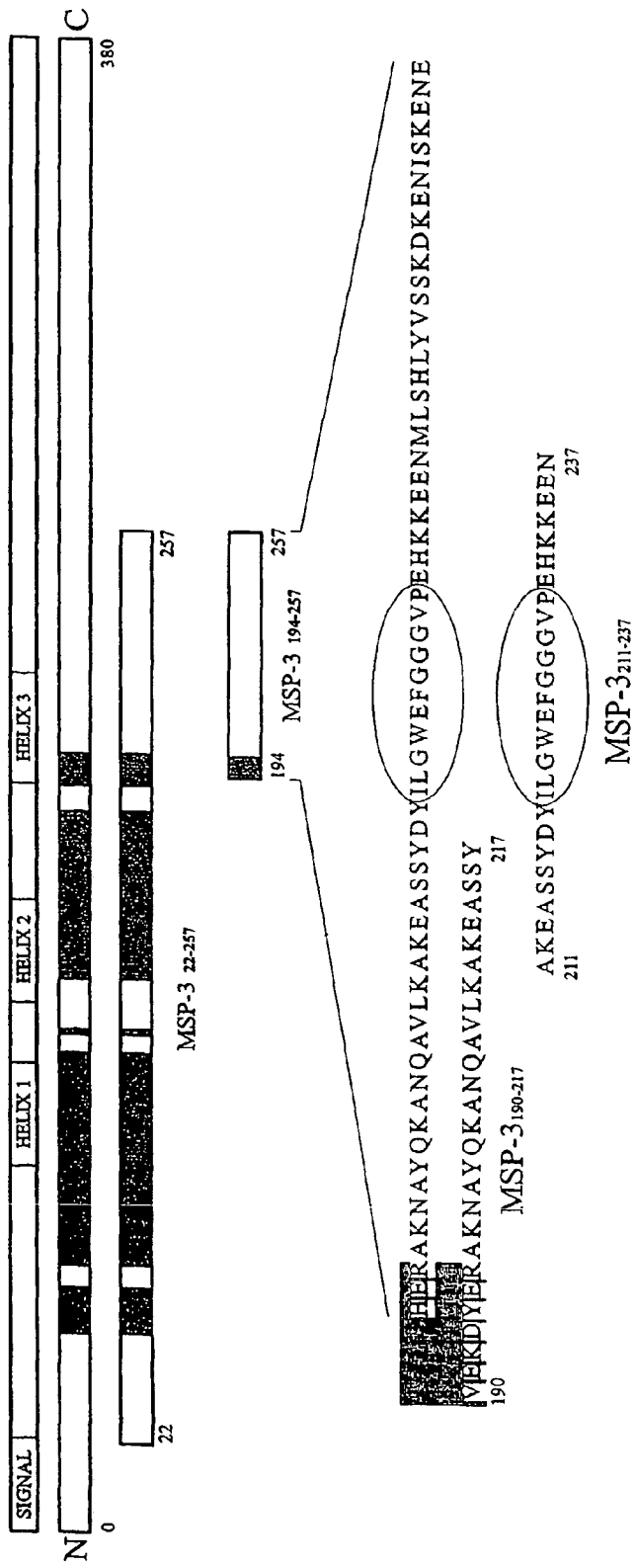

FIG. 3 shows a schematic representation of the entire MSP-3 antigen (top, MSP-$3_{1-380}$) and the relationship of the truncated antigens (MSP-$3_{22-257}$, MSP-$3_{194-257}$, (SEQ ID NO: 7), MSP-$3_{190-217}$ (SEQ ID NO: 8) and MSP-$3_{211-237}$ (SEQ ID NO: 9)used). The numbering above has been assigned according to the *P. falciparum* clone D10, sequenced by McColl et al. 1994 (Genbank accession number L07944). As this numbering may be different when aligned with other clones, the MSP-$3_{194-257}$ (Oeuvray et al. 1994, accession number AF024624) amino acid sequence has been written in the figure.

The intact antigen comprises 12 heptad repeats, equally distributed into the three heptad repeat regions (HELIX 1, HELIX 2, HELIX 3). Analyses of the sequence of the regions suggest that they have an amphipatic α-helical secondary structure and in the presence of all three regions can obtain the structure of a coiled-coil three-stranded helical bundle (McColl et al. 1994; Mulhern et al. 1995). The helix regions and signal peptide (SIGNAL) are indicated as boxes at the top of the drawing. The dimorphic areas described by Huber et al. (1997) are indicated with gray shading. The MSP-$3_{190-217}$ peptide represents the Helix 3 sequence of the K1 clone (McColl et al. 1997, accession number U08851).

The motif represented by amino acid residues 220-230, ILGWEFGGGVP (SEQ ID NO: 10), is indicated by oval figures. This motif is present in MSP-3 as well as in the other *Plasmodium falciparum* antigen MSP-6 (Trucco et al. 2001).

Figure 4:
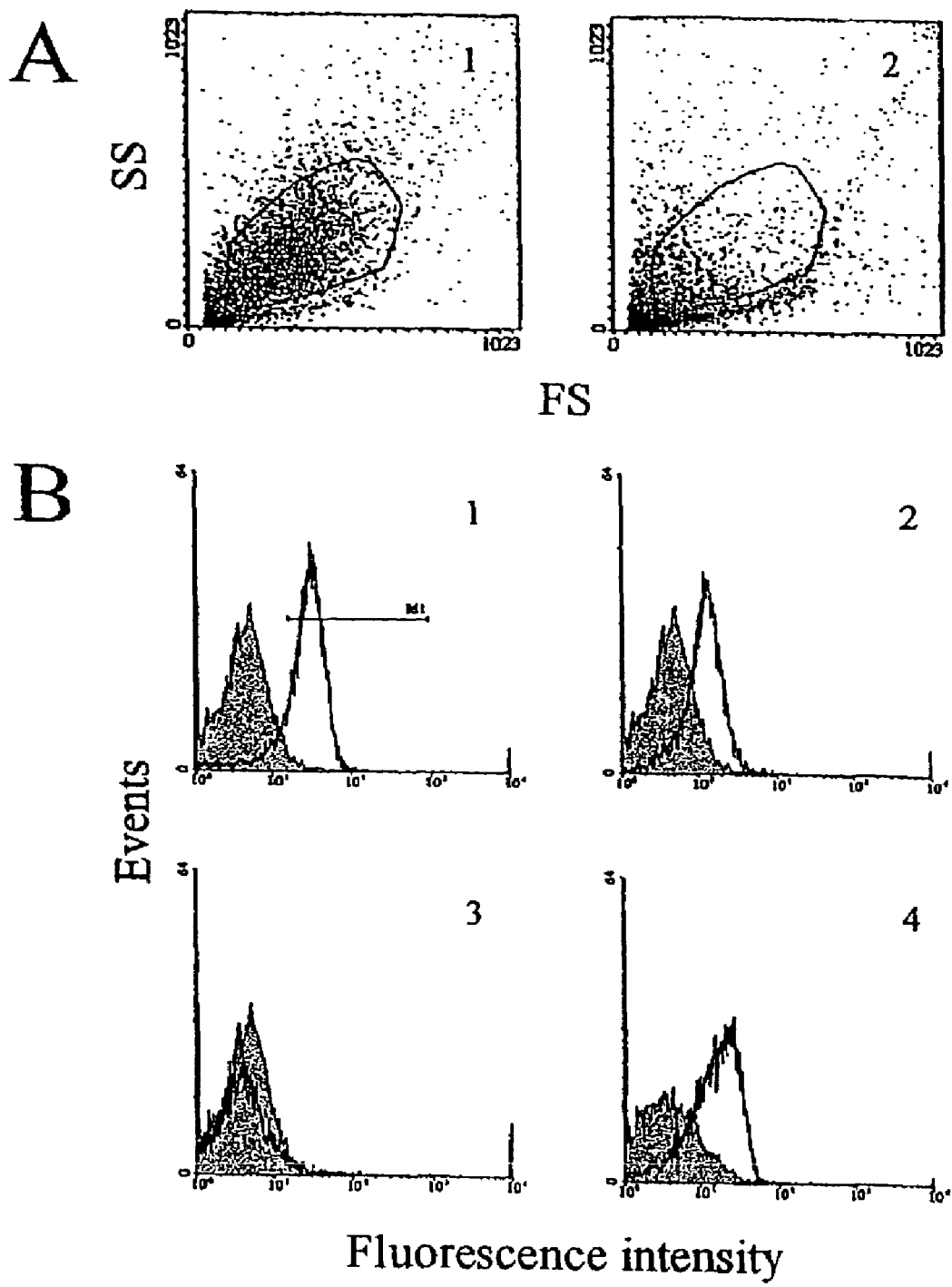

FIG. 4 shows the results of the flow cytometry analyses of the reactivity of recombinant antibodies with schizonts. Panel A1 illustrates forward scatter and side scatter for ethanol-fixed and —permeabilized infected red blood cells, and panel A2 illustrates the same parameters for similarly treated non-infected red blood cells. The gating was placed to include the majority of the infected cells. The gating was used for the histograms described below.

Panel B1 to 4 illustrates histograms of various recombinant anti-malaria antibodies compared with the control antibody directed against HibCP antigen (grey shaded curve). The control histogram has 2% of the events under the bar designated M1 in panel B1.

B1 shows RAM1 in the Fab-ΔpIII format. The bar covers 76% of the events registered.

B2 shows RAM2 in the Fab-ΔpIII format. The bar covers 28% of the events registered.

B3 shows RAM3 in the Fab-ΔpIII format. The bar covers 4% of the events registered.

B4 shows RAM1 in the IgG1 format. The bar covers 47% of the events registered. The control in the IgG1 format has 4% of the events under the bar.

Schizonts were purified from asynchronous *P. falciparum* culture. Fixation and permeabilization was carried out with ethanol. Primary reaction with recombinant antibody was carried out over night and the FITC-labeled secondary antibody was incubated with the cells for 30 minutes.

Figure 5:
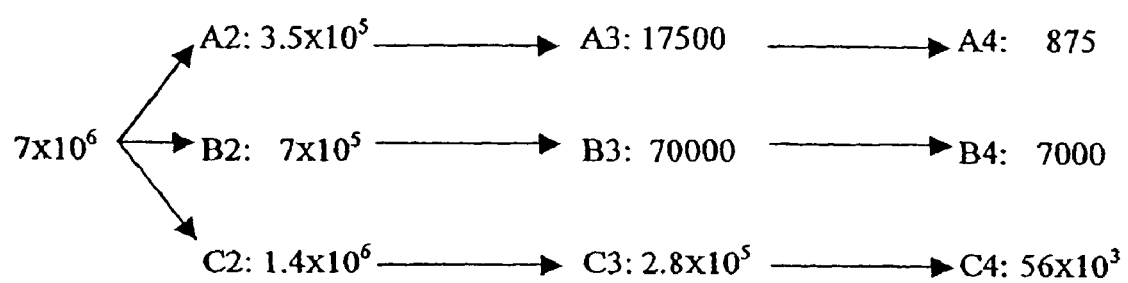

FIG. 5 shows a schematic representation of the panning procedure. Three parallel series (A to C) of panning were carried out for 4 rounds designated 1 to 4. The number of antigen-coated beads used in each round was reduced by a constant reduction factor through the study. The number of beads used for each stage is indicated in the figure.

FIG. 6 shows the deduced amino acid sequences of the three clones. The entire VH and VK sequences of each clone, RAM1(SEQ ID NOS 1-2, respectively, in order or appearance), RAM2 (SEQ ID NOS 3-4, respectively, in order or appearance) and RAM3 (SEQ ID NOS 5-6, respectively, in order or appearance) are shown and boxed. Amino acid residues in the CDR regions are underlined. We have chosen to show the Kabat CDR definitions (Kabat et al. 1991).

Figure 7:
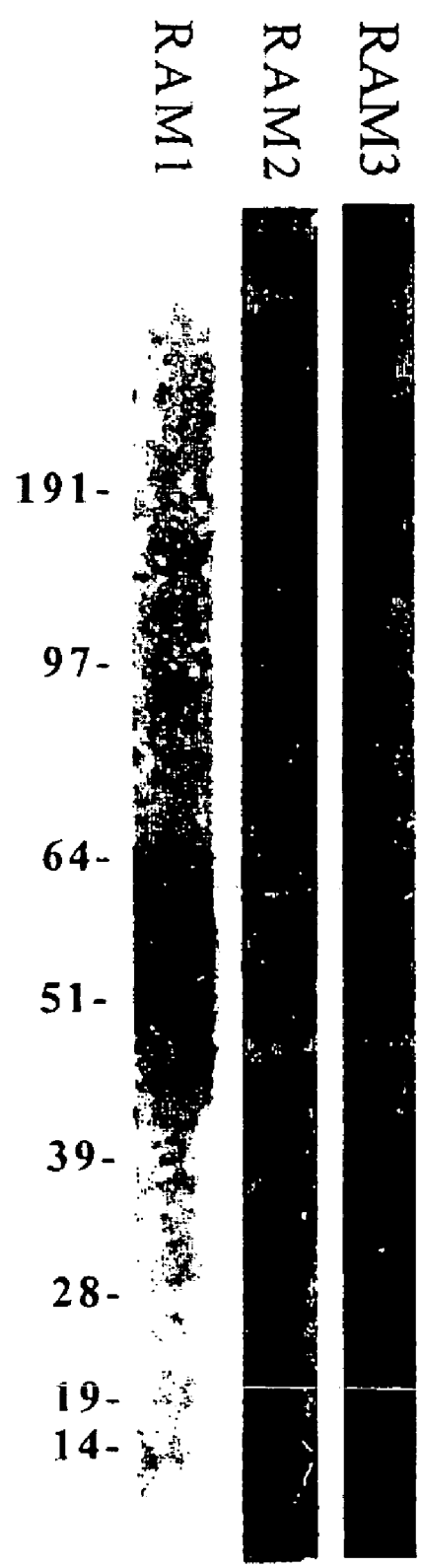

FIG. 7 shows the immunoblotting of *P. falciparum* clone 3D7 schizont and merozoite proteins reacted with RAM1, RAM2 and RAM3 produced as IgG1. All three lanes show a blotting of proteins from purified schizonts separated under reducing conditions on a 4-12% gradient gel. RAM1 IgG1 was reacted with the blotting in lane 1, RAM2 IgG1 was reacted with the blotting in lane 2 and RAM3 IgG1 was reacted with the blotting in lane 3.

RAM1 reacts with two proteins of molecular weights 51 and 53 kD, respectively.

RAM2 reacts with two proteins of approximately relative molecular weights of 64 kD and 14 kD, respectively.

RAM3 reacts with a protein of approximately relative molecular weight of 64 kD identical to the protein recognized by RAM2.

Figure 8:
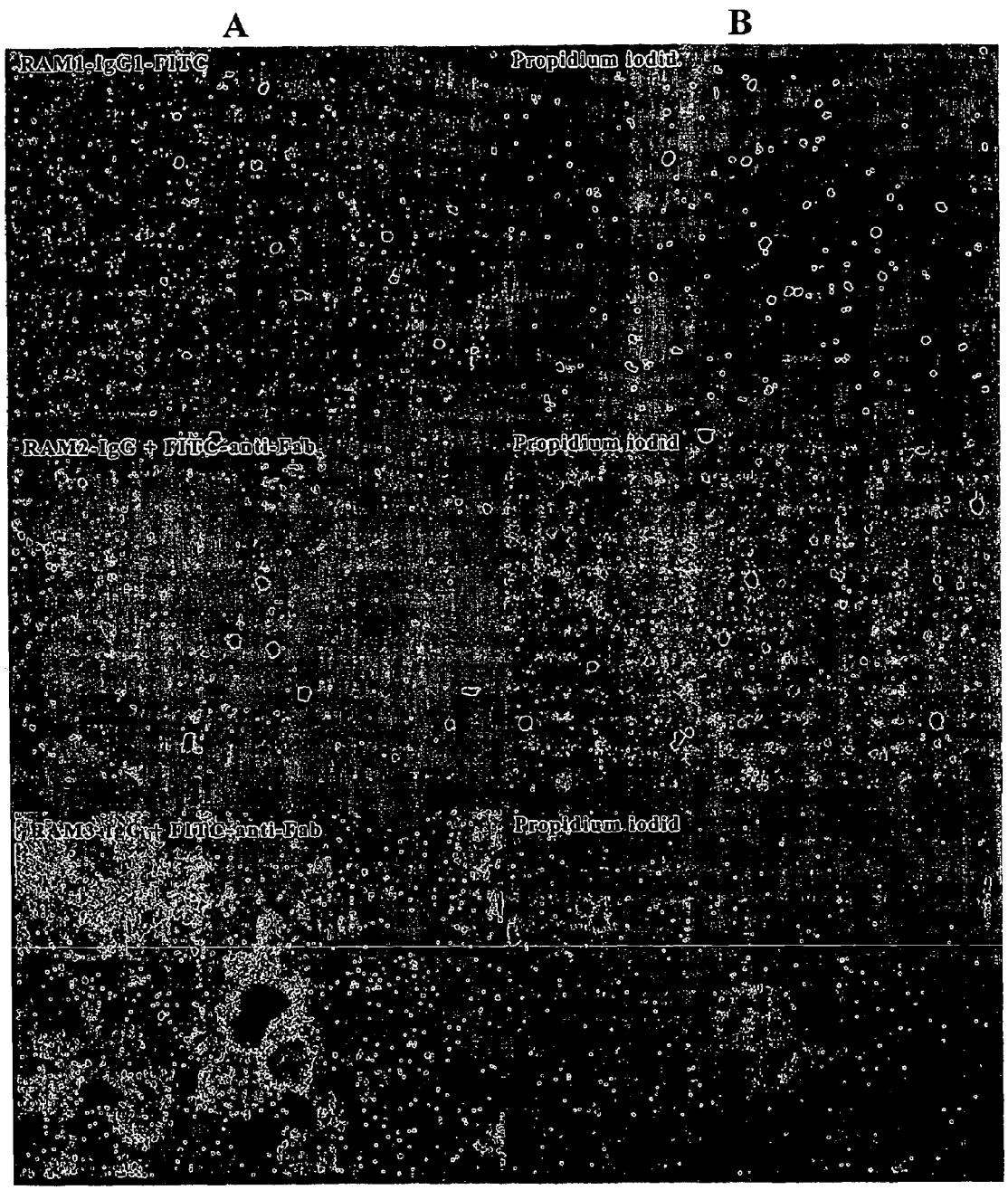

FIG. 8 shows Immunofluorescence microscopy. Panels represent immunofluorescence microscopy of fixed culture of P. falciparum clone 3D7 incubated with FITC-conjugated RAM1IgG1, or RAM2 IgG1 or RAM3 IgG1 followed by a FITC conjugated secondary anti-human Fab. Dots in the A (left) panels indicate red cells carrying antigen reactive with RAM1, RAM2 or RAM3. The B (right) panels represents the same slides stained for DNA with propidium iodide. Large dots in B panels indicate red cells infected with late stage schizonts. By comparing the location of the dots in the A and B panels it is observed that the larger dots in B panels are duplicated in the left panels. Small dots in the B panels are not duplicated in A panels. This demonstrates that late-stage schizonts harbouring merozoites do display the antigen reactive with RAM1, RAM2 or RAM3 whereas early stages do not.

Asynchronous in vitro P. falciparum culture was air-dryed on a slide, fixed with acetone and reacted with FITC-conjugated RAM1 IgG1, or reacted with RAM2 IgG1 or RAM3 IgG1 followed by FITC-conjugated anti-human Fab. No reactivity was detectable with glutaraldehyde fixation.

Figure 9:
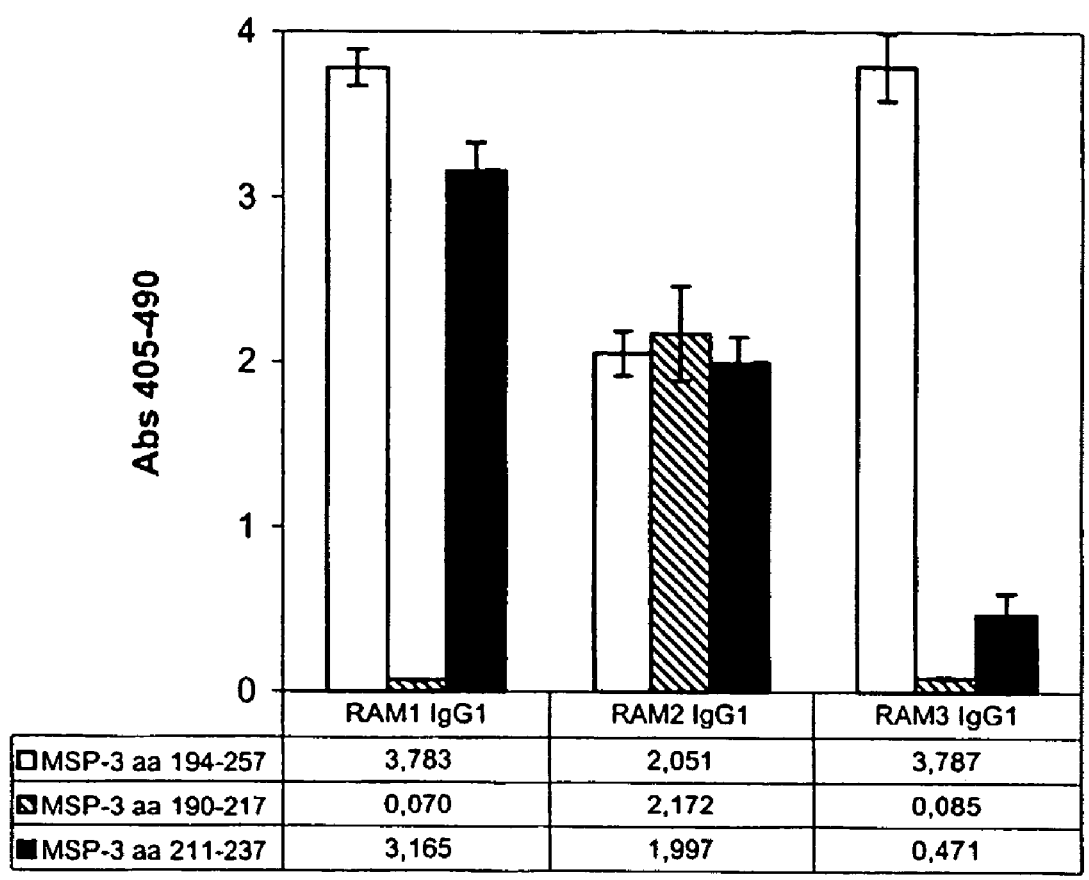

FIG. 9 shows the ELISA reactivity of RAM1 IgG1, RAM2 IgG1 and RAM3 IgG1 with the synthetic peptides MSP-$3_{190-217}$ and MSP-$3_{211-237}$. Also the larger recombinant MSP-$3_{194-257}$ has been included. Error bars represent 2 times standard deviation of duplicates.

Figure 10:
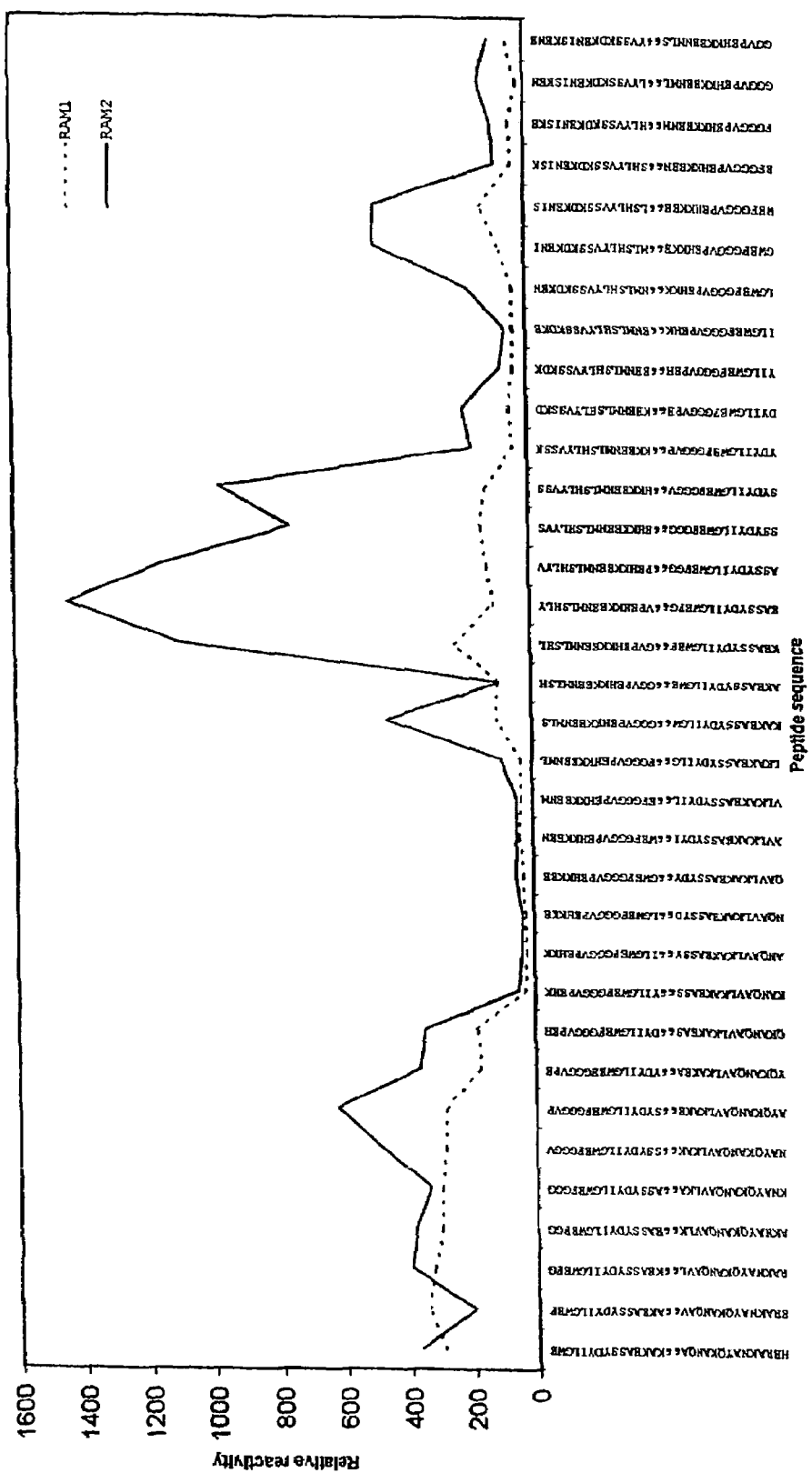

FIG. 10 shows the results from the PEPSCAN screening. The entire sequence MSP-$3_{194-257}$ was covered by synthesis of 34 sets of 14-mer and 15-mer peptides comprising contiguous amino acid sequences (SEQ ID NOS 11-78, respectively, in order or appearance). The two peptides were linked by a proprietary linker substituting two amino acid residues on the location of the linker (PEPSCAN). Thus one single set of peptides covers a stretch of 31 amino acid residues with two amino acid residues replaced in positions 15 and 16 by the proprietary linker residues. The linked peptides were furthermore chemically coupled to the matrix to allow washing and repeated use. The overlap between two adjacent sets of peptides was two amino acid residues. This collection of peptides was examined for reactivity with RAM1 and RAM2 produced as IgG1. RAM2 reacts with the amino-terminal, the middle and the carboxy-terminal part of the antigen but yields the highest reactivity with the middle part. RAM1 reacts only weakly with the peptides produced by this method. RAM3 was tested as Fab-ΔpIII in PEPSCAN without response.

Figure 11:
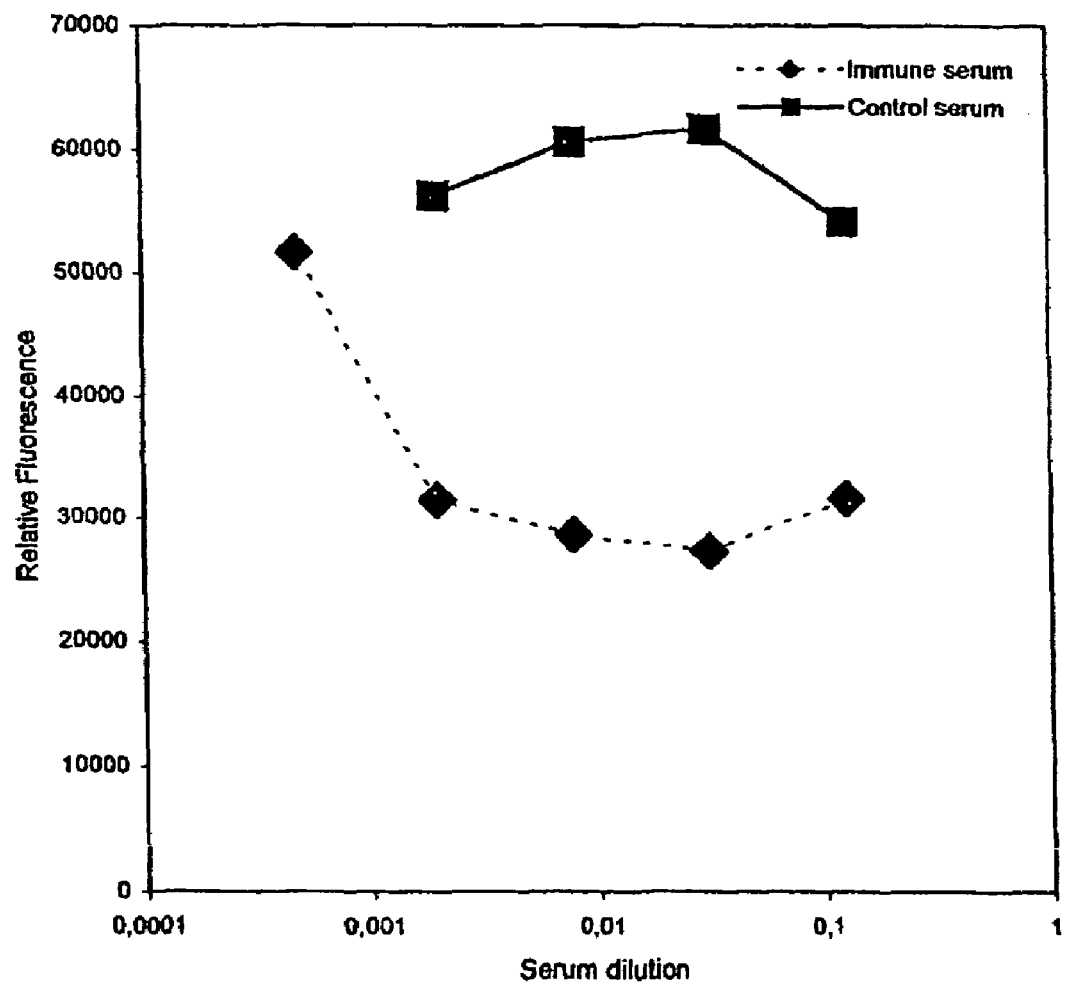

FIG. 11 shows the inhibitory effect of immune serum on the binding of RAM1 IgG1 to MSP-$3_{194-257}$. The FITC-conjugated RAM1 IgG1 antibody was applied to ELISA wells coated with MSP-$3_{194-257}$ were pre-incubated for two hours with dilutions of immune or negative control serum and then a constant amount of FITC-conjugated RAM1 IgG1antibody was applied to each well. Immune serum blocked the binding of RAM1.

Figure 12:
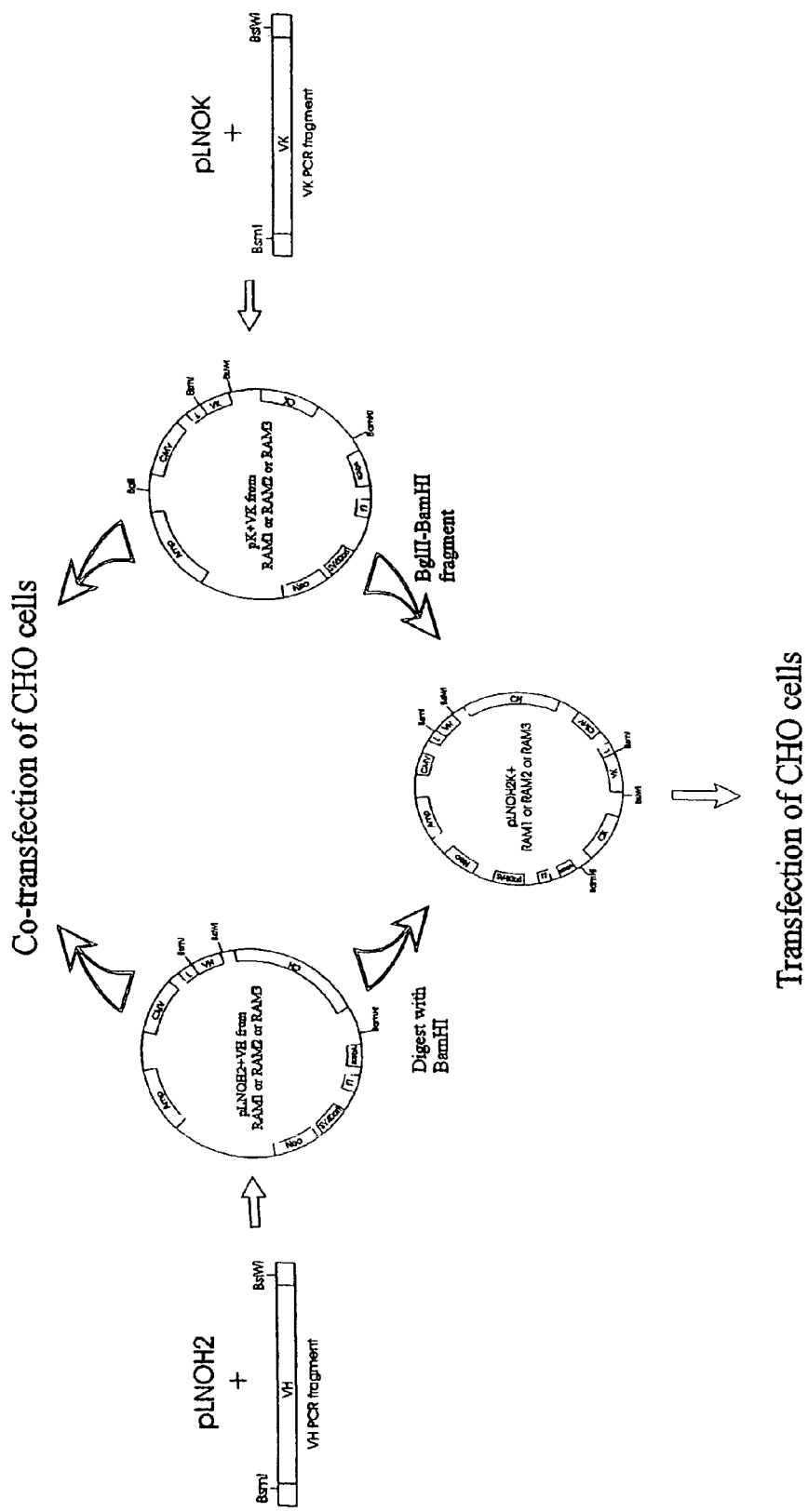

FIG. 12 Construction of expression vectors. The V-regions of the plasmids can be exchanged by cutting with BsmI in the 5' end and by cutting with HpaI or BsiWI or HindIII in the 3' end. Before ligation of vector and V region, the V regions of RAM1, RAM2 or RAM3 need to be cut with the same restriction enzymes as the vectors. VH regions are then ligated to pLNOH2 and VK regions are ligated to pLNOK. The constant region of pLNOH2 can be exchanged by cutting with BamHI and HindIII, isolating the vector part and introducing (by ligation) another constant region cut with the same enzymes.

In order to produce a complete antibody the plasmids (both pLNOH2 and pLNOK) are co-transfected into CHO cells. The V and C-regions are assembled by mRNA splicing. Alternatively the genes can be assembled into one vector thus harbouring the VH plus CH and VL plus CL. This insures that the two genes are present in equimolar numbers.

Abbreviations: CMV=CMV promoter, L=leader, VH=variable heavy, VK=variable kappa, CH=constant heavy chain gene, CK=constant kappa chain gene, BGHpA=Bovine Growth Hormone polyadenylation site, f1=f1 origin, SV40ori=SV40 origin/promoter Neo=gene for neomycin resistance, Amp=gene for ampicillin resistance FIG. 13 Antibody competition. Fab fragments from clone RAM3 were produced in two versions. One version was fusion protein tagged with a truncated phage protein, ΔpIII, designated Fab-ΔpIII, and another version was normal Fab fragments without the ΔpIII tag. The ΔpIII-tag is readily detected using an antibody directed to the phage pIII protein. Thus Fab without ΔpIII can be present as competitor but only Fab-ΔpIII will be detected.

Amounts of RAM1, RAM2 and RAM3 Fab-ΔpIII yielding $OD_{405}$ of approximately 1 in ELISA on a coating of MSP-$3_{194-257}$ were used. The binding of the Fab-ΔpIII was then competed by the addition of increasing amounts of competitor, RAM3 without ΔpIII. This figure shows that Fab RAM3 is able to compete Fab-ΔpIII RAM1 to the same extent as it competes Fab-ΔpIII RAM2. This demonstrates that binding of the clones RAM1 and RAM2 is dependent on the epitope used by clone RAM3. The lower competitive effect of RAM3 on the binding of Fab-ΔpIII RAM3 could be explained by a higher affinity of RAM3 as compared to RAM1 and RAM2. The effect of this would be that the competitive effect of RAM3 towards RAM1 and RAM2 would be larger than towards RAM3 itself.

Figure 14:
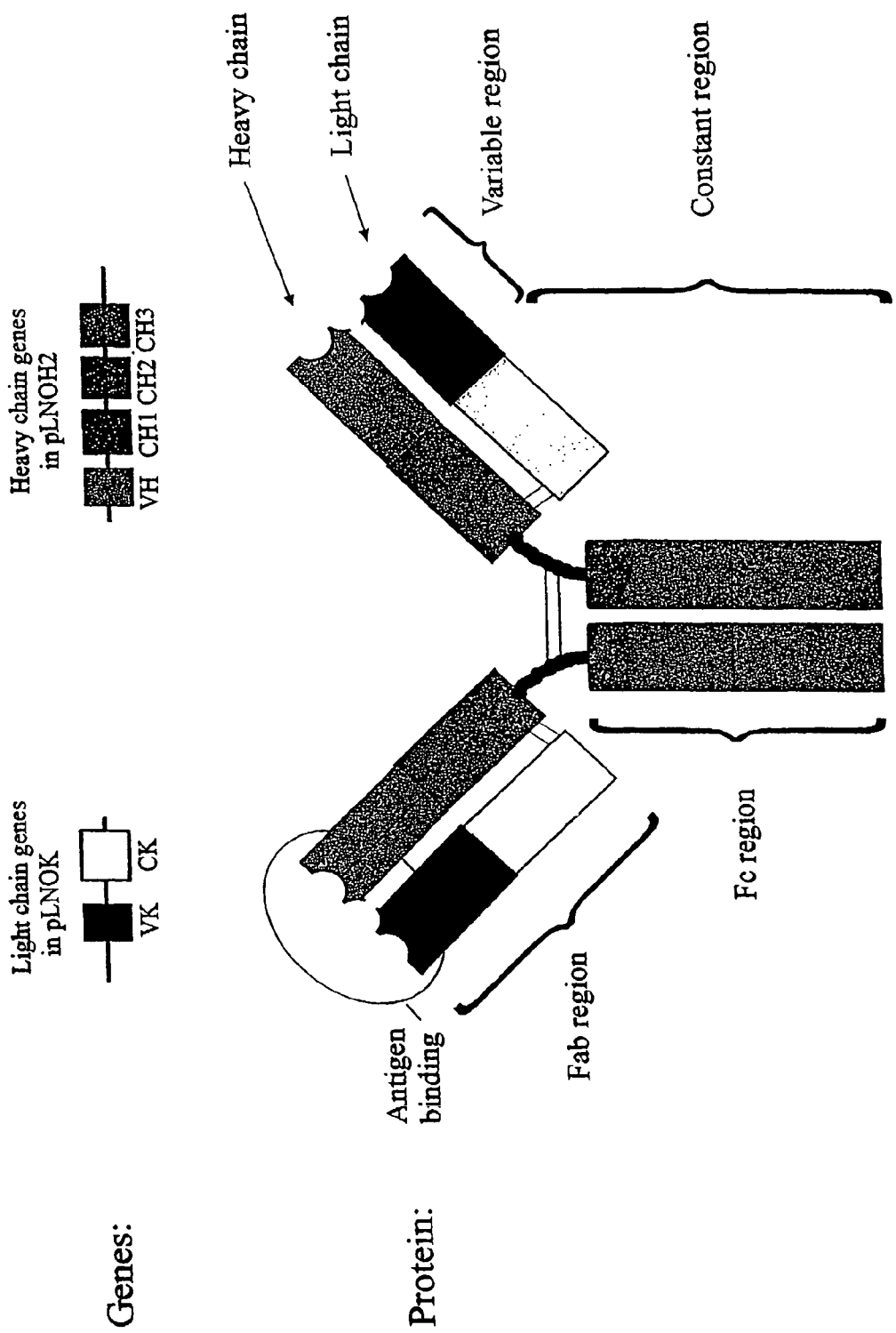

FIG. 14 shows the organization of heavy and light chain genes in pLNOH2 and pLNOK, respectively, and the resulting antibody structure. The part of an antibody responsible for binding to antigen is the variable region, the V-region. This region consists of two separate polypeptides. One polypeptide comes from the light chain and the other from the heavy chain. In the intact antibody the variable region polypeptide from the light chain extends into the constant domain of the light chain, thus giving rise to an approximately 200 amino acid residues long polypeptide with a total of two domains. In the intact antibody the variable region from the heavy chain extends into the constant domains 1 to 3 giving rise to a 400 amino acid residues long polypeptide with a total of four domains. In the intact antibody two heavy chains combine with two light chains. Thus an intact antibody contains two V-regions and is able to bind to two antigens at the same time. The constant regions of the heavy chain interacts with the effector functions of the immune system.

Figure 15:
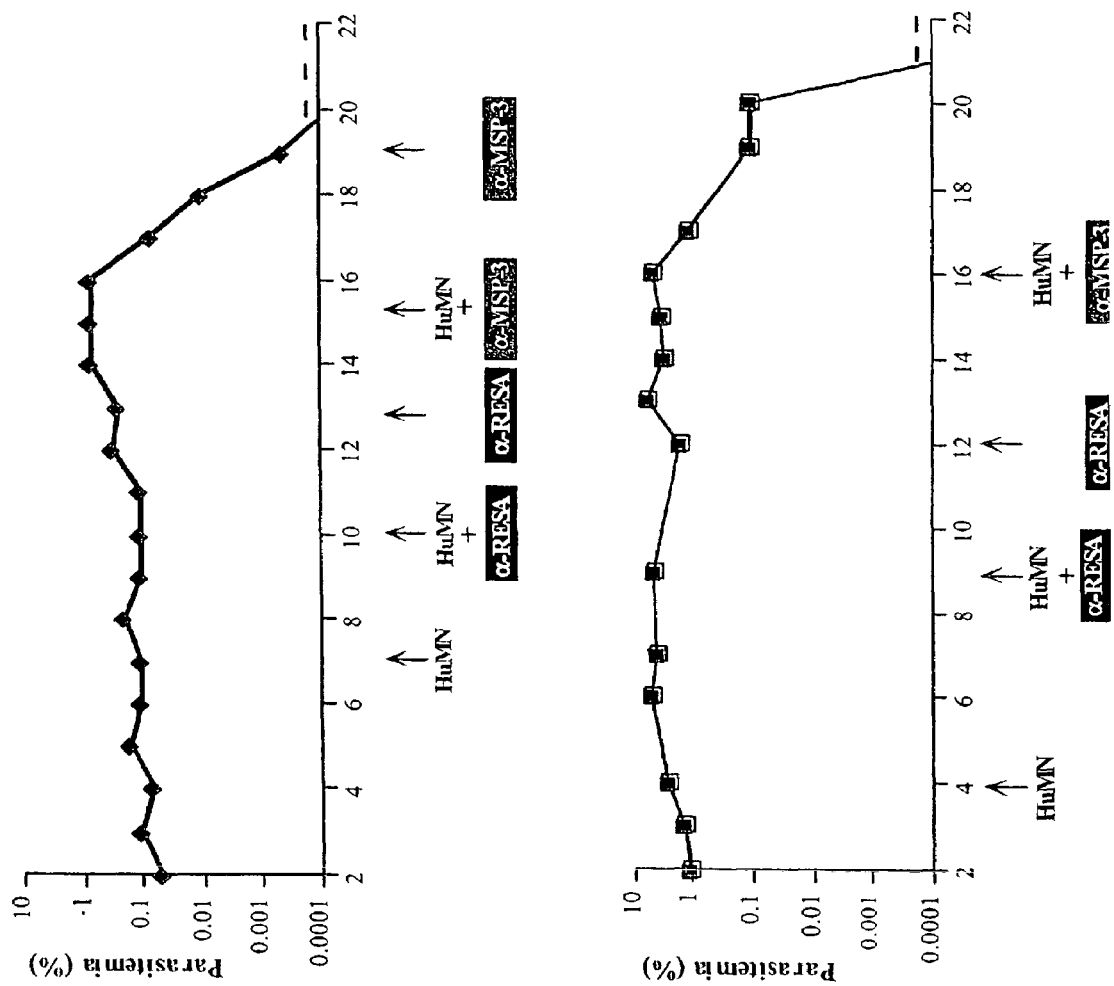

FIG. 15 shows the effects of inoculations of normal human monocytes, polyclonal anti-RESA antibodies and polyclonal anti-MSP3 antibodies from immune human donors on parasitemia in the P.f.-HuRBC-BXN mouse model.

Figure 16:
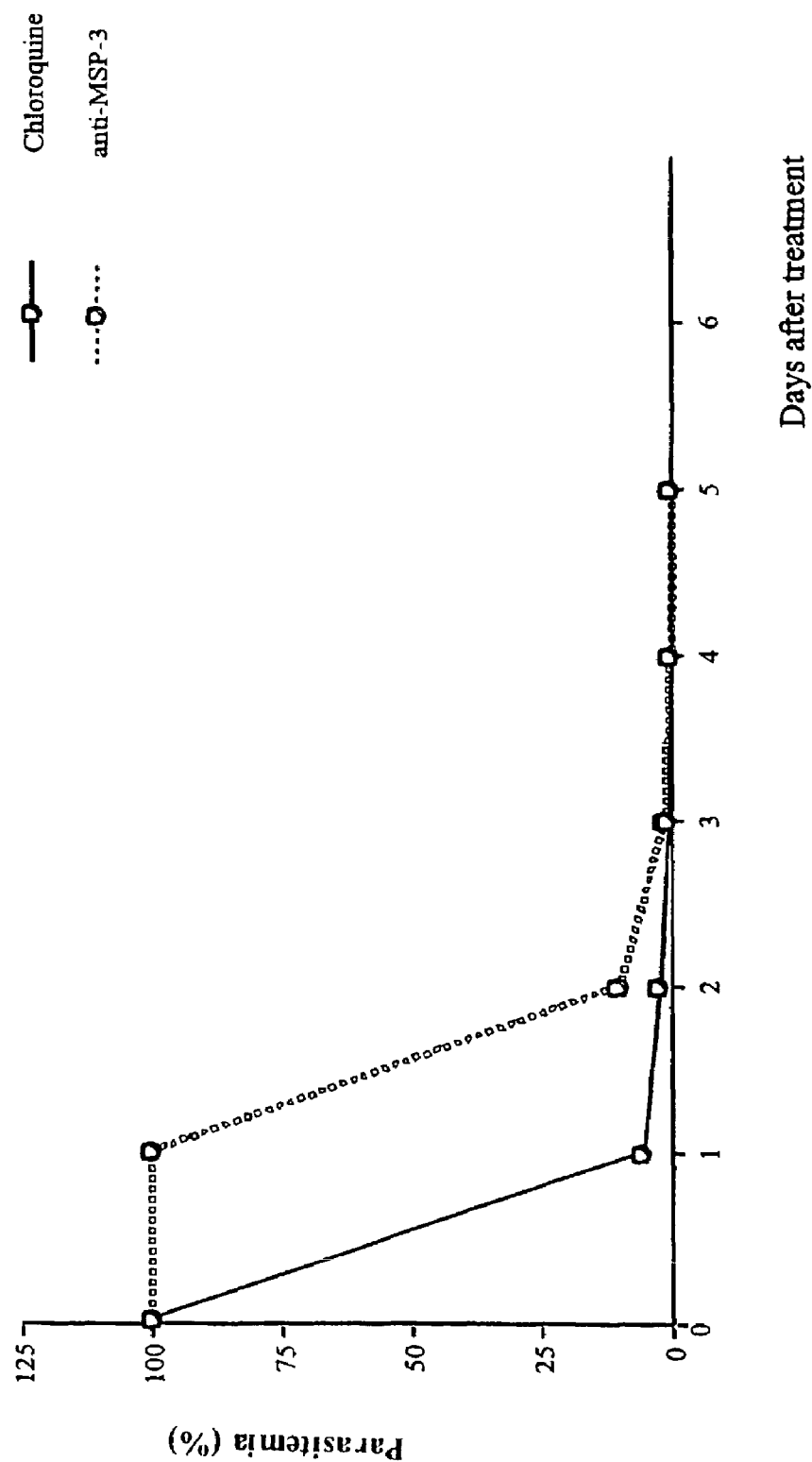

FIG. 16 compares the effects of chloroquine and polyclonal anti-MSP3 antibodies from immune human donors on parasitemia in P.f.-HuRBC-BXN mice.

Figure 17:
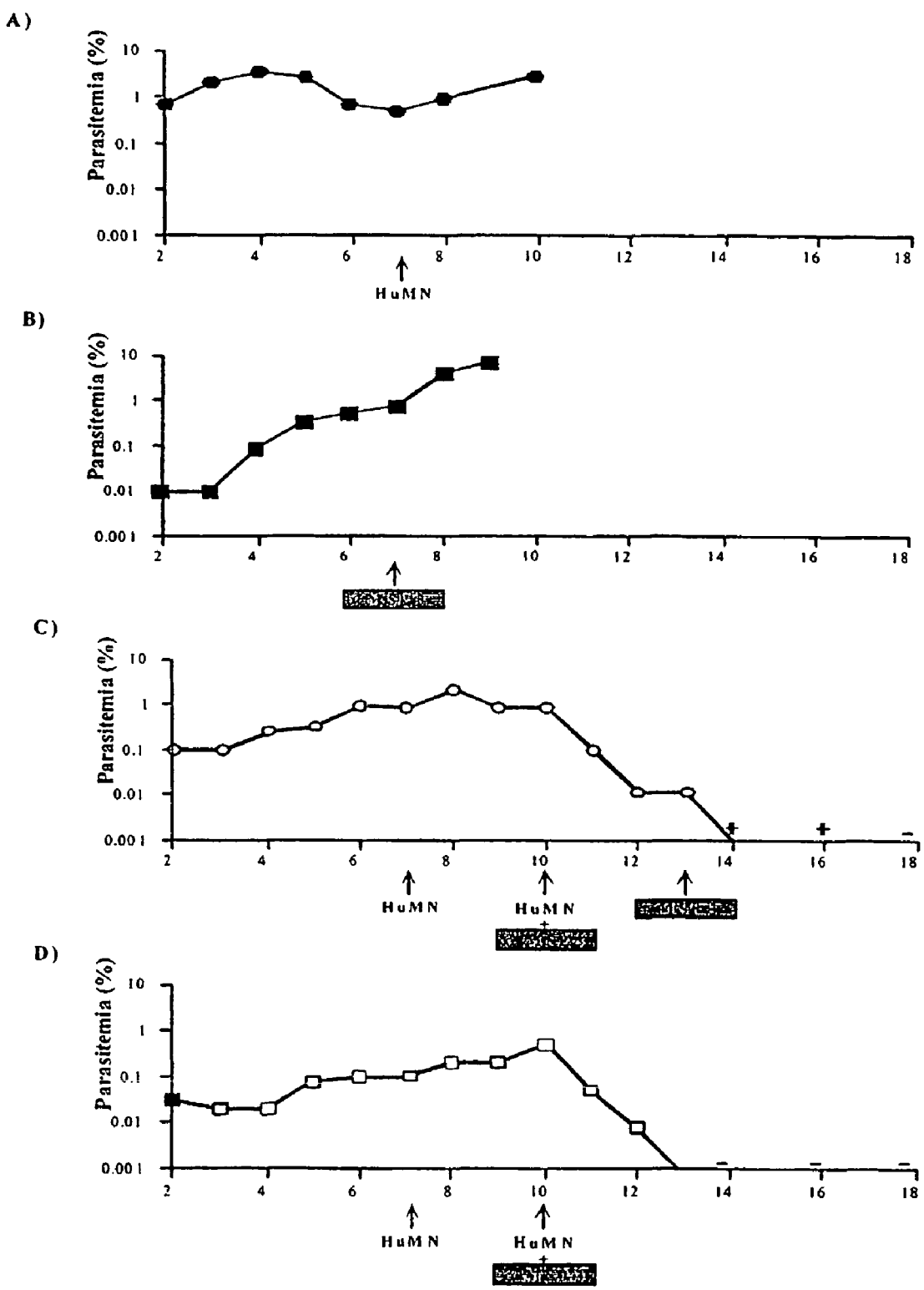

FIG. 17 shows the effects of inoculations of normal human monocytes, polyclonal anti-RESA antibodies and polyclonal anti-MSP3 antibodies from immune human donors on parasitemia in the P.f.-HuRBC-BXN mouse model.

Figure 18:
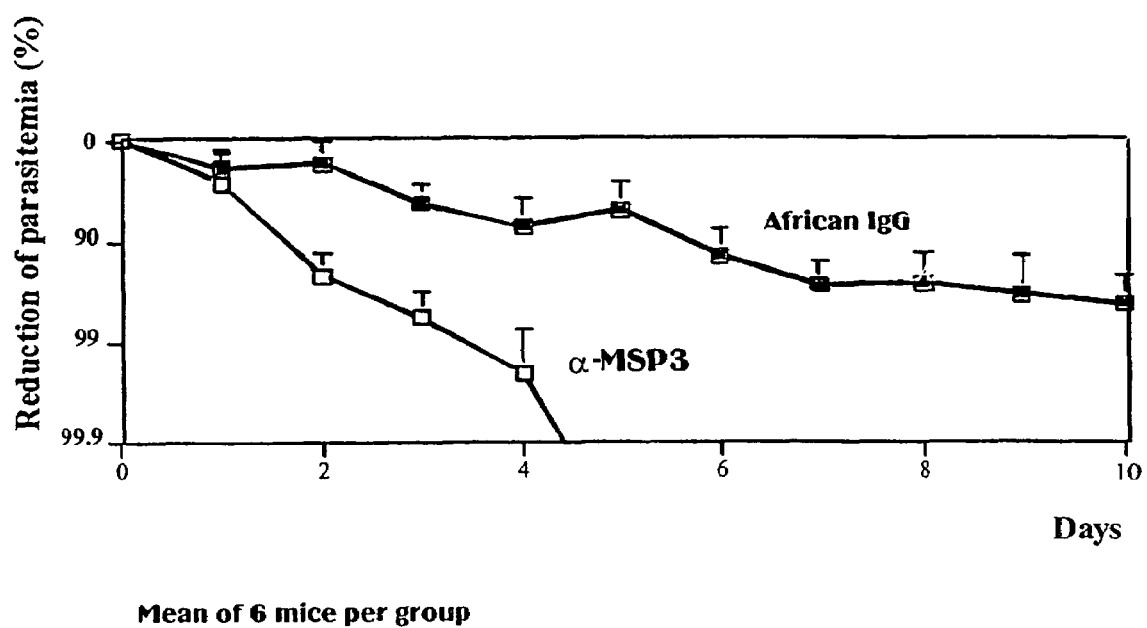

FIG. 18 compares the effects of total IgG from immune donors and antibodies affinity purified on the MSP3b peptide on parasitemia in P.f.-HuRBC-BXN mice, Each curve represents the mean of results from six mice.

Figure 19:
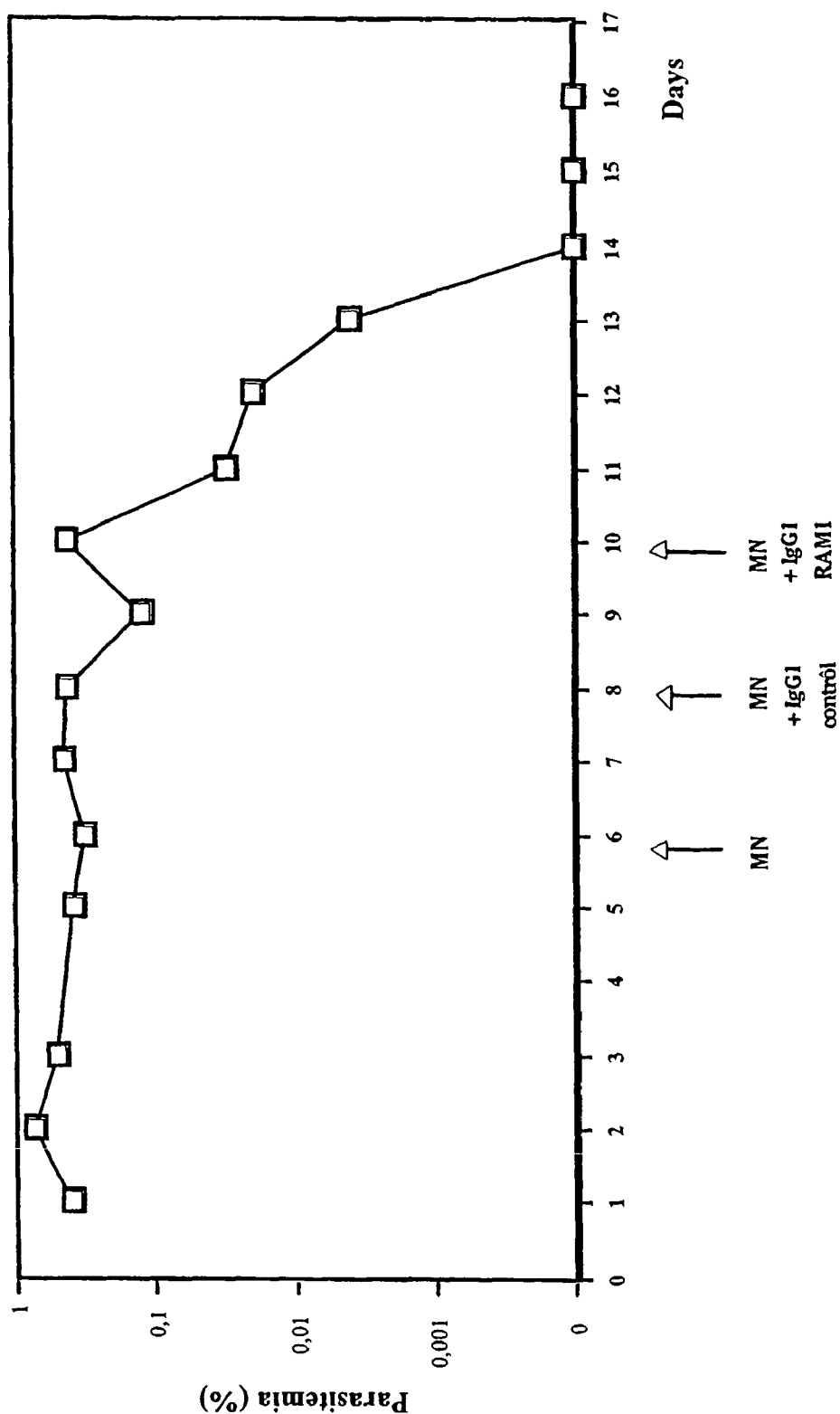

FIG. 19 shows the effects on parasitemia in one P.f.-HuRBC-BXN mouse of inoculations of human monocytes alone, in combination with an IgG1 control antibody, and in combination with RAM1 IgG1.

Table I shows the results of screening of single clones from the three series after the fourth panning.

DETAILED DESCRIPTION OF THE INVENTION

Example 1

Library Construction

Sampling of Peripheral Blood Lymphocytes

A volume of 100 ml peripheral blood was obtained after informed consent from each of 13 adults living in a malaria endemic area of Senegal, West Africa. The blood was collected in the anticoagulant ACD (adenine-citrate-dextrose) that conserves RNA better than heparin. The samples were transported to the laboratory where a brief centrifugation was carried out, the buffy coat aspirated and cells suspended into an RNAse protecting buffer containing guanidinium HCl, beta-mercaptoethanol and sarcosine. The material was then frozen in liquid nitrogen and shipped for further processing.

RNA Purification

RNA was isolated from the samples by acid phenol extraction according to the procedure of Chirgwin et al. (Chirgwin et al. 1979). Messenger RNA was converted to cDNA as described by Ørum et al. (1993).

PCR of Antibody Coding Genes

Amplification of antibody genes was carried out as described previously (Dziegiel et al. 1995). Briefly, separate reactions were performed for the $V_H$ genes, lambda light chain genes, and for the kappa light chain genes. A pool of 12 individual primers was used for priming in the 5' region of the $V_H$ genes (backward primers) and a pool of 3' primers was used for priming in the $J_H$ region (forward primers). The details of the primers are given in Dziegiel (1995).

The amplification product of approximately 350 bp was purified from a low-melting point agarose by digestion of the agarose with agarase (Boehringer-Mannheim, Germany). This fragment was used as a template for a secondary extension PCR with primers complementary to the ends of the primary product and additionally containing sequences corresponding to the restriction enzymes NheI (5') and ApaI (3'). Extended $V_H$ fragments thus have a 5' NheI site and a 3' ApaI site. A pool of 8 primers was used for priming in the 5' region of kappa light chain genes and one primer for priming in the 3' region. For amplification of lambda light chain genes a pool of 12 backward primers and one forward primer were used. The resulting fragment of approximately 700 bp was purified as above and used as template for a secondary extension PCR introducing the restriction enzyme sites SfiI (5') and AscI (3'). Extended kappa chain genes thus have a 5' SfiI site and a 3' AscI site.

Polymerase Chain Reaction

Antibody genes were amplified from cDNA by PCR with separate reactions for $V_H$ region genes, λ chain genes, and κ chain genes, respectively. PCR was performed in 100 µl volumes containing 0.2 mM dNTP's and reaction buffer supplied by the manufacturer (HT Biotechnology, UK), an equimolar mixture of primers totalling 20 µM (i.e. 0.65 µM of each $V_H$ primer, 0.74 µM of each $V_\kappa$ primer, 0.83 µM of each $V_\lambda$ primer, 20 µM of the κ chain constant domain primer, 5 µM of each of the λ chain constant domain primer, and 5 µM of each of the J-region primers), cDNA, and enzyme. An initial one min period at 94° C. was followed by addition of enzyme, and the cycle (94° C. for one min, 55° C. for one min, 72° C. for one min) was then repeated 30 times. Reactions were performed as described (Ørum et al., 1993), except that a HYBAID Omnigene thermocycler was used.

Plasmid pFAB73HHui

The pFAB73HHui vector was developed from pFAB73H (Dziegiel et al., 1995; Engberg et al., 1996). The vector harbors an intact lacI$^q$ gene encoding a highly efficient mutant of the lacI repressor. This ensures a high level of gene repression independent of the bacterial background. The sequences between the NheI-ApaI sites, and between the SfiI-AscI sites have been exchanged with sequences originating from a murine antibody against human insulin. This improves the efficiency of the second digestion and facilitates isolation of double digested plasmid during the subsequent low-melting point agarose electrophoresis. Other features of the plasmid are identical to the pFAB4H. Briefly, pFAB73HHUI contains the DNA fragment encoding amino acid residues 118 to 230 of the human γ1 H chain corresponding to constant domain 1 ($C_H1$). The $C_H1$ gene extends in frame into a truncated version of gene III (ΔgIII) via a DNA fragment encoding a spacer and a trypsin cleavage site. ΔgIII encodes a truncated version of surface protein pIII (ΔpIII) of the filamentous phage, f1 (Bass et al., 1990; Ørum et al., 1993). The lacZ promoter and the 5' part of the PelB leader gene were positioned in front of cloning sites for L chain genes. A DNA fragment containing a ribosome binding site (RBS) and the 5' part of the gene encoding the PelB leader was positioned 5' to cloning sites for H chain variable region ($V_H$) genes.

pFAB73HHUI permits insertion of $V_H$ genes and L chain genes by a two-step cloning procedure, first inserting $V_H$ genes into restriction enzyme sites NheI and ApaI, then inserting L chain genes into the sites SfiI and AscI. All necessary genetic elements and the $C_H1$ are present in the vector, thus minimizing the total number of PCR cycles.

Cloning of Antibody Genes

Amplification products from the secondary extension PCRs were separated on low-melting point agarose followed by digestion with agarase. The extended $V_H$ fragments were digested with restriction enzymes NheI and ApaI in two sequential reactions. The NheI-ApaI-digested $V_H$ gene fragment was purified on a low-melting point agarose gel followed by agarase digestion. The cloning vector, pFAB73HHUI, was digested with restriction enzymes NheI and ApaI in two sequential reactions. The NheI-ApaI-digested 5.4 kb plasmid was purified on a low-melting point agarose gel followed by agarase digestion. The $V_H$ gene was ligated into the plasmid, the ligation mixture was extracted with Phenol and Chloroform, ethanol precipitated and electroporated into E. coli Top10Tet using an E. coli pulser set (BioRad). Bacteria were resuspended in SOC medium (Sambrook et al. 1989), incubated at 37° C. for 1 h with shaking and then plated on LB agar (Sambrook et al. 1989) containing 50 mg/l carbenicillin, 12.5 mg/l tetracycline and 2% glucose. Plates were incubated overnight at 37° C. Colonies were washed off the plates with LB medium with carbenicillin, tetracycline and glucose and used to start a liquid culture, which at $OD_{600}=1$ was used to prepare the recombinant vector using Qiagen columns (Qiagen GmbH, Hilden, Germany) according to the procedures recommended by the manufacturer. The purified vector containing H chain genes was used as cloning vector for the cloning of kappa and lambda light chain genes.

The extended kappa chain products were digested with restriction enzymes AscI and SfiI in two separate reactions. The kappa chain genes were subsequently cloned into SfiI- and AscI-digested pFAB73HHUI harbouring $V_H$ region genes.

Library

The resultant library contained $5 \times 10^7$ different heavy chains, $1 \times 10^8$ kappa light chains and $1 \times 10^8$ lambda light chains. Investigation of $V_H$ genes from 66 clones by PCR and BstNI digestion demonstrated lack of identical digestion patterns thus suggesting acceptable diversity.

In this system, the heavy (H) chain fragment, Fd, is produced as a fusion protein with a truncated version of the filamentous f1 phage protein III (ΔpIII) (Bass ET al. 1990). H chain fusion proteins associate with intact light (L) chains in the periplasmic space to form Fab heterodimers, which are fused to the ΔpIII protein. Upon infection with helper phage, the fusion proteins are positioned on one end of the phage together with a few copies of helper phage-derived wild-type pIII (Clackson et al. 1991; Hoogenboom et al. 1991). Thus, the Fab is able to bind to its specific antigen, and at the same time remains physically associated with the phagemid DNA which harbors the genes encoding that Fab, i.e. a physical linkage has been established between recognition and replication. This allows selection of a given antibody specificity and its corresponding gene from a large number of different Fab-phage (Marks et al. 1991).

Example 2

Selection

Production of Primary Phage Stock

A 50 ml culture of the library in LB medium with 50 mg/l carbenicillin, 12,5 mg/l tetracyclin and 2% glucose was superinfected with VCSM13 helper phage (Stratagene) at an $OD_{600}=0.8$. A multiplicity of infection of 100 was used and the mixture was incubated at 37° C. with gentle shaking (50 rpm) for 1 h. Then the culture was diluted into 950 ml medium as above without glucose and incubated at 30° C. overnight. After a 15-min spin at 10,000×g the supernatant containing phage was precipitated with $PEG_{6000}$ and sodium chloride at final concentrations of 4% and 0.5 M respectively. The supernatant was incubated for 1 h on ice and centrifuged for 30 min at 12,000×g. Precipitated phage was resuspended in phosphate buffered saline (PBS) with 0.1% bovine serum albumin (BSA) and used immediately. The total number of colony forming units was $1.3 \times 10^3$ (determined as per Sambrook et al. 1989).

Selection of Specific Binders in the First Panning

Biotinylated MSP-$3_{194-257}$ was coupled to Dynabeads M-280 Streptavidin (cat no. 112.05) as described by the manufacturer. After incubating the antigen-coated beads with phage in an end-over-end mixer for 1 h, beads were captured with a magnetic particle concentrator (MPC-6, Dynal Cat no. 120.02) for 5 min. and then washed 6 times in 10 ml PBS with 0.05% Tween20 for 2 min. After the last wash beads were resuspended in 1 ml PBS with 1 mg trypsin (Worthington, USA) and phage was eluted during a one-hour incubation at 37° C. Then a volume of 3 ml of exponentially growing Top10 with $OD_{600}=1$ was added and the mixture was incubated at 37° C. for 30 minutes to allow eluted phage to attach to E. coli. The bacteria were finally plated on LB agar (Sambrook et al. 1989) containing 50 mg/l carbenicillin, 12.5 mg/l tetracyclin and 2% glucose and incubated overnight at 37° C. Colonies were washed off the plates with LB medium and stored as a glycerol stock at −80° C. or grown for production of phage and DNA. DNA was produced as described.

Production of Phage for subsequent Pannings

Phage was produced by super-infecting a 15 ml culture of the glycerol stock at $OD_{600}=0.6$ (after approx. 3 hours) by addition of helper phage VCSM13 (Stratagene, USA). Multiplicity of infection was approx. 100. After 1 hour of gentle shaking the culture was diluted into 200 ml of LB-medium and supplemented with isopropyl-β-D-thiogalactopyranoside (IPTG) to give a final concentration of 50 µM, 70 mg/l kanamycin, 50 mg/l Carbenicilin and 12,5 mg/l tetracycline The culture was grown over night. Phage was isolated as above except that it was cleared before panning by two additional spins of each 20 minutes at 17,320×g.

Selection of specific Binders in Subsequent Pannings

Subsequent to the first panning, three series of panning were carried out in parallel, to a total of 4 rounds. In the first series, the number of beads was reduced by a factor of 5 for each subsequent panning. In the second and the third series the number of beads was reduced by a factor of 10 and 20, respectively, from one panning to the next. After the fourth panning single colonies from all three series were grown in sterile microtiter plates for production of Fab-ΔpIII.

Testing of Final Eluate

The eluate from the fourth panning was screened for the presence of Fab-ΔpIII producers and antigen binders, respectively. Fab-ΔpIII was produced by growing individual colonies in microtiter wells. A total of 376 clones were tested. Supernatant from 23 clones contained free Fab-ΔpIII and 17 of these were able to bind to MSP-$3_{194-257}$ (see table I). The antibody genes of the 17 clones were sequenced using Big Dye according to the procedures of the manufacturer (Applied Biosystems, USA).

The selection procedure resulted in isolation of three distinct clones designated RAM1, RAM2 and RAM3.

Example 3

Determination of Specificity

The reactivity of the clones with native malaria antigen was demonstrated.

Direct ELISA

ELISA plates (Maxisorb, NUNC 4-39454, Denmark) were coated with 10 to 650 ng per well of purified recombinant MSP-$3_{22-257}$ or MSP-$3_{194-257}$ or of the peptides MSP-$3_{190-217}$ or MSP-$3_{211-237}$ in PBS and used for standard ELISA with undiluted supernatant or supernatant diluted in PBS-BSA as previously described (Dziegiel et al.1991; Dziegiel et al. 1995). After wash, goat anti-human Fab (Sigma A8542) or anti-human IgG Fc (Sigma A9544) antibodies conjugated to alkaline phosphatase was applied as detection antibody. Finally, p-nitrophenyl phosphate (Sigma phosphatase substrate tablets, 104-105) was used as substrate. Color development was measured as $OD_{405}$-$OD_{490}$, see FIG. 1. RAM1 and RAM2 both bind to the short MSP-$3_{194-257}$ and the long MSP-$3_{22-257}$ recombinant versions of the MSP-3 antigen. In contrast, RAM3 binds only the short MSP-3$_{194-257}$ version. The controls (anti-Hib CP and PBS 1% BSA) do not react with the antigen.

Antigen Competition

To wells containing 50 µl of a fixed dilution of Fab-ΔpIII were added 50 µl of various dilutions of competition antigen, MSP-3$_{193-256}$. Coating of wells with MSP-3$_{194-257}$ and detection of bound antibody were carried out as above. The concentration of competition antigen ranged from 4 nM to 1250 nM. Each dilution of competition antigen was tested in duplicate, see FIG. 2. All three clones are competed by soluble recombinant MSP-3$_{194-257}$ antigen. This demonstrates that the antibodies are directed to the conformation of the antigen in solution and not to some denaturation-dependent conformation e.g. a plastic-binding dependent epitope.

Immunofluorescence Microscopy

Parasitized erythrocytes from in vitro culture of *P. falciparum* clone 3D7 were attached to a slide, air dried and then fixed with acetone for 5 minutes at room temperature as described (Druilhe et al. 1987). Fab-ΔpIII or intact IgG1 was added and after 30 minutes slides were washed in PBS. Bound Fab-ΔpIII was detected with FITC-conjugated goat anti-human Fab (Sigma F5512) diluted 1:25. Hib-CP specific antibody was used as control in corresponding concentrations. To stain the DNA-containing infected erythrocytes propidium iodide was added to the secondary antibody solution. The late schizont stage was intensively stained with propidium iodide due to its high content of merozoite DNA. The RAM1 Fab stained exactly this stage. In contrast, red cells containing small amounts of parasite DNA did not bind to the RAM1 Fab. Red cells with small amounts of DNA represents early stages, i.e. ring stage and trophoblasts, see FIG. 8.

Immunoblotting

Purified parasites were solubilized in 2% Triton X-100 by treatment with ultrasound 4×15 seconds on ice and incubation for 2 hours on ice before being mixed with sample buffer, heated to 100° C. for 10 minutes and subjected to SDS-PAGE in a MOPS-buffered 4-12% gradient gel (NOVEX)- Proteins were transferred electrophoretically to a PVDF membrane (Immobilon, Millipore) by wet blotting, blocked by drying the membrane and by incubation in 0,1% Tween20 and 0,2% I-Block (Tropix Cat. No. AI300) immediately before use. The blot was incubated for 3 hours with anti-malaria antibody RAM1, RAM2 or RAM3 produced as IgG1, washed 3×5 minutes with PBS supplemented with 0.1% Tween20 and 0,2% I-Block, and then incubated for 1 hour with alkaline phosphatase conjugated protein G (Pierce Cat no.32391). The membrane was washed 3 times as above. Finally, CSPD chemiluminescent substrate (Tropix Cat. no.CD100R) was added to the blot and light emission was detected with the Alpha Innotech FluorChem 8000 system. Hib-CP specific antibody was used as negative control in corresponding concentrations, see FIG. 7. RAM1 reacted with parasite proteins of relative molecular weights of approximately 51 and 53 kD, respectively. RAM2 reacted with parasite proteins of relative molecular weights of approximately 14 and 64 kD, respectively. RAM3 reacted with a parasite protein of approximately 64kD. Molecular weights in the same range have been observed with polyclonal antibodies from man and rabbit (Oeuvray et al, 1994; McColl et al, 1994). The background for the variation in molecular weights of the bands recognised by these two antibodies could be post-translational modification, proteolytic processing or the presence of subpopulations of molecules with distinct conformations. The latter possibility is tempting due to the alleged propensity of MSP-3 to obtain intra- or intermolecular coiled-coil conformations (McColl et al, 1994) later extended by Trucco et al (2001) to pertain to other merozoite specific proteins like MSP-1 and MSP-6. Such tertiary conformation will influence the electrophoretic mobility and could thus be responsible for the observed range of molecular weights. The band of 14 kD is believed to be due to proteolytic degradation. There have been no other reports of bands in this range.

Flow Cytometry

Purified schizonts were permeabilized and fixed by incubation in 32% ethanol for 30 minutes on ice. Parasites were then washed in PBS with 1% BSA, incubated over night with antibody (Fab-ΔpIII or IgG1), washed twice with PBS supplemented with 1% BSA and incubated for 30 minutes with FITC-conjugated goat anti-human Fab (Sigma F5512) diluted 1:25. Cells were analyzed in a Coulter EPICS-2 flow cytometer. Hib-CP specific antibody was used as control in corresponding concentrations. Fixed infected and fixed non-infected red cells were stained with propidium iodide and compared to enable gating on infected red cells, see FIG. 4.

Epitope Mapping

Our mapping of the epitopes relates to a previously used arbitrary division of MSP-3$_{194-257}$ into three peptides (Oeuvray et al. 1994) termed MSP-3a, MSP-3b and MSP-3c (Oeuvray et al. 1994). The biological relevance of the dissection of MSP-3$_{194-257}$ is that polyclonal antibodies directed to MSP-3b, corresponding to MSP-3$_{211}$.237 show a clear anti-parasitic effect in ADCI and in the mouse model (Badell et al. 2000).

Two peptides, MSP-3$_{190-217}$ and MSP-3$_{211-237}$, were synthesized and used in ELISA. RAM1 reacts predominantly with MSP-3$_{211-237}$. RAM2 reacts to the same extent with MSP-3$_{190-217}$ and MSP-3$_{211-237}$, and RAM3 reacted only weakly with these two peptides—see FIG. 9.

Additionally, the entire sequence MSP-3$_{194-257}$ was covered by synthesis of 34 sets of two peptides comprising contiguous amino acid sequences. The two peptides were linked by a proprietary linker substituting two amino acid residues on the location of the linker (PEPSCAN). Thus one single set of peptides covers a stretch of 31 amino acid residues with two amino acid residues replaced in positions 15 and 16 by the proprietary linker residues. The linked peptides were furthermore chemically coupled to the matrix to allow washing and repeated use. The overlap between two adjacent sets of peptides was two amino acid residues. This collection of peptides was examined for reactivity with RAM1 and RAM2 produced as IgG1. The result is presented in FIG. 10. RAM2 reacts with the amino-terminal, the middle and the carboxy-terminal part of the antigen but yields the highest reactivity with the middle part. RAM1 reacts only weakly with the peptides produced by this method. RAM3 was tested as Fab-ΔpIII in PEPSCAN without response.

The interpretation of the results is that RAM1 as well as RAM2 react with conformational, non-linear epitopes comprising amino acids residues being non-contiguously positioned in the antigen.

The epitope for RAM1 certainly comprises residues in the middle part. The contribution of residues in the amino-terminal and the carboxy-terminal part of the antigen is uncertain. The amino-terminal part of the antigen represented by the peptide MSP-3$_{190-217}$ comprises only heptad repeat sequence. The first residues of MSP-3$_{211-237}$ are part of a heptad repeat making it likely that the epitope for RAM1 is the c-terminal part of MSP-3$_{211-237}$. The region represented by residues 220-230, ILGWEFGGGVP (SEQ ID NO: 10), is outstanding by being present in MSP-3 as well as the other *Plasmodium falciparum* antigen MSP-6 (Trucco et al. 2001).

Based on the PEPSCAN results we conclude that RAM2 reacts with residues from all parts of the antigen but the major contribution is from the middle part.

Antibody Competition

The studies of binding to truncated antigens were supplemented with an antibody competition experiment. Fab fragments from clone RAM3 were produced in two versions. One version was fusion protein tagged with a truncated phage protein, ΔpIII, designated Fab-ΔpIII, and another version was normal Fab fragments without the ΔpIII tag. The ΔpIII-tag is readily detected using an antibody directed to the phage pIII protein. Thus Fab without ΔpIII can be present as competitor but only Fab-ΔpIII will be detected.

Figure 13:
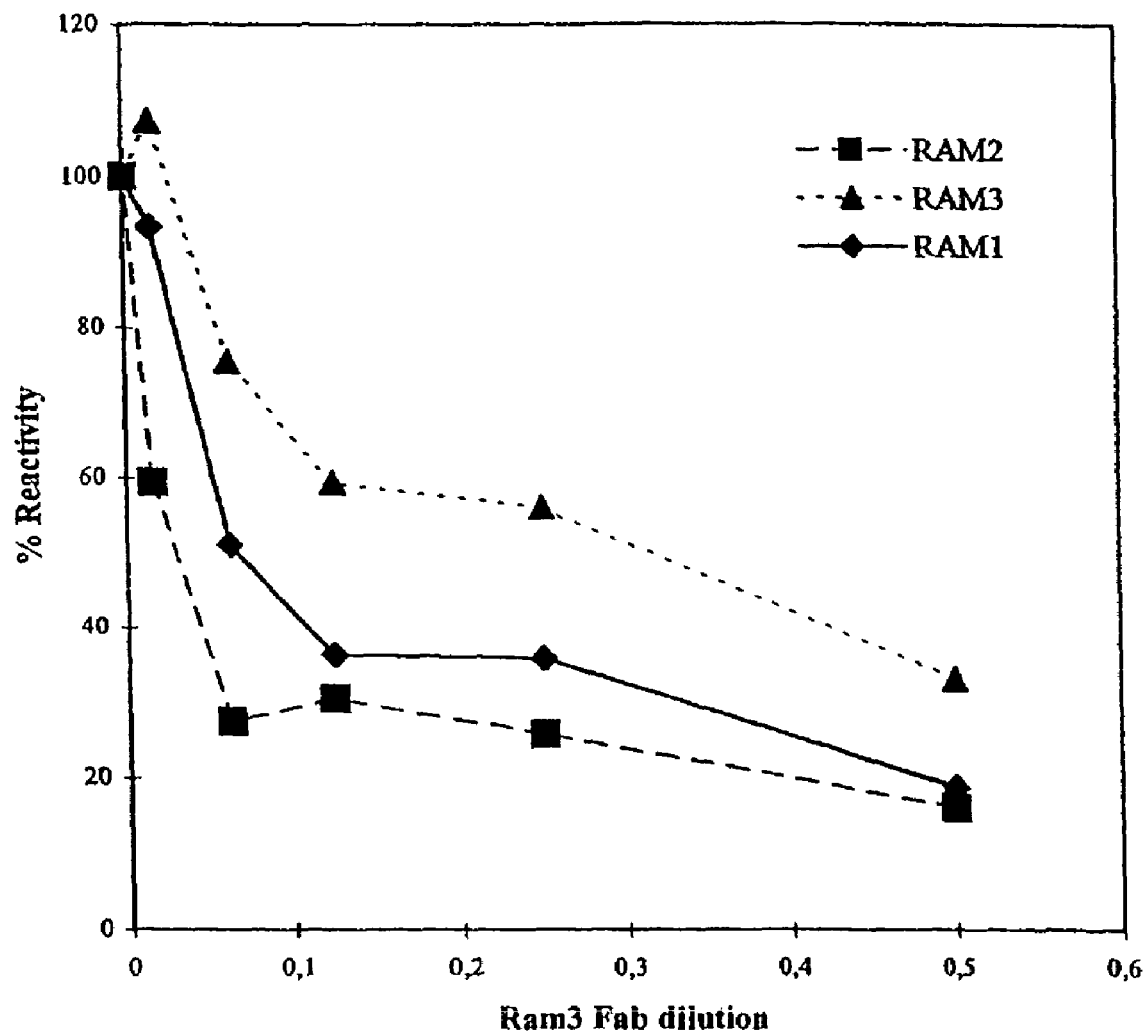

Amounts of RAM1, RAM2 and RAM3 Fab-ΔpIII yielding $OD_{405}$ of approximately 1 in ELISA on a coating of MSP-$3_{194-257}$ were used. The binding of the Fab-ΔpIII was then competed by the addition of increasing amounts of competitor, RAM3 without ΔpIII. FIG. 13 shows that Fab RAM3 is able to compete Fab-ΔpIII RAM1 to the same extent as it competes Fab-ΔpIII RAM2. This demonstrates that binding of the clones RAM1 and RAM2 is dependent on the epitope used by clone RAM3. The lower competitive effect of RAM3 on the binding of Fab-ΔpIII RAM3 could be explained by a higher affinity of RAM3 as compared to RAM1 and RAM2. The effect of this would be that the competitive effect of RAM3 towards RAM1 and RAM2 would be larger than towards RAM3 itself, see FIG. 13.

RAM3 was only reactive with the intact panning antigen and did not react with truncated versions. Furthermore RAM3 did not react with parasites in flow cytometry. However, the antibody competition experiment above shows that the epitopes for RAM1, RAM2 and RAM3 are closely dependent be it by direct steric hindrance due to overlap of epitopes or an effect of binding of RAM3 on the correct folding of the antigen.

We then tested if a malaria immune serum obtained from an individual living in a malaria-endemic area contains antibodies that will interfere with the binding of clone RAM1 to MSP-$3_{194-257}$. Clone RAM1 was produced as IgG1 and conjugated to FITC. The FITC-IgG1 was used in an assay identical to ELISA except for the detection of binding that was carried out by measurement of fluorescence in a microtiter plate based fluorometer. The amount of FITC-IgG1 was adjusted to give maximum effect of competition. Increasing amounts of competitor immune serum was added to individual well of the microtiter plate. A serum from a non-immune European donor was used as negative control. The malaria immune serum contained antibodies that significantly inhibited the binding of RAM1 IgG1. For technical details see below.

Method: Immune Serum Competition

MSP-$3_{194-257}$ coated ELISA plates (Maxisorb, NUNC 475515, Denmark) was incubated with serial dilutions of either immune serum (from a malaria immune individual) or control serum. After two hours the plate was washed 5 times with PBS 0,05% Tween 20. Then FITC-conjugated RAM1 IgG1 antibody was applied in a dilution yielding maximum reactivity. FITC-conjugation was performed as described by the manufacturer (Molecular Probes, cat. No. F-6434). The plate was incubated for one hour, then it was washed 5 times and subsequently relative fluorescence was determined using a Polarstar fluorescence reader (BMG, Germany).

We conclude that the epitope recognized by RAM1 on the antigen is indeed one that is also recognized by the immune system of a malaria immune individual. This substantiates the clinical in vivo relevance of the RAM1 clone and thus also of clones RAM2 and RAM3 as the three clones bind to very closely related epitopes, see FIG. 13.

Example 4

Production of Eukaryotic IgG1 and IgG3

Methods

Plasmids

The eukaryotic expression of intact antibodies was performed with the two plasmids, pLNOH2 and pLNOK (Norderhaug et al. 1997).

The structure of these plasmids and their relation to the assembled antibody is shown in FIG. 12 and FIG. 14.

Briefly, the V-regions of the plasmids are exchanged by cutting with BsmI in the 5' end and by cutting with HpaI or BsiWI or HindIII in the 3' end. Before ligation of vector and V region, the V regions of RAM1, RAM2 or RAM3 need to be cut with the same restriction enzymes as the vectors. VH regions are then ligated to pLNOH2 and VK regions are ligated to pLNOK. The constant region of pLNOH2 can be exchanged by cutting with BamHI and HindIII, isolating the vector part and introducing (by ligation) another constant region cut with the same enzymes.

pLNOH2 is a vector for expression of heavy chain V-region genes in combination with any constant fragment (Fc) gene. Two versions of the vector were used, one with the human γ1 constant fragment gene (allotype G1m(a, z)) and another with the human γ3 gene (allotype G3m(b)), to enable recombinant expression of the two isotypic variants of the antibody.

pLNOK is a vector for expression of kappa light chain V-region genes in combination with the kappa constant domain gene. The common features of the two vectors are briefly described below. The CMV promoter is situated 5' to a gene casette containing the leader region of murine immunoglobulin genes, the V-region gene inserted between restriction sites BsmI and BsiWI followed by an intron and the entire genomic C-region with a poly-A signal in the 3' end. The intron comprises splice acceptor and splice donor signals for correct processing of the mRNA. Non-abundant restriction sites flank the V-regions genes and are introduced by PCR into the gene fragments to be cloned. Additional features of the vectors are, ampicillin resistance marker for selection in *E. coli*, f1-origin of replication, Neomycin resistance selection marker for stable expression and the SV40 origin of replication to allow transient expression.

In order to produce a complete antibody, the plasmids (both pLNOH2 and pLNOK) are cotransfected into CHO cells. The V and C regions are assembled by mRNA splicing. When co-transfected in one cell, e.g. a CHO cell, the cell produces complete and correctly assembled antibodies.

As an alternative, the genes can be assembled into one vector which thus harbours the VH, CH, VL and CL domains.

PCR of Antibody Genes

Two separate PCR amplifications were performed for each antibody, one for the heavy chain and one for the light chain. The templates were pFAB73H+RAM1, pFAB73H+RAM2 and pFAB73H+RAM3. For amplification of the RAM1 heavy chain V-region fragment one primer designated EuHVH-1 was based on the 5' sequence of RAM1 $V_H$ (indicated in bold) and further contained the recognition sequence of restriction enzyme BsmI (indicated by underlining and italics):

EuHVH-1:
(SEQ ID NO: 79)
5' ggt <u>gtg cat tc</u>c cag gt<u>n</u> caa ttg gt<u>r</u> ca<u>r</u> tc<u>y</u> g 3'

Ambiguous bases (highlighted by underlining) were introduced to make this primer compatible with the primer set published by Dziegiel et al. 1995.

The other primer, EUHJH, was complementary to the 3' sequence of RAM1 $V_H$ (indicated in bold) and contained the additional sequence of the restriction enzymes HindIII, BsiWI and HpaI (indicated by underlining) and the complementary sequence to the splice donor sequence 5' AGGT-GAGT 3' (indicated in capital letters):

EuHJH:
(SEQ ID NO: 80)
5' gt cc<u>a agc ttc gta cgt ta</u>A CTC ACC Tga rga gac rgt gac c 3'

HindIII    BsiWI    HpaI

For amplification of the RAM1 light chain V-region gene fragment two primers designated EuHVKuniversal and EuHJK-14a were used. EUHVK universal was made compatible with the primer set published by Dziegiel et al. 1995 by taking advantage of the invariant 5' sequence of all kappa chain genes derived from this primer set (indicated by double underlining).

The primer further contained the recognition sequence of restriction enzyme BsmI (indicated by bold) and part of the pelB leader sequence found in the phage display vector (indicated by underlining):

EuHVKuniversal:
(SEQ ID NO: 81)
5' <u>ttg tta tta ctc gcg gcc cag ccg gtg</u> cat tcc <u>gac atc</u> 3'

|---------- PelB leader seq. -----|| BsmI    |  |-> Vκ

EuHJK-14a was based on the same principle as EuHJH shown above, complementarity to the 3' sequence of RAM1 $V_K$ (indicated in bold), the sequence of the restriction enzymes HindIII, BsiWI and HpaI (indicated by underlining) and the sequence complementary to the splice donor sequence 5' A CTC ACG T 3' (indicated in capital letters):

EuHJK-14a:
(SEQ ID NO: 82)
g tcc <u>aag ctt cgt acg tta ac</u>A CTC ACG Ttt gat ctc cag cct gg

For amplification of the RAM2 heavy chain V-region fragment one primer designated EuHVH-2 was based on the 5' sequence of RAM2 $V_H$ (indicated in bold) and further contained the recognition sequence of restriction enzyme BsmI (indicated by underlining and italics):

EuHVH-2:
(SEQ ID NO: 83)
ggt *<u>gtg cat tc</u>*c cag gtg caa ttg cag gag tc<u>s</u> g

Ambiguous bases (highlighted by underlining) were introduced to make this primer compatible with the primer set published by Dziegiel et al. 1995.

The other primer, EuHJH is described above.

For amplification of the RAM2 light chain V-region gene fragment two primers designated EuHVKuniversal and EuHJK-15 were used. EuHVKuniversal is described above.

EuHJK-15 was based on the same principle as EuHJK-14a shown above, complementarity to the 3' sequence of RAM2 V$_K$ (indicated in bold), the sequence of the restriction enzymes HindIII, BsiWI and HpaI (indicated by underlining) and the sequence complementary to the splice donor sequence 5' A CTC ACG T 3' (indicated in capital letters):

EuHJK-15:
(SEQ ID NO: 84)
g tcc <u>aag ctt cgt acg tta ac</u>A CTC ACG Ttt gat ctc cac cc

For amplification of the RAM3 heavy chain V-region fragment the same primers were used as for RAM1 (see above)

For amplification of the RAM3 light chain V-region gene fragment two primers designated EuHVKuniversal and EuHJK-8 were used. EuHVKuniversal is described above.

EuHJK-8 was based on the same principle as EuHJK-14a shown above, complementarity to the 3' sequence of RAM3V$_K$ (indicated in bold), the sequence of the restriction enzymes HindIII, BsiWI and HpaI (indicated by underlining) and the sequence complementary to the splice donor sequence 5' A CTC ACG T 3' (indicated in capital letters)

EuHJK-8:
(SEQ ID NO: 85)
gt cc<u>a agc ttc gta cgt taa ctt</u> ctA CTC ACG Ttt gat ytc cac ctt gg

The PCR were performed using Gene Amp PCR System 9600, AmpliTaq Gold and the supplied buffers. Primers were used in a final concentration of 0,2 µM. The PCR cycling included the following steps: 10 min. at 95° C. (hot start, activation of AmpliTaq), 14 cycles of 94° C. for 30 seconds, 40° C. for 30 seconds and 72° C. for 30 seconds and finally one cycle at 72° C. for 10 min.

Amplification products of the expected sizes were isolated by gel electrophoresis, purified with Gene Clean (Bio 101, Inc., Calif, USA) and ligated into pGem-T Easy (Promega, USA) according to the manufacturer.

Ligations were used to transform electrocompetent XL-1 blue (Stratagene). Subsequently the cells were plated on LB containing X-gal and IPTG as described in Sambrook et al. 1989. White clones were sequenced using Big dye (Applied Biosystems, USA) and the primers SP-6 and T7 as recommended by the manufacturer. The sequence reactions were applied to ABI PRISM Sequencer 310 (Perkin 5 Elmer, USA).

For each heavy and light chain a clone was selected that was either identical to the template or that did not alter the deduced amino acid sequence.

The selected clones were digested with BsmI and BsiWI or with BsmI and HindIII. The fragments were then ligated into the appropriate vector digested with the same enzymes.

Cell Line

CHO cells were used as eukaryotic host cells for stable expression of intact antibodies.

Transfection and Expression

Cells were grown to 50-80% confluency in Ham's F-12 Medium supplemented with 10% inactivated Foetal Bovine Serum (Life Technologies). Cells were then transfected with Lipofectamine (Life Technologies) according to the procedures of the manufacturers. The following day transfected cells were transferred to microtiter plates to select clones by limiting dilution. After approximately 14 days wells containing single cell colonies were tested for production of anti-MSP-3 antibodies in ELISA. Cells from approx. 20 wells giving the highest response in the ELISA assay were transferred to new wells in a 24 well microtiter plate, grown to confluence, transferred to new wells in a 6 well microtiter plate, grown to confluence and finally transferred to two 25 cm$^2$ TC flasks. Cells in one flask were grown to confluence and sebsequently frozen. Cells in the second flask were grown for approx. 4 weeks whereupon the supernatant was tested for production of anti-MSP-3 antibodies in ELISA. The clone giving the highest response in the ELISA assay was used for a second round of limited dilution. The clone from the second round of limited dilution giving the highest response in the ELISA assay was grown to an appropriate number of cell to be used for 1) freezing and 2) expression of antibody. For expression cells were plated to approx. 10% confluence in triple TC flasks (NUNC, Denmark) and grown for approx. 4 weeks. The supernatant was centrifuged 20,000×g for 30 minutes before use in subsequent assays to remove cellular debris.

Immunochemistry

The composition of human antibodies in the supernatant from the cell culture was examined by capture ELISA. Human antibodies were captured on a coating of goat anti-human Fab fragments (Sigma I5260) and detected with mouse anti-human IgG1(Zymed 05-3600) or IgG3 (Zymed 05-3300), respectively, followed by rabbit anti-mouse conjugated to horse radish peroxidase (DAKO P260). ELISA for reactivity with specific antigen was performed as described under Example 3. Furthermore, the IgG1version of RAM1, RAM2 and RAM3 were used for Western blotting and RAM1 IgG1 was used for flow cytometry.

Capture ELISA for Quantitation of IgG

Capturing of recombinant IgG was done with goat anti-human IgG specific for the Fc-portion 1:5,000 (Sigma I2136), detection was performed with alkaline phosphatase conjugated goat anti-human kappa chain 1:10,000 (Sigma A3813). Purified human recombinant anti-D IgG1, kappa (751 pg/mL) and IgG3, kappa (135 µg/mL), respectively, were used as standards. Standard IgG had identical allotypes as malaria antibodies. ELISA procedures and buffers were as described in Dziegiel et al. 1991.

Results

The V$_H$ and V$_K$ genes derived from the anti-MSP-3 antibodies were combined with constant domain genes in plasmids pLNOH2 and pLNOK, respectively. Two different versions of the heavy chain vector, pLNOH2, were used, one version containing the γ1 constant domain gene and the other containing the γ3 constant domain gene. These two vectors were used for production of an IgG1 version as well as an IgG3 version of the anti-MSP-3 antibodies. The composition of the antibodies was investigated by immunochemistry in ELISA. The specificity of the IgG1 and IgG3 versions was tested with ELISA technique.

Example 5

Purification of Eukaryotic IgG1 and IgG3

After ammonium sulfate precipitation (70%) of cleared culture supernatant, pelleted proteins were resuspended in water. Buffer exchange to 70 mM Sodium acetate pH 5.0 was performed by dialysis. Recombinant IgG was purified using DEAE Sepharose FF (Pharmacia BioTech) followed by applying the flow through to an ABx column (Baker Bond). The buffer was changed to 50 mM Bicine pH 8.5 and the IgG eluted with a gradient of 50 mM Bicine supplemented with 0.5 M NaCl pH 8.5. If necessary antibody containing fractions from the Abx column are precipitated by ammonium sulphate as above and applied to the gel filtration column (Superdex200). The purity was checked by gel chromatography using Superdex200 and by SDS-PAGE followed by silver staining.

Example 6

Characterization of the Biological Activity of Recombinant Antibodies by ADCI and Other Functional and Parasitological Tests These assays reflect the clinical status of protection. The ADCI reflects the capacity of individual IgG to inhibit *P. falciparum* growth in vitro by cooperation with human blood monocytes as described in Bouharoun-Tayoun et al. (1995). The *P. falciparum* merozoite phagocytosis assay in the presence of antibody has been checked among the 200 inhabitants from Dielmo where it closely reflects the clinical status of the inhabitants.

ADCI and phagocytosis assays may be performed with the selected antibodies and human monocytes following standardized procedures.

For antibodies expressed with Fc portions in eukaryotic cells, the classical ADCI assay may be used, as described by Shi et al. 1999.

The parasites are cultured in the presence of recombinant antibodies and healthy donor derived monocytes. In order to determine the specific growth inhibition (SGI) of ADCI described below, the appropriate controls are included.

which is a vital dye that is converted to ethidium by metabolically active cells. Ethidium interacts with the parasite derived DNA in infected cells and thereby allows discrimination between infected and non-infected erythrocytes by flowcytometry (Shi et al., 1999).

A flow cytometry based phagocytosis assay developed by Kumaratilake and Ferrante (2000) may be used to determine the opsonization and phagocytosis mediating abilities of the produced antibodies. This assay explores the ability of neutrophils to quench FITC-conjugated merozoites. This assay is adapted to detect phagocytosis by other leukocytes (such as monocytes) as an effect of antibody opsonization (Kushmith & Druilhe, 1983.

Furthermore, the antibodies produced may be tested in vivo in the mouse model developed by Badell et al (1995) & (2000). This model is based on the possibility of obtaining a sustained *P. falciparum* growth in immunocompromised mice reconstituted with human erythrocytes as well as human monocytes.

Studies of this nature are described below. The antimalarial biological activity of RAM1 IgG1 and RAM1 IgG3 recombinant antibodies was assessed using both in vitro and in vivo assays previously established as reflecting immune mechanisms of defense mediating protection against *P. falciparum* in human beings (Druilhe et al., 1995; Bouharoun-Tayoun et al., 1995; Badell et al., 1995).

In Vitro ADCI Studies

In vitro studies were aimed at measuring the monocyte-dependant antibody-mediated mechanism of cooperation named ADCI (Antibody-Dependant Cellular Inhibition of *P. falciparum*) previously found to correlate closely with the status of protection obtained by passive transfer of African human IgG in to *P. falciparum* infected Thai receivers (Sabchareon et al., 1991; Bouharou-Tayoun et al., 1990), and a mechanism that has been at the origin of the identification of the Merozoite Surface Protein-3 (MSP-3) molecule on the merozoite surface and the identification of the MSP-3. b epitope within the C-terminus region of the antigen (Oeuvray et al., 1994). RAM1 IgG1 and RAM1 IgG3 were studied in the ADCI assay alongside with positive controls, namely the adult African IgG pool which proved effective upon passive transfer in *P. falciparum* infected subjects, an affinity-purified antibody against the MSP-3. b peptide, and an anti-MSP-3 C-terminus antibody obtained by immuno-purification of the same African IgG pool upon the C-terminus recombinant antigen expressed in the His-tail vector. Negative controls $$SGI \text{ of } ADCI = 100 \times \left(1 - \frac{\left(\frac{\% \text{ mean parasitemia with test } IgG \text{ and monocytes}}{\% \text{ mean parasitemia with test } IgG}\right)}{\left(\frac{\% \text{ mean parasitemia with control } IgG \text{ and monocytes}}{\% \text{ mean parasitemia with control } IgG}\right)}\right)$$

Monocytes are isolated by the lymfoprep method, and by adhesion to autologous plasma coated plastic tissue culture Petri dishes (Nunc).

The malaria parasite may be grown as described by Trager and Jensen 1976 in 96 well tissue culture plates. The effect of IgG's and monocytes is determined in 48-hour cultures with an initial parasitemia of 0,5%. For tests with monocytes these are activated by rhIFN-γ and added to each well.

After 48 hours the parasitemias are assessed by flow cytometry as described by van der Heyde et al. (1995). The cultures are after 48 hours incubated with hydroethidine included total European IgG from individuals who have not been travelling in malaria endemic areas, antibodies absorbed from African subjects upon the RESA (Ring Infected Surface Antigen) and the Merozoite Surface Protein-1 (MSP-1) antigen. The study was repeated 3 times using 3 different normal blood monocytes donors and using either the Ouganda Palo Alto strain or the 3D7 clone derived from the NF54 strain of *P. falciparum*.

Positive Control IgG (PIAG) was purified from a serum pool obtained from African adults living permanently in a rural area of Ivory Coast where malaria is holoendemic. They were selected on clinical and epidemiological grounds (Sabchareon et al., 1991). They experienced numerous malaria attacks in childhood and were free of symptoms and heavy parasitemia and thus regarded as immune individuals (Bouharoun-Tayoun et al., 1990). The IgG was extracted by ion-exchange chromatography on DEAE-sephadex (Pharmacia). The IgG containing fractions were pooled, protein content and antibody level were determined by Bicinchoninic acid protein determination reagents (Sigma) and IFA respectively. The protein content was found to be 16.2 mg/ml and IFA endpoint titre of the preparation was 1:52,000. Final concentration of 2 mg/ml (10% of the serum concentration, 650 IFA titre) was used in ADCI assay (Bouharoun-Tayoun et al., 1990).

Negative Control IgG ( NIG) was similarly prepared as above using a commercially available pool from more than 1,000 healthy French blood donors (Biotransfusion CRTS, Lille, France). The IFA test was negative at 1:200.

The indirect immunofluorescent antibody (IFA) test was performed as reported earlier (Bouharoun-Tayoun et al., 1990). Briefly, a thin film of *P. falciparum* 3D7 schizont-infected RBCs was incubated with serial dilutions, starting from 1:200 of the recombinant antibodies or IgGs in PBS (pH 7.4) for 30 min at 37° C. inside humid chamber. Alexa fluor conjugated goat anti-human IgGs (Molecular Probe, USA) at 1:300 dilution in PBS was used to detect the bound immunoglobulins. The endpoint titre was the highest dilution of the antibodies which produced visible specific immunofluorescence.

Parasite culture: *P. falciparum* 3D7 clone from NF54 and PaloAlto were cultured in RPMI 1640 medium supplemented with hypoxanthine, 0.5% albumax (Gibco BRL), sodium bicarbonate, HEPES, penicillin and streptomycin in $AB^+Rh^-$ RBCs. Parasites were synchronized by alternate sorbital treatment and plasmagel floatation. On the day of ADCI assay, parasites were prepared from plasmagel floatation.

ADCI assay: Two *P. falciparum* strains, the 3D7 clone derived from NF54 and the PaloAlto strain were used. ADCI assay was performed as described (Bouharoun-Tayoun et al., 1990) with some modifications. Normal monocytes were obtained from healthy donors without exposure to malaria infection and separated from peripheral blood mononuclear cells by adherence on 96 wells flat-bottom culture plates (TPP, Switzerland). Donor's plasma was coated on the plate for better attachment. Mononuclear cells which will contain $2 \times 10^5$ monocytes were distributed into each well. Well synchronized *P. falciparum* schizont stage adjusted to 0.5% parasitemia with final haematocrit of 2% were added to each well. The anti-MSP3 RAM1 recombinant antibodies were added at three different concentrations in respect to IFA titre of 200, 500 and 1000, to each well with and without monocytes. Final volume in each well was adjusted to 100 μl. In addition to the control recombinant IgG1 and IgG3, the following control were run simultaneously in each plate: a) culture without monocytes, b) culture with monocytes, c) culture with NIG, d) culture with monocytes and NIG, e) culture with PIAG, f) culture with monocytes and PIAG. 50 μl of RPMI containing 0.5% albumax, penicillin and streptomycin were added to each well at 48h and 72 h. The assay lasted 96 h and at the end of the assay parasitemia was determined by both microscopic counting of more than 50,000 RBCs on Giemsa stained film and by FACS after staining with hydroethidine.

The specific growth inhibitory index (SGI) which takes into consideration the possible inhibition induced by monocytes or antibodies by themselves, was calculated as described above.

Determination of parasitemia was undertaken as reported by van der Heyde et al. (1995). Parasite pellet from each ADCI well was incubated with freshly diluted 200 μl of hydroethidine 50 μg/ml in PBS pH 7.4 for 20 min at 37° C. in the dark. After incubation, the parasite pellets were washed 2 times with PBS and resuspended in a final volume of 700 μl in the fluorescence-activated cell sorter (FACS) tubes. Data acquisition and analysis were performed on FACScalibur (Becton-Dickinson, San Jose, Calif.) . The detectors of forward and side scatter were set in logarithmic mode and 100,000 cells were counted. Both infected and uninfected RBCs were gated in the analysis and the percentage of parasitemia was determined by the use of Cellquest-Pro program (Becton-Dickinson). Parasitised red blood cells were distinguishable from monocytes on the basis of size and intensity of fluorescence. Uninfected human $AB^+ Rh^-$ similarly treated with hydroethidine was assigned to region 1 and infected RBCs to region 2. The percentage of metabolizing or healthy parasites was similar to that obtained by microscopy.

TABLE II

Specific Growth Inhibitory Index (SGI) of the recombinant human RAM-1 IgG1 and IgG3 subclasses against MSP3 antigen.

| Antibody | μg/ml in ADCI | IFAT in ADCI | SGI % | DI % |
|---|---|---|---|---|
| IgG1 anti-MSP3 | 40 | 50 | 72(±7) | 4(±8) |
|  | 20 | 10 | 66(±3) | 0(±0) |
| Control IgG1 | 40 | 0 | 2(±3) | 9(±16) |
| IgG3 anti-MSP3 | 15 | 50 | 49(±4) | 11(±14) |
|  | 3 | 10 | 23(±17) | 9(±6) |
| Control IgG3 | 15 | 0 | 11(±4) | 9(±12) |

IFAT = endpoint titre of indirect immunofluorescence with *P. falciparum* clone 3D7 mature schizonts infected RBCs as described;
SGI % were the mean and SD in parenthesis of 3 different ADCI assays utilizing *P. falciparum* clone 3D7;
DI % = percentage of direct inhibitory effect of antibodies on *P. falciparum* culture.

The 3 independent assays yielded the same results both upon the Palo Alto strain and the 3D7 clone with a stronger ADCI effect obtained with RAM1 IgG1 than RAM1 IgG3 (see Table II.). This set of in vitro studies clearly establishes that RAM1 which binds to the MSP-3. b epitope can exert a parasite killing effect upon the main malaria species responsible for the majority of deaths attributable to malaria, *P. falciparum*, in a strong and efficient manner, i.e. at least as strong as antibodies from Africans who have reached a state of protection which can be demonstrated by passive transfer of their immunoglobulins into naive infected recipients. This biological effect was not only strong, but also obtained at very low concentrations of the recombinant antibody, i.e. at concentrations which correspond to only 5% of the concentration of the polyclonal anti-MSP-3 antibodies in the African IgG protective pool. As was the case with positive controls mentioned above, no direct effect upon merozoite invasion into red blood cells was recorded with RAM1 antibodies. Hence, the RAM1 recombinant antibodies reproduced all the observations previously made with natural, polyclonal, protective antibodies.

In Vivo Studies in Immunocompromised Mice

As described above, in vivo studies may be performed in the mouse model described by Badell et al. (1995, 2000). The in vivo studies described here were performed using the newly developed immunocompromised mouse model, in which human red blood cells can be grafted and a *P. falciparum* parasitemia obtained for durations of up to 4 and a half months. This model is essentially an improvement over the initial descriptions made by Badell et al. (1995) (see below) and correspond essentially to the protocol described in Badell et al. (1995) (see below) and also Moreno et al. (2000) (see below). One of the major advantages of this *P. falciparum* animal model over primate models is that parasitemia remains persistent at chronic level, i.e. at densities which are similar to those obtained in human subjects. This contrasts with primate models where parasitemia is fast rising and where the animals need to be treated within a few days, otherwise they will die of infection. Therefore, in the new mouse model, serial new mouse model, serial experiments can be performed over several days or weeks and the effects of various components investigated as of control antibodies can be sequentially injected in the same animal which therefore constitute its own control.

Mice: Male Beige/XID/Nude (BXN) mice of 6-8 weeks old were used. They were purchased from Charles River, USA, kept and manipulated in pathogens free conditions (sterile isolators and laminar flow hoods).

Immunomodulation of innate immunity in BXN mice: The number of macrophages and polymorphonuclears neutrophils (PMN) were respectively reduced by intraperitoneal injection (i.p.) of 0,2 ml liposomes containing $Cl_2MDP$ every 4-5 days (24) and of 300 µg of NIMP-R14 monoclonal anti-PMN antibodies. The hybridoma producing NIMP-R14 MAb was a gift from Dr. Malcolm Strath.

Parasites and culture: The *P. falciparum* African strains 3D7 and Palo Alto were used. Parasite blood stages were cultivated in RPMI 1640 (Gibco BRL, Grand Island, N.Y.) supplemented with hypoxanthine 30 mM (RPMI-Hypox) and 0.5% Albumax (Gibco BRL, Grand Island, N.Y.) and synchronized by repeated sorbitol treatment and by flotation on plasmagel (Plasmagel, BELLON, Neuilly-Sur-Seine, France).

Graft of human red blood cells (HuRBC) into the mice: Human blood from AB+ blood donors with no history of malaria was collected by venipuncture in either, CPD anticoagulant (MacoPharma, Tourcoing-France) or sodium heparin (Sanofi Winthrop, Gentilly-France) and spun at 600 g, 10 min. at 20° C. After elimination of the white cells (buffy coat) packed red blood cells were suspended in Saline-Adenine-Glucose SAGM (MacoPharma, Tourcoing-France), and kept at 4° C. for a maximum of 30 days. Before use, HuRBC were washed 3 times at 600 g with RPMI-1640 (Gibco BRL, Grand Island, N.Y.) supplemented with hypoxanthine (RPMI-Hypox). 2 ml of washed HuRBC at 50% hematocrit were injected i.p every 3-4 days to each mouse Graft of human parasitised red blood cells (P.f.-HuRBC) into the mice: Highly synchronized ring forms (parasitaemia between 1-3%) were washed 5 min. at 400 g in RPMI-Hypoxanthine. 2 ml of this suspension at 50% hematocrit in RPMI-Hypoxanthine were injected i.p into each mice, followed by repeated injection of non-infected hu-RBC every 3-4 days as mentioned above. Daily thin blood films drawn from the tail vein were used to monitor the development of the parasitaemia.

Passive Transfer in P.f.-HuRBC-BXN Mouse Model

Human peripheral blood mononuclear cells (hu-PBMC): Similar criteria as mentioned above were used to collected blood. The total hu-PBMC cells were isolated by ficoll-hypaque and washed twice with Hank's balanced salt solution (HBSS) buffered with 35 mM of Hepes (Gibco, BRL). HuMN were enriched by adherence to plastics. Attached monocytes were removed by cells scrapper and the number of monocytes determinate by non-specific esterase (NSE) staining (mean 70%) and the viability estimated by trypan's blue (mean 85%) Either $3 \times 10^7$ hu-PBMC or $3 \times 10^6$ purified HUMN were engrafted in each mouse.

Control IgG preparations: A pool of hyper-immune African IgG (PIAG) was purified from 200 pooled sera from protected individuals living in the Ivory Coast as described by Bouharoun-Tayoun et al. These subjects are referred to as protected since they have reached a state of clinical immunity to malaria. A pool of control IgG from normal French blood donors with no history of malaria was prepared following the same procedure. For passive transfer experiments, total HI-IgG were injected at a dose of 200 mg/kg (6 mg/mouse).

Sampling of mice at regular intervals after IgG transfer and determination of antibody concentrations by ELISA showed that catabolism led to a progressive disappearance of the transferred antibodies within 7 days.

Preparation of Anti-MSP3/b and Anti-RESA antibodies: The IgG were loaded on a Sulfolink column (Pierce, Rockford, Ill.) that was coated with MSP3/b-Cys peptide according to manufacturer's instruction, and run in a closed circuit for 24 hours at 1 ml/10 min rate. After washing with PBS for 18 hours, the specific IgG were eluted from the column with glycine 0.2M, pH2.5 (Sigma, St-Louis, Mo.). 1 ml fractions were collected and pH adjusted to 5.0 with 2M Tris in NaOH (Sigma, St-Louis, Mo.). BSA at 2 mg/ml was added to conserve the biological activity of the antibodies (Boehringer, Manheim). The reactivity of each fraction against the peptide was monitored by ELISA, as previously described, and those containing specific anti-MSP3/b antibodies were pooled and concentrated to 500 µl with centricon30 (Millipore, Bedford, Mass.). To avoid degradation of those antibodies, 1% of bovine albumin (Sigma, St Louis, USA) is added immediately after concentration. Then, the antibodies were dialyzed against PBS and RPMI 1640, filtered and stored at 4° C. until used. Anti-RESA antibodies were obtained following the same experimental procedure as described above. The peptide sequence used was: $(H-(EENVEHDA)_2-(EENV)_2-OH)$ (SEQ ID NO: 86)

For passive transfer experiments, the amount of immunopurified anti MSP3 or RESA antibodies was adjusted by IFAT titters and 250 µl/mice of the solution was added each time.

Anti-RAM1 IgG1 and IgG3 antibodies and control anti-Rh D antibody, were injected at a rate of 1.2 mg per Kilogramme of bodyweight, via IP route Immunoassays: Titration of purified antibodies on native protein: The titer of each concentrated antibody preparation was determined by incubating serial doubling dilutions on air-dried thin blood smears of the NF54 strain. After it, an anti-human FITC-labeled secondary antibody (Biosys, France) diluted 1/200 in PBS and Evans blue 1/5000 (Sigma, St-Louis, Mo.) was added. The titer is the highest dilution giving a positive response. MSP3 antibodies were titered on slides prepared with cultures containing a high percentage of very mature schizonts. For RESA antibodies, cultures with a high percentage of ring forms were used.

Western Blot: The specificity of the antibodies was also tested on western blot of parasite extract on SDS-page separation and transfer on nitro-cellulose paper of NF-54 strain after plasmagel flotation. The antibodies were diluted 1/100 and revealed with a secondary anti-human IgG PAL-labeled diluted 1/7500 (Promega, Madison, Wis., USA) using the NBT/BCIP system for the color reaction (Promega, Madison, Wiss., USA).

RESULTS

In *P. falciparum* BXN mice, the inoculation of normal blood monocytes did not alter significantly the course of parasitemia (see FIGS. 15 and 17). Similarly, the injection of control anti-RESA antibodies had no effect whatsoever, either alone or following inoculation of normal human monocytes (FIG. 15). Similarly, anti-MSP-1 antibodies were found to have no significant effect upon the course of parasitemia. Conversely, the inoculation of affinity-purified human anti-MSP-3 antibodies, either obtained by affinity-purification on the MSP-3.b synthetic peptide or obtained by affinity-purification on the recombinant C-terminus MSP-3 recombinant cleared the parasitemia in BXN mice as fast as drug treatment by the fastest active antimalarial drugs, such as chloroquine or artemisin (FIG. 16). It is noteworthy that in those experiments, anti-MSP-3 antibodies affinity purified on either the synthetic peptide or the recombinant antigen had a faster and more profound effect than total protected African adults IgG in which anti-MSP-3 antibodies were at the same concentration as the purified ones (FIG. 18). In animals receiving either recombinant RAM1 IgG1 or recombinant RAM1 IgG3 antibodies, the inoculation of normal blood monocytes alone had no significant effect upon the course of parasitemia (a significant example is shown in FIG. 19). In the same animals, the subsequent inoculation of the negative control anti-body, a recombinant antibody directed to the Rhesus D antigen, had no significant effect (there was a slight decrease over the first day which was followed by a re-increase in parasitemia to the initlal level (FIG. 19) In contrast, the final inoculation of recombinant antibody RAM1 IgG1resulted in the fast and total clearance of the $P.\ falciparum$ circulating parasitemia in those humanised mice (FIG. 19). Similarly, the inoculation of recombinant antibody RAM1 IgG3 also induced a profound decrease in parasitemia which, however, was not total. Therefore, the same difference between recombinant RAM1 IgG1 and RAM1 IgG3 observed under in vitro conditions was also observed under in vivo conditions in humanized immunocompromised mice. It is noteworthy that the recombinant RAM1 IgG1 induces a decrease in parasitemia of the same intensity as polyclonal affinity-purified human antibodies to MSP-3.b and that the clearance of parasitemia was total, i.e. resulted in an absence of parasitemia over 96 hours in similar manner as affinity-purified polyclonal antibody to MSP-3 and in contrast to total protective African IgG.

Therefore, both in vitro and in vivo results produced convergent data to demonstrate the strong biological effect of recombinant RAM1 IgG1 antibody and its ability to mediate $P.\ falciparum$ killing in cooperation with normal blood monocytes in the ADCI effect which is at the origin of the discovery of MSP-3 target antigen.

DISCUSSION

The strategy followed for construction of the library was to attempt to clone as many antibody genes as possible from the 13 malaria immune individuals from Senegal, Africa. This presents some important advantages as opposed to the strategy of trying to cover the entire repertoire from only a single or a few individuals. Immunity to malaria is supposed to be one of the major selective pressures exerted to mankind in malaria endemic areas during evolution. It has been postulated (Antibody repertoires and pathogen recognition: the role of germline diversity and somatic hypermutation. PhD thesis by Mihaela Oprea, 1999, Santa Fe Institute) that an important factor in successful development of malaria immunity in an individual is the possession of a limited number of selected heavy chain genes, e.g. $10^5$, encoding broadly reactive antibodies. The role of such antibodies would be to interact with all important and harmful antigens in order to initiate an antibody response progressively leading to a higher quality response in one and the same individual. The higher quality is manifested in specificity, affinity and protective biological effects. By cloning $5\times10^7$ different heavy chain genes from 13 individuals the library on the average contains $4\times10^6$ different genes from each individual thus enhancing the likelihood of having cloned at least one copy of each of the $10^5$ important genes. The other strategy, relying on cloning a similar size library from one individual would at the most result in the cloning of one full repertoire of the $10^5$ basic repertoire of antibodies.

The antibodies provided here provide a novel strategy for prevention and treatment of malaria. If ordinary ADCC and phagocytosis were the sole mechanisms at play a high initial parasitemia would lead to a large consumption of immunoglobulin and consequently to a lower fractional reduction in parasitemia. Therefore it is believed that the antibody-merozoite complex stimulates the monocyte in a contact-dependent manner to secrete the effector substance(s) responsible for a subsequent non-contact-dependent inhibition of the growth of the parasite. Candidate molecules for the inhibitory substances are nitrogen oxide and TNF-$\alpha$. Thus the high initial concentration of parasites is assumed to induce a high and efficient concentration of anti-parasitic substances leading to a high reduction rate.

Exploitation of the naturally occurring anti-parasitic host/pathogen interaction (premunition, ADCI) is a novel way of developing a therapeutical anti-parasitic activity. The immunological mechanism that is exploited by these antibodies is the co-operation between the three components, merozoite—antibody—monocyte leading to inhibition of parasite growth (ADCI) through secretion of TNF-$\alpha$ and other substances, e.g. nitrogen oxide species and oxygen radicals. This mechanism of protection requires only a minority of the merozoites to interact physically with antibody and monocyte. Indeed, the majority of the parasites are only exposed to the substances released as a consequence of the bystander merozoite-antibody-monocyte interaction.

The use of recombinant antibodies ensures that the appropriate isotype can be used. This would not be the case if antibodies purified from infected individuals were used, e.g. for the ADCI mechanism, IgG1 and IgG3 isotypes are important.

The sub-populations of target antigen-escape mutants will not have a direct survival advantage compared to the wild-type and therefore do not influence the general level of anti-parasitic activity. Only in the situation where the number of wild-type parasites had been reduced dramatically would the monocyte stimulus drop. A minority of parasites possessing wild-type target-antigen would be sufficient for stimulating the monocyte to release substances with anti-parasitic activity. Therefore, resistance to this anti-parasitic mechanism is a minor concern. Studies of the conservation of the relevant domains of the target molecule MSP-3, have indeed s confirmed that immunological selection pressure seemingly is absent as a consequence of the above-mentioned immunological mechanism (Stricker et al 1999).

Insensitivity of the parasites to the action of the substances released by monocytes and other effector cells does not seem to be a problem. This is substantiated by the clinical observation of life-long persistence of the so-called premunition once it has been obtained and is maintained by continuous exposure to the parasite.

Resistance to this mechanism will be a minor concern because it mimics and exploits indirect control mechanisms established by host/pathogen co-existence through thousands and thousands of generations. Therefore, these antibodies provide an anti-parasitic effect without the risk of induction of parasite resistance.

Use of recombinant antibodies circumvents the uncertainty connected with the parameters influencing each step in the classical vaccine development process: Antigen, vaccine formulation, immunogenicity, individual immune response genes, immune response and finally, the interaction of host/parasite/antibody.

DEPOSITS UNDER THE BUDAPEST TREATY

Deposits of *E. coli* TOP10 bacteria containing plasmids encoding RAM Fab fragments have been deposited under the terms of the Budapest Treaty as follows:

Clone:
  TOP10/F'Tet(R)/pFAB73H+RAM1

Depository Institution:
  DSMZ-Deutsche Sammiung von Mikroorganismen und Zellkulturen GmbH, Mascheroder Weg 1 b, D-38124 Braunschweig, Germany.

Date of Deposit:
  14 Aug. 2002

Accession Number:
  DSM 15134

Depositor:
  Morten Hanefeld Dziegiel, HS Blodbank, Copenhagen University Hospital, Blegdamsvej 9, DK-2100 Copenhagen, Denmark.

Clone:
  TOP10/F'Tet(R)/pFAB73H+RAM2

Depository Institution:
  DSMZ-Deutsche Sammlung von Mikroorganismen und Zellkulturen GmbH, Mascheroder Weg 1 b, D-38124 Braunschweig, Germany.

Date of Deposit:
  14 Aug. 2002

Accession Number:
  DSM 15135

Depositor:
  Morten Hanefeld Dziegiel, HS Blodbank, Copenhagen University Hospital, Blegdamsvej 9, DK-2100 Copenhagen, Denmark.

Clone:
  TOP10/F'Tet(R)/pFAB73H+RAM3

Depository Institution:
  DSMZ-Deutsche Samnlung von Mikroorganismen und Zellkulturen GmbH, Mascheroder Weg 1 b, D-38124 Braunschweig, Germany.

Date of Deposit:
  14 Aug. 2002

Accession Number:
  DSM 15136

Depositor:
  Morten Hanefeld Dziegiel, HS Blodbank, Copenhagen University Hospital, Blegdamsvej 9, DK-2100 Copenhagen, Denmark.

The vectors in each of these clones carry the Vk, Ck and VH genes encoding the relevant anti-MSP3 Fab as described above.

REFERENCES

1. Aribot G., Rogier C., Sarthou J. L., Trape J. F., Balde A. T., Druilhe P. and Roussilhon C. (1996) Pattern of immunoglobulin isotype response to *Plasmodium falciparum* blood-stage antigens in individuals living in a holoendemic area of Senegal (Dielmo, west Africa). *Am. J. Trop. Med. Hyg.* 54, 449-457.
2. Ausubel F. M. (1998) *Current protocols in molecular biology*. John Wiley & Sons, Inc.
3. Badell E., Oeuvray C., Moreno A., Soe S., van Rooijen N., Bouzidi A. and Druilhe P. (2000) Human malaria in immunocompromised mice: an in vivo model to study defense mechanisms against Plasmodium falciparum. *J. Exp. Med.* 192, 1653-1660.
4. Bass S., Greene R. and Wells J. A. (1990) Hormone phage: an enrichment method for variant proteins with altered binding properties. *Proteins* 8, 309-314.
5. Bird R. E., Hardman K. D., Jacobson J. W., Johnson S., Kaufman B. M., Lee S. M., Lee T., Pope S. H., Riordan G. S. and Whitlow M. (1988) Single-chain antigen-binding proteins. *Science* 242, 423-426.
6. Bouharoun-Tayoun H., Attanath P., Sabchareon A., Chongsuphajaisiddhi T. and Druilhe P. (1990) Antibodies that protect humans against *Plasmodium falciparum* blood stages do not on their own inhibit parasite growth and invasion in vitro, but act in cooperation with monocytes. *J. Exp. Med.* 172, 1633-1641.
7. Bouharoun-Tayoun H. and Druilhe P. (1992) *Plasmodium falciparum* malaria: evidence for an isotype imbalance which may be responsible for delayed acquisition of protective immunity. *Infect. Immun.* 60, 1473-1481.
8. Bouharoun-Tayoun H., Oeuvray C., Lunel F. and Druilhe P. (1995) Mechanisms underlying the monocyte-mediated antibody-dependent killing of *Plasmodium falciparum* asexual blood stages. *J. Exp. Med.* 182, 409-418.
9. Chirgwin J. M., Przybyla A. E., MacDonald R. J. and Rutter W. J. (1979) Isolation of biologically active ribonucleic acid from sources enriched in ribonuclease. *Biochemistry* 18, 5294-5299.
10. Clackson T., Hoogenboom H. R., Griffiths A. D. and Winter G. (1991) Making antibody fragments using phage display libraries. *Nature* 352, 624-628.
11. Crameri A., Cwirla S. and Stemmer W. P. (1996) Construction and evolution of antibody-phage libraries by DNA shuffling. *Nat. Med.* 2, 100-102.
12. Davies J, Riechmann L., 1994. 'Camelising' human antibody fragments: NMR studies on VH domains. FEBS Lett 339, 285-290
13. Druilhe P. and Khusmith S. (1987) Epidemiological correlation between levels of antibodies promoting merozoite phagocytosis of *Plasmodium falciparum* and malaria-immune status. *Infect. Immun.* 55, 888-891.
14. Druilhe et al. (1997) In vivo veritas : lessons from IgG transfer experiments in malaria patients, Annals. Trop. Med. 91,37-53
15. Dziegiel M., Borre M. B., Jepsen S., Hogh B., Petersen E. and Vuust J. (1991) Recombinant *Plasmodium falciparum* glutamate rich protein; purification and use in enzymelinked immunosorbent assay. *Am. J. Trop. Med. Hyg.* 44, 306-313.
16. Dziegiel M., Nielsen L. K., Andersen P. S., Blancher A., Dickmeiss E. and Engberg J. (1995) Phage display used for gene cloning of human recombinant antibody against the erythrocyte surface antigen, rhesus D. *J. Immunol. Methods* 182, 7-19.

17. Engberg J., Andersen P. S., Nielsen L. K., Dziegiel M., Johansen L. K. and Albrechtsen B. (1996) Phage-display libraries of murine and human antibody Fab fragments. *Mol.Biotechnol.* 6, 287-310.

18. Holliger P., Prospero T. and Winter G. (1993) "Diabodies": small bivalent and bispecific antibody fragments. *Proc. Natl. Acad. Sci. U.S.A* 90, 6444-6448.

19. Hoogenboom H. R., Griffiths A. D., Johnson K. S., Chiswell D. J., Hudson P. and Winter G. (1991) Multi-subunit proteins on the surface of filamentous phage: methodologies for displaying antibody (Fab) heavy and light chains. *Nucleic Acids Res.* 19, 4133-4137.

20. Hu S., Shively L., Raubitschek A., Sherman M., Williams L. E., Wong J. Y., Shively J. E. and Wu A. M. (1996) Minibody: A novel engineered anti-carcinoembryonic antigen antibody fragment (single-chain Fv-CH3) which exhibits rapid, high-level targeting of xenografts. *Cancer Res.* 56, 3055-3061.

21. Huber W., Felger I., Matile H., Lipps H. J., Steiger S. and Beck H. P. (1997) Limited sequence polymorphism in the *Plasmodium falciparum* merozoite surface protein 3. *Mol. Biochem. Parasitol.* 87, 231-234.

22. Huston J. S., Levinson D., Mudgett-Hunter M., Tai M. S., Novotny J., Margolies M. N., Ridge R. J., Bruccoleri R. E., Haber E., Crea R. and . (1988) Protein engineering of antibody binding sites: recovery of specific activity in an anti-digoxin single-chain Fv analogue produced in *Escherichia coli. Proc. Natl. Acad. Sci. U.S.A* 85, 5879-5883.

23. Jirholt P, Ohlin M, Borrebaeck C. A., Soderlind E. (1998). Exploiting sequence space: shuffling in vivo formed complementarity determining regions into a master framework. Gene 1998 Jul 30; 215(2):417-6

24. Kabat E. A. and National Institutes of Health ( (1991) *Sequences of proteins of immunological interest.* U.S. Dept. of Health and Human Services, Public Health Service, National Institutes of Health, Bethesda, Md.

25. Khusmith S. and Druilhe P. (1983) Antibody-dependent ingestion of *P. falciparum* merozoites by human blood monocytes. *Parasite Immunol.* 5, 357-368.

26. Kumaratilake L. M. and Ferrante A. (2000) Opsonization and phagocytosis of *Plasmodium falciparum* merozoites measured by flow cytometry. *Clin. Diagn. Lab Immunol.* 7, 9-13.

27. Manca F, Fenoglio D, Kunkl A, Cambiaggi C, Sasso M, Celada F. (1988) Differential activation of T cell clones stimulated by macrophages exposed to antigen complexed with monoclonal antibodies. A possible influence of paratope specificity on the mode of antigen processing. *J Immunol* 140, 2893-8

28. Marks J. D., Griffiths A. D., Malmqvist M., Clackson T. P., Bye J. M. and Winter G. (1992) By-passing immunization: building high affinity human antibodies by chain shuffling. *Biotechnology* (N.Y.) 10, 779-783.

29. Marks J. D., Hoogenboom H. R., Bonnert T. P., McCafferty J., Griffiths A. D. and Winter G. (1991) By-passing immunization Human antibodies from V-gene libraries displayed on phage. *J.Mol.Biol.* 222, 581-597.

30. McColl D. J. and Anders R. F. (1997) Conservation of structural motifs and antigenic diversity in the *Plasmodium falciparum* merozoite surface protein-3 (MSP-3). *Mol. Biochem. Parasitol.* 90, 21-31.

31. McColl D. J., Silva A., Foley M., Kun J. F., Favaloro J. M., Thompson J. K., Marshall V. M., Coppel R. L., Kemp D. J. and Anders R. F. (1994) Molecular variation in a novel polymorphic antigen associated with *Plasmodium falciparum* merozoites. *Mol. Biochem. Parasitol.* 68, 53-67.

32. McGregor I. A. (1964) The passive transfer of human malarial immunity. *Am. J. Trop. Med. Hyg.* 13, 237-239.

33. McGregor I. A., Carrington S. and Cohen S. (1963) Treatment of East African *P. falciparum* malaria with West African human gamma-globulin. *Trans. R. Soc. Trop. Med. Hyg.* 57, 170-175.

34. Moreno et al. Human malaria in immunocompromised mice: a new model for chemotherapy studies, 2001, 45, 6, 1847-1853

35. Mulhern T. D., Howlett G. J., Reid G. E., Simpson R. J., McColl D. J., Anders R. F. and Norton R. S. (1995) Solution structure of a polypeptide containing four heptad repeat units from a merozoite surface antigen of *Plasmodium falciparum. Biochemistry* 34, 3479-3491.

36. Norderhaug L., Olafsen T., Michaelsen T. E. and Sandlie I. (1997) Versatile vectors for transient and stable expression of recombinant antibody molecules in mammalian cells. *J. Immunol. Methods* 204, 77-87.

37. Oeuvray C., Bouharoun-Tayoun H., Gras-Masse H., Bottius E., Kaidoh T., Aikawa M., Filgueira M.C., Tartar A. and Druilhe P. (1994) Merozoite surface protein-3: a malaria protein inducing antibodies that promote *Plasmodium falciparum* killing by cooperation with blood monocytes. *Blood* 84, 1594-1602.

38. Oeuvray C., Theisen M., Rogier C., Trape J. F., Jepsen S. and Druilhe P. (2000) Cytophilic immunoglobulin responses to *Plasmodium falciparum* glutamate-rich proteir are correlated with protection against clinical malaria in Dielmo, Senegal. *Infect. Immun.* 68, 2617-2620.

39. Ohlin M., Owman H., Mach M. and Borrebaeck C. A. (1996) Light chain shuffling of a high affinity antibody results in a drift in epitope recognition. *Mol. Immunol.* 33, 47-56.

40. Oprea, M. L. Antibody repertoires and pathogen recognition: The role of germline diversity and somatic hypermutation. 1-5-1999. The University of New Mexico. Ref Type: Thesis/Dissertation 41. Orum H., Andersen P. S., Oster A., Johansen L. K., Riise E., Bjornvad M., Svendsen I. and Engberg J. (1993) Efficient method for constructing comprehensive murine Fab antibody libraries displayed on phage. *Nucleic Acids Res.* 21, 4491-4498.

42. Persic L., Roberts A., Wilton J., Cattaneo A., Bradbury A. and Hoogenboom H. R. (1997) An integrated vector system for the eukaryotic expression of antibodies or their fragments after selection from phage display libraries. *Gene* 187, 9-18.

43. Reiter Y., Brinkmann U., Lee B. and Pastan I. (1996) Engineering antibody Fv fragments for cancer detection and therapy: disulfide-stabilized Fv fragments. *Nat. Biotechnol.* 14, 1239-1245.

44. Sabchareon et al. (1991) Parasitoloqical and clinical human response to immunoglobulin administration in *falciparum malaria, Am. J. Trop. Med. Hyg.* 45, 297-308

45. Sambrook J., Maniatis T. and Fritsch E. F. (1989) *Molecular cloning a laboratory manual.* Cold Spring Harbor Laboratory, Cold Spring Harbor, N.Y.

46. Sanna P. P., Samson M. E., Moon J. S., Rozenshteyn R., De Logu A., Williamson R. A. and Burton D. R. (1999) pFab-CMV, a single vector system for the rapid conversion of recombinant Fabs into whole IgG1 antibodies. *Immunotechnology.* 4, 185-188.

47. Seehaus T., Breitling F., Dubel S., Klewinghaus I. and Little M. (1992) A vector for the removal of deletion mutants from antibody libraries. *Gene* 114, 235-237.
48. Sheeley D. M., Merrill B. M. and Taylor L. C. (1997) Characterization of monoclonal antibody glycosylation: comparison of expression systems and identification of terminal alpha-linked galactose. *Anal. Biochem.* 247, 102-110.
49. Shi Y. P., Udhayakumar V., Oloo A. J., Nahlen B. L. and Lal A. A. (1999) Differential effect and interaction of monocytes, hyperimmune sera, and immunoglobulin G on the growth of asexual stage *Plasmodium falciparum* parasites. *Am. J. Trop. Med. Hyg.* 60, 135-141.
50. Trager W. and Jensen J. B. (1976) Human malaria parasites in continuous culture. *Science* 193, 673-675.
51. Trucco C., Fernandez-Reyes D., Howell S., Stafford W. H., Scott-Finnigan T. J., Grainger M., Ogun S. A., Taylor W. R. and Holder A. A. (2001) The merozoite surface protein 6 gene codes for a 36 kDa protein associated with the *Plasmodium falciparum* merozoite surface protein-1 complex. *Mol. Biochem. Parasitol.* 112, 91-101.
52. van der Heyde H. C., Elloso M. M., vande W. J., Schell K. and Weidanz W. P. (1995) Use of hydroethidine and flow cytometry to assess the effects of leukocytes on the malarial parasite *Plasmodium falciparum. Clin. Diagn. Lab Immunol.* 2, 417-425.
53. Walls M. A., Hsiao K. C. and Harris L. J. (1993) Vectors for the expression of PCR-amplified immunoglobulin variable domains with human constant regions. *Nucleic Acids Res.* 21, 2921-2929.
54. Zhang W, Liu XQ, Xu H, Good MF (2002) Polyspecific malaria antibodies present at the time of infection inhibit the development of immunity to malaria but antibodies specific for the malaria merozoite surface protein, MSP1, facilitate immunity. Parasite Immunol 24, 233-41

The invention claimed is:

1. A purified human antibody, or antigen binding fragment thereof, specific for the Merozoite Surface Protein-3 (MSP-3) antigen of *Plasmodium falciparum*, wherein the antibody comprises:
   a) a heavy chain with Complementarity Determining Regions (CDRs) having the amino acid sequences:
   SYAMH, which corresponds to amino acid residues 31-35 of SEQ ID NO: 1; VISYDGSNKYYADSVKG, which corresponds to amino acid residues 50-66 of SEQ ID NO: 1; and GASS which corresponds to amino acid residues 99-102 of SEQ ID NO: 1; and
   b) a light chain with CDRs having amino the amino sequences:
   RASQSISSWLA, which corresponds to amino acid residues 24-34 of SEQ ID NO: 2; KASSLES, which corresponds to amino acid residues 50-56 of SEQ ID NO: 2; and QQYKSFPYT, which corresponds to amino acid residues 89-97 of SEQ ID NO: 2.

2. A purified human antibody, or antigen binding fragment thereof, specific for the Merozoite Surface Protein-3 (MSP-3) antigen of *Plasmodium falciparum*, wherein the antibody comprises:
   a) a heavy chain with Complementarity Determining Regions (CDRs) having the amino acid sequences:
   SYGMS, which corresponds to amino acid residues 31-35 of SEQ ID NO: 3; TISSGGSYTYYPDSVKG, which corresponds to amino acid residues 50-66 of SEQ ID NO: 3; and LYYGYRYYFDY, which corresponds to amino acid residues 99-109 of SEQ ID NO: 3; and
   b) a light chain with CDRs having amino the amino sequences:
   QASQDITNSLN, which corresponds to amino acid residues 24-34 of SEQ ID NO: 4; DAFTLKT, which corresponds to amino acid residues 50-56 of SEQ ID NO: 4; and QQSHRVPFT, which corresponds to amino acid residues 89-97 of SEQ ID NO: 4.

3. A purified human antibody, or antigen binding fragment thereof, specific for the Merozoite Surface Protein-3 (MSP-3) antigen of *Plasmodium falciparum*, wherein the antibody comprises:
   a) a heavy chain with Complementarity Determining Regions (CDRs) having the amino acid sequences:
   SYAMH, which corresponds to amino acid residues 31-35 of SEQ ID NO: 5; VISYDGSNKYYADSVKG, which corresponds to amino acid residues 50-66 of SEQ ID NO: 5; and DSGGIAARLGGYFDL, which corresponds to amino acid residues 99-113 of SEQ ID NO: 5; and
   b) a light chain with CDRs having amino the amino sequences:
   RASQGISSYLA, which corresponds to amino acid residues 24-34 of SEQ ID NO: 6; AASTLQS, which corresponds to amino acid residues 50-56 of SEQ ID NO: 6; and QQGPT, which corresponds to amino acid residues 89-93 of SEQ ID NO: 6.

4. The antibody, or antigen binding fragment thereof, according to any of claims 1, 2, and 3, which is specific for the Merozoite Surface Protein 3 (MSP-3)$_{194-257}$ antigen.

5. The antibody, or antigen binding fragment thereof, according to claim 4, which is specific for an epitope having the amino acid sequence ILGWEFGGGVP (SEQ ID NO: 10), which corresponds to residues 220-230 of the Merozoite Surface Protein 3 (MSP-3) antigen.

6. The antibody, or antigen binding fragment thereof, according to claim 1 comprising the VH domain of Recombinant Anti-MSP-3 No. 1 (RAM1) having the amino acid sequence of SEQ ID NO: 1.

7. The antibody, or antigen binding fragment thereof, according to claim 2 comprising the VH domain of Recombinant Anti-MSP-3 No. 2 (RAM2) having the amino acid sequence of SEQ ID NO: 3.

8. The antibody, or antigen binding fragment thereof, according to claim 3 comprising the VH domain of Recombinant Anti-MSP-3 No. 3 (RAM3) having the amino acid sequence of SEQ ID NO: 5.

9. The antibody, or antigen binding fragment thereof, according to claim 1 comprising the VL domain of Recombinant Anti-MSP-3 No. 1 (RAM1) having the amino acid sequence of SEQ ID NO: 2.

10. The antibody, or antigen binding fragment thereof, according to claim 2 comprising the VL domain of Recombinant Anti-MSP-3 No. 2 (RAM2) having the amino acid sequence of SEQ ID NO: 4.

11. The antibody, or antigen binding fragment thereof, according to claim 3 comprising the VL domain of Recombinant Anti-MSP-3 No. 3 (RAM3) having the amino acid sequence of SEQ ID NO: 6.

12. The antibody, or antigen binding fragment thereof, according to claim 6 further comprising the VL domain of Recombinant Anti-MSP-3 No. 1 (RAM1) having the amino acid sequence of SEQ ID NO: 2.

13. The antibody, or antigen binding fragment thereof, according to claim 7 further comprising the VL domain of Recombinant Anti-MSP-3 No. 2 (RAM2) having the amino acid sequence of SEQ ID NO: 4.

14. The antibody, or antigen binding fragment thereof, according to claim 8 further comprising the VL domain of Recombinant Anti-MSP-3 No. 3 (RAM3) having the amino acid sequence of SEQ ID NO: 6.

15. The antibody, or antigen binding fragment thereof, according to any one of claims 1, 2, and 3, which comprises a constant region selected from: gamma 1; gamma 2; gamma 3; gamma 4; mu; alpha 1; alpha 2; delta; or epsilon isotypes.

16. The antibody, or antigen binding fragment thereof, according to claim 15, wherein the constant region is selected from: the gamma 1; gamma 2; gamma 3; or gamma 4 isotypes, to form an IgG molecule.

17. The antibody, or antigen binding fragment thereof, according to claim 16, wherein the constant region is selected from: the gamma 1 or the gamma 3 isotypes, to form an IgG1 or IgG3 isotype.

18. The antibody, or antigen binding fragment thereof, according to claim 17 having the allotype G1m(a,z), G1m(f), G3m(b), G3m(c3c5), G3m(c3), or G3m(s).

19. The antibody, or antigen binding fragment thereof, according to claim 18 having the allotype G1m(a,z) or G3m(b).

20. A composition comprising the antibody, or antigen binding fragment thereof, according to any of claims 1, 2, and 3, wherein the antibody or antigen binding fragment thereof binds to the Merozoite Surface Protein-3 (MSP-3) antigen of *Plasmodium falciparum*.

21. The antibody, or antigen binding fragment thereof, of any of claims 1, 2, and 3, wherein the antibody, or antigen binding fragment thereof, is monoclonal.

22. The antibody, or antigen binding fragment thereof, of any of claims 1, 2, and 3, wherein the antibody, or antigen binding fragment thereof, is recombinant.

23. A pharmaceutical composition comprising the antibody, or antigen binding fragment thereof, according to any of claims 1, 2, and 3.

24. The pharmaceutical composition of claim 23, wherein the dose of antibody, or antigen binding fragment thereof, is chosen from 10 µg to 10 mg antibody, or antigen binding fragment thereof, per kg body weight, 1.5 mg to 3.5 mg antibody, or antigen binding fragment thereof, per kg body weight, 2 mg antibody, or antigen binding fragment thereof, per kg body weight, 0.1 µg to 3 mg antibody, or antigen binding fragment thereof, per kg body weight, 0.1 mg to 2 mg antibody, or antigen binding fragment thereof, per kg body weight, 0.5 mg to 1.5 mg antibody, or antigen binding fragment thereof, per kg body weight, 0.75 to 1 mg antibody, or antigen binding fragment thereof, per kg body weight, and 1 mg antibody, or antigen binding fragment thereof, per 1 kg body weight.

25. A method of diagnosis of malaria comprising taking a sample of bodily fluid from an individual, contacting the sample with an antibody, or antigen binding fragment, according to any one of claims 1, 2, and 3 and determining the binding of the antibody or antigen binding fragment to the sample, thereby determining the presence or absence of malaria in the sample.

26. A process of treatment of a malaria infection comprising administering to an infected patient a purified antibody or antigen binding fragment according to claim 1, 2 or 3.

27. A process of treatment of a malaria infection comprising administering to an infected patient the composition of claim 23.

\* \* \* \* \*

UNITED STATES PATENT AND TRADEMARK OFFICE
CERTIFICATE OF CORRECTION

| | | |
|---|---|---|
| PATENT NO. | : 7,811,569 B2 | Page 1 of 1 |
| APPLICATION NO. | : 10/486703 | |
| DATED | : October 12, 2010 | |
| INVENTOR(S) | : Morten Steen Hanefeld Dziegiel et al. | |

It is certified that error appears in the above-identified patent and that said Letters Patent is hereby corrected as shown below:

On the title page, item [73] should read:

RAM Biotech APS
c/o Copenhagen University Hospital
Copenhagen, Denmark and

Institut Pasteur
Paris, France

Signed and Sealed this
Fifth Day of July, 2011

David J. Kappos
*Director of the United States Patent and Trademark Office*

SEQUENCE LISTING

```
<160> NUMBER OF SEQ ID NOS: 86

<210> SEQ ID NO 1
<211> LENGTH: 114
<212> TYPE: PRT
<213> ORGANISM: Homo sapiens

<400> SEQUENCE: 1

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys Gly Ala Ser Ser Trp Ser Thr Gly Thr Leu Val Thr Val Ser
            100                 105                 110

Ser Ala

<210> SEQ ID NO 2
<211> LENGTH: 108
<212> TYPE: PRT
<213> ORGANISM: Homo sapiens

<400> SEQUENCE: 2

Asp Ile Val Met Met Gln Ser Pro Ala Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Ser Gly Val Pro Ser Arg Phe Ser Gly
    50                  55                  60
```

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Lys Ser Phe Pro Tyr
                 85                  90                  95

Thr Phe Gly Gln Gly Thr Arg Leu Glu Ile Lys Arg
            100                 105

<210> SEQ ID NO 3
<211> LENGTH: 121
<212> TYPE: PRT
<213> ORGANISM: Homo sapiens

<400> SEQUENCE: 3

Gln Val Gln Leu Gln Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg Leu Tyr Tyr Gly Tyr Arg Tyr Tyr Phe Asp Tyr Trp Gly Gln
            100                 105                 110

Gly Thr Met Val Thr Val Ser Ser Ala
        115                 120

<210> SEQ ID NO 4
<211> LENGTH: 108
<212> TYPE: PRT
<213> ORGANISM: Homo sapiens

<400> SEQUENCE: 4

Asp Ile Gln Leu Thr Gln Ser Pro Ser Ser Leu Ser Ala Ser Ile Gly
 1               5                  10                  15

Asp Arg Val Thr Ile Thr Cys Gln Ala Ser Gln Asp Ile Thr Asn Ser
                20                  25                  30

Leu Asn Trp Tyr Gln Gln Arg Pro Gly Gln Ala Pro Lys Leu Leu Ile
            35                  40                  45

Tyr Asp Ala Phe Thr Leu Lys Thr Gly Val Pro Ser Arg Phe Ser Gly
 50                  55                  60

Arg Gly Ser Gly Thr Ser Phe Thr Ile Ala Ile Asn Ser Phe Gln Ala
 65                  70                  75                  80

Glu Asp Ile Gly Thr Tyr Phe Cys Gln Gln Ser His Arg Val Pro Phe
                 85                  90                  95

Thr Phe Gly Gly Gly Thr Arg Val Glu Ile Lys Arg
            100                 105

<210> SEQ ID NO 5
<211> LENGTH: 125
<212> TYPE: PRT
<213> ORGANISM: Homo sapiens

<400> SEQUENCE: 5

Gln Val Gln Leu Val Gln Ser Gly Gly Gly Val Val Gln Pro Gly Arg
```

```
             1               5                  10                 15

Ser Leu Arg Leu Ser Cys Ala Ala Ser Gly Phe Thr Phe Ser Ser Tyr
                    20                  25                  30

Ala Met His Trp Val Arg Gln Ala Pro Gly Lys Gly Leu Glu Trp Val
                35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Lys Ala Val Tyr Tyr Cys
                    85                  90                  95

Ala Arg Asp Ser Gly Gly Ile Ala Ala Arg Leu Gly Gly Tyr Phe Asp
                100                 105                 110

Leu Trp Gly Arg Gly Thr Thr Val Thr Val Ser Ser Ala
                115                 120                 125

<210> SEQ ID NO 6
<211> LENGTH: 104
<212> TYPE: PRT
<213> ORGANISM: Homo sapiens

<400> SEQUENCE: 6

Asp Ile Arg Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
                35                  40                  45

Tyr Ala Ala Ser Thr Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Pro Thr Phe Gly Gly
                    85                  90                  95

Gly Thr Lys Val Glu Ile Lys Arg
                100

<210> SEQ ID NO 7
<211> LENGTH: 64
<212> TYPE: PRT
<213> ORGANISM: Plasmodium falciparum

<400> SEQUENCE: 7

His Glu Arg Ala Lys Asn Ala Tyr Gln Lys Ala Asn Gln Ala Val Leu
1               5                   10                  15

Lys Ala Lys Glu Ala Ser Ser Tyr Asp Tyr Ile Leu Gly Trp Glu Phe
                20                  25                  30

Gly Gly Gly Val Pro Glu His Lys Lys Glu Glu Asn Met Leu Ser His
            35                  40                  45

Leu Tyr Val Ser Ser Lys Asp Lys Glu Asn Ile Ser Lys Glu Asn Glu
            50                  55                  60

<210> SEQ ID NO 8
<211> LENGTH: 28
<212> TYPE: PRT
<213> ORGANISM: Plasmodium falciparum

<400> SEQUENCE: 8
```

```
Val Glu Lys Asp Tyr Glu Arg Ala Lys Asn Ala Tyr Gln Lys Ala Asn
1               5                   10                  15

Gln Ala Val Leu Lys Ala Lys Glu Ala Ser Ser Tyr
            20                  25

<210> SEQ ID NO 9
<211> LENGTH: 27
<212> TYPE: PRT
<213> ORGANISM: Plasmodium falciparum

<400> SEQUENCE: 9

Ala Lys Glu Ala Ser Ser Tyr Asp Tyr Ile Leu Gly Trp Glu Phe Gly
1               5                   10                  15

Gly Gly Val Pro Glu His Lys Lys Glu Glu Asn
            20                  25

<210> SEQ ID NO 10
<211> LENGTH: 11
<212> TYPE: PRT
<213> ORGANISM: Plasmodium falciparum

<400> SEQUENCE: 10

Ile Leu Gly Trp Glu Phe Gly Gly Gly Val Pro
1               5                   10

<210> SEQ ID NO 11
<211> LENGTH: 14
<212> TYPE: PRT
<213> ORGANISM: Plasmodium falciparum

<400> SEQUENCE: 11

His Glu Arg Ala Lys Asn Ala Tyr Gln Lys Ala Asn Gln Ala
1               5                   10

<210> SEQ ID NO 12
<211> LENGTH: 15
<212> TYPE: PRT
<213> ORGANISM: Plasmodium falciparum

<400> SEQUENCE: 12

Lys Ala Lys Glu Ala Ser Ser Tyr Asp Tyr Ile Leu Gly Trp Glu
1               5                   10                  15

<210> SEQ ID NO 13
<211> LENGTH: 14
<212> TYPE: PRT
<213> ORGANISM: Plasmodium falciparum

<400> SEQUENCE: 13

Glu Arg Ala Lys Asn Ala Tyr Gln Lys Ala Asn Gln Ala Val
1               5                   10

<210> SEQ ID NO 14
<211> LENGTH: 15
<212> TYPE: PRT
<213> ORGANISM: Plasmodium falciparum

<400> SEQUENCE: 14

Ala Lys Glu Ala Ser Ser Tyr Asp Tyr Ile Leu Gly Trp Glu Phe
1               5                   10                  15

<210> SEQ ID NO 15
<211> LENGTH: 14
```

```
<212> TYPE: PRT
<213> ORGANISM: Plasmodium falciparum

<400> SEQUENCE: 15

Arg Ala Lys Asn Ala Tyr Gln Lys Ala Asn Gln Ala Val Leu
1               5                   10

<210> SEQ ID NO 16
<211> LENGTH: 15
<212> TYPE: PRT
<213> ORGANISM: Plasmodium falciparum

<400> SEQUENCE: 16

Lys Glu Ala Ser Ser Tyr Asp Tyr Ile Leu Gly Trp Glu Phe Gly
1               5                   10                  15

<210> SEQ ID NO 17
<211> LENGTH: 14
<212> TYPE: PRT
<213> ORGANISM: Plasmodium falciparum

<400> SEQUENCE: 17

Ala Lys Asn Ala Tyr Gln Lys Ala Asn Gln Ala Val Leu Lys
1               5                   10

<210> SEQ ID NO 18
<211> LENGTH: 15
<212> TYPE: PRT
<213> ORGANISM: Plasmodium falciparum

<400> SEQUENCE: 18

Glu Ala Ser Ser Tyr Asp Tyr Ile Leu Gly Trp Glu Phe Gly Gly
1               5                   10                  15

<210> SEQ ID NO 19
<211> LENGTH: 14
<212> TYPE: PRT
<213> ORGANISM: Plasmodium falciparum

<400> SEQUENCE: 19

Lys Asn Ala Tyr Gln Lys Ala Asn Gln Ala Val Leu Lys Ala
1               5                   10

<210> SEQ ID NO 20
<211> LENGTH: 15
<212> TYPE: PRT
<213> ORGANISM: Plasmodium falciparum

<400> SEQUENCE: 20

Ala Ser Ser Tyr Asp Tyr Ile Leu Gly Trp Glu Phe Gly Gly Gly
1               5                   10                  15

<210> SEQ ID NO 21
<211> LENGTH: 14
<212> TYPE: PRT
<213> ORGANISM: Plasmodium falciparum

<400> SEQUENCE: 21

Asn Ala Tyr Gln Lys Ala Asn Gln Ala Val Leu Lys Ala Lys
1               5                   10

<210> SEQ ID NO 22
<211> LENGTH: 15
<212> TYPE: PRT
<213> ORGANISM: Plasmodium falciparum
```

-continued

<400> SEQUENCE: 22

Ser Ser Tyr Asp Tyr Ile Leu Gly Trp Glu Phe Gly Gly Gly Val
1               5                   10                  15

<210> SEQ ID NO 23
<211> LENGTH: 14
<212> TYPE: PRT
<213> ORGANISM: Plasmodium falciparum

<400> SEQUENCE: 23

Ala Tyr Gln Lys Ala Asn Gln Ala Val Leu Lys Ala Lys Glu
1               5                   10

<210> SEQ ID NO 24
<211> LENGTH: 15
<212> TYPE: PRT
<213> ORGANISM: Plasmodium falciparum

<400> SEQUENCE: 24

Ser Tyr Asp Tyr Ile Leu Gly Trp Glu Phe Gly Gly Gly Val Pro
1               5                   10                  15

<210> SEQ ID NO 25
<211> LENGTH: 14
<212> TYPE: PRT
<213> ORGANISM: Plasmodium falciparum

<400> SEQUENCE: 25

Tyr Gln Lys Ala Asn Gln Ala Val Leu Lys Ala Lys Glu Ala
1               5                   10

<210> SEQ ID NO 26
<211> LENGTH: 15
<212> TYPE: PRT
<213> ORGANISM: Plasmodium falciparum

<400> SEQUENCE: 26

Tyr Asp Tyr Ile Leu Gly Trp Glu Phe Gly Gly Gly Val Pro Glu
1               5                   10                  15

<210> SEQ ID NO 27
<211> LENGTH: 14
<212> TYPE: PRT
<213> ORGANISM: Plasmodium falciparum

<400> SEQUENCE: 27

Gln Lys Ala Asn Gln Ala Val Leu Lys Ala Lys Glu Ala Ser
1               5                   10

<210> SEQ ID NO 28
<211> LENGTH: 15
<212> TYPE: PRT
<213> ORGANISM: Plasmodium falciparum

<400> SEQUENCE: 28

Asp Tyr Ile Leu Gly Trp Glu Phe Gly Gly Gly Val Pro Glu His
1               5                   10                  15

<210> SEQ ID NO 29
<211> LENGTH: 14
<212> TYPE: PRT
<213> ORGANISM: Plasmodium falciparum

<400> SEQUENCE: 29

```
Lys Ala Asn Gln Ala Val Leu Lys Ala Lys Glu Ala Ser Ser
1               5                   10
```

<210> SEQ ID NO 30
<211> LENGTH: 15
<212> TYPE: PRT
<213> ORGANISM: Plasmodium falciparum

<400> SEQUENCE: 30

```
Tyr Ile Leu Gly Trp Glu Phe Gly Gly Gly Val Pro Glu His Lys
1               5                   10                  15
```

<210> SEQ ID NO 31
<211> LENGTH: 14
<212> TYPE: PRT
<213> ORGANISM: Plasmodium falciparum

<400> SEQUENCE: 31

```
Ala Asn Gln Ala Val Leu Lys Ala Lys Glu Ala Ser Ser Tyr
1               5                   10
```

<210> SEQ ID NO 32
<211> LENGTH: 15
<212> TYPE: PRT
<213> ORGANISM: Plasmodium falciparum

<400> SEQUENCE: 32

```
Ile Leu Gly Trp Glu Phe Gly Gly Gly Val Pro Glu His Lys Lys
1               5                   10                  15
```

<210> SEQ ID NO 33
<211> LENGTH: 14
<212> TYPE: PRT
<213> ORGANISM: Plasmodium falciparum

<400> SEQUENCE: 33

```
Asn Gln Ala Val Leu Lys Ala Lys Glu Ala Ser Ser Tyr Asp
1               5                   10
```

<210> SEQ ID NO 34
<211> LENGTH: 15
<212> TYPE: PRT
<213> ORGANISM: Plasmodium falciparum

<400> SEQUENCE: 34

```
Leu Gly Trp Glu Phe Gly Gly Gly Val Pro Glu His Lys Lys Glu
1               5                   10                  15
```

<210> SEQ ID NO 35
<211> LENGTH: 14
<212> TYPE: PRT
<213> ORGANISM: Plasmodium falciparum

<400> SEQUENCE: 35

```
Gln Ala Val Leu Lys Ala Lys Glu Ala Ser Ser Tyr Asp Tyr
1               5                   10
```

<210> SEQ ID NO 36
<211> LENGTH: 15
<212> TYPE: PRT
<213> ORGANISM: Plasmodium falciparum

<400> SEQUENCE: 36

```
Gly Trp Glu Phe Gly Gly Gly Val Pro Glu His Lys Lys Glu Glu
```

```
1               5                  10                  15
```

<210> SEQ ID NO 37
<211> LENGTH: 14
<212> TYPE: PRT
<213> ORGANISM: Plasmodium falciparum

<400> SEQUENCE: 37

```
Ala Val Leu Lys Ala Lys Glu Ala Ser Ser Tyr Asp Tyr Ile
1               5                  10
```

<210> SEQ ID NO 38
<211> LENGTH: 15
<212> TYPE: PRT
<213> ORGANISM: Plasmodium falciparum

<400> SEQUENCE: 38

```
Trp Glu Phe Gly Gly Gly Val Pro Glu His Lys Lys Glu Glu Asn
1               5                  10                  15
```

<210> SEQ ID NO 39
<211> LENGTH: 14
<212> TYPE: PRT
<213> ORGANISM: Plasmodium falciparum

<400> SEQUENCE: 39

```
Val Leu Lys Ala Lys Glu Ala Ser Ser Tyr Asp Tyr Ile Leu
1               5                  10
```

<210> SEQ ID NO 40
<211> LENGTH: 15
<212> TYPE: PRT
<213> ORGANISM: Plasmodium falciparum

<400> SEQUENCE: 40

```
Glu Phe Gly Gly Gly Val Pro Glu His Lys Lys Glu Glu Asn Met
1               5                  10                  15
```

<210> SEQ ID NO 41
<211> LENGTH: 14
<212> TYPE: PRT
<213> ORGANISM: Plasmodium falciparum

<400> SEQUENCE: 41

```
Leu Lys Ala Lys Glu Ala Ser Ser Tyr Asp Tyr Ile Leu Gly
1               5                  10
```

<210> SEQ ID NO 42
<211> LENGTH: 15
<212> TYPE: PRT
<213> ORGANISM: Plasmodium falciparum

<400> SEQUENCE: 42

```
Phe Gly Gly Gly Val Pro Glu His Lys Lys Glu Glu Asn Met Leu
1               5                  10                  15
```

<210> SEQ ID NO 43
<211> LENGTH: 14
<212> TYPE: PRT
<213> ORGANISM: Plasmodium falciparum

<400> SEQUENCE: 43

```
Lys Ala Lys Glu Ala Ser Ser Tyr Asp Tyr Ile Leu Gly Trp
1               5                  10
```

<210> SEQ ID NO 44
<211> LENGTH: 15
<212> TYPE: PRT
<213> ORGANISM: Plasmodium falciparum

<400> SEQUENCE: 44

Gly Gly Gly Val Pro Glu His Lys Lys Glu Glu Asn Met Leu Ser
1               5                   10                  15

<210> SEQ ID NO 45
<211> LENGTH: 14
<212> TYPE: PRT
<213> ORGANISM: Plasmodium falciparum

<400> SEQUENCE: 45

Ala Lys Glu Ala Ser Ser Tyr Asp Tyr Ile Leu Gly Trp Glu
1               5                   10

<210> SEQ ID NO 46
<211> LENGTH: 15
<212> TYPE: PRT
<213> ORGANISM: Plasmodium falciparum

<400> SEQUENCE: 46

Gly Gly Val Pro Glu His Lys Lys Glu Glu Asn Met Leu Ser His
1               5                   10                  15

<210> SEQ ID NO 47
<211> LENGTH: 14
<212> TYPE: PRT
<213> ORGANISM: Plasmodium falciparum

<400> SEQUENCE: 47

Lys Glu Ala Ser Ser Tyr Asp Tyr Ile Leu Gly Trp Glu Phe
1               5                   10

<210> SEQ ID NO 48
<211> LENGTH: 15
<212> TYPE: PRT
<213> ORGANISM: Plasmodium falciparum

<400> SEQUENCE: 48

Gly Val Pro Glu His Lys Lys Glu Glu Asn Met Leu Ser His Leu
1               5                   10                  15

<210> SEQ ID NO 49
<211> LENGTH: 14
<212> TYPE: PRT
<213> ORGANISM: Plasmodium falciparum

<400> SEQUENCE: 49

Glu Ala Ser Ser Tyr Asp Tyr Ile Leu Gly Trp Glu Phe Gly
1               5                   10

<210> SEQ ID NO 50
<211> LENGTH: 15
<212> TYPE: PRT
<213> ORGANISM: Plasmodium falciparum

<400> SEQUENCE: 50

Val Pro Glu His Lys Lys Glu Glu Asn Met Leu Ser His Leu Tyr
1               5                   10                  15

<210> SEQ ID NO 51

```
<211> LENGTH: 14
<212> TYPE: PRT
<213> ORGANISM: Plasmodium falciparum

<400> SEQUENCE: 51

Ala Ser Ser Tyr Asp Tyr Ile Leu Gly Trp Glu Phe Gly Gly
1               5                   10

<210> SEQ ID NO 52
<211> LENGTH: 15
<212> TYPE: PRT
<213> ORGANISM: Plasmodium falciparum

<400> SEQUENCE: 52

Pro Glu His Lys Lys Glu Glu Asn Met Leu Ser His Leu Tyr Val
1               5                   10                  15

<210> SEQ ID NO 53
<211> LENGTH: 14
<212> TYPE: PRT
<213> ORGANISM: Plasmodium falciparum

<400> SEQUENCE: 53

Ser Ser Tyr Asp Tyr Ile Leu Gly Trp Glu Phe Gly Gly Gly
1               5                   10

<210> SEQ ID NO 54
<211> LENGTH: 15
<212> TYPE: PRT
<213> ORGANISM: Plasmodium falciparum

<400> SEQUENCE: 54

Glu His Lys Lys Glu Glu Asn Met Leu Ser His Leu Tyr Val Ser
1               5                   10                  15

<210> SEQ ID NO 55
<211> LENGTH: 14
<212> TYPE: PRT
<213> ORGANISM: Plasmodium falciparum

<400> SEQUENCE: 55

Ser Tyr Asp Tyr Ile Leu Gly Trp Glu Phe Gly Gly Gly Val
1               5                   10

<210> SEQ ID NO 56
<211> LENGTH: 15
<212> TYPE: PRT
<213> ORGANISM: Plasmodium falciparum

<400> SEQUENCE: 56

His Lys Lys Glu Glu Asn Met Leu Ser His Leu Tyr Val Ser Ser
1               5                   10                  15

<210> SEQ ID NO 57
<211> LENGTH: 14
<212> TYPE: PRT
<213> ORGANISM: Plasmodium falciparum

<400> SEQUENCE: 57

Tyr Asp Tyr Ile Leu Gly Trp Glu Phe Gly Gly Gly Val Pro
1               5                   10

<210> SEQ ID NO 58
<211> LENGTH: 15
<212> TYPE: PRT
```

<213> ORGANISM: Plasmodium falciparum

<400> SEQUENCE: 58

Lys Lys Glu Glu Asn Met Leu Ser His Leu Tyr Val Ser Ser Lys
1               5                   10                  15

<210> SEQ ID NO 59
<211> LENGTH: 14
<212> TYPE: PRT
<213> ORGANISM: Plasmodium falciparum

<400> SEQUENCE: 59

Asp Tyr Ile Leu Gly Trp Glu Phe Gly Gly Gly Val Pro Glu
1               5                   10

<210> SEQ ID NO 60
<211> LENGTH: 15
<212> TYPE: PRT
<213> ORGANISM: Plasmodium falciparum

<400> SEQUENCE: 60

Lys Glu Glu Asn Met Leu Ser His Leu Tyr Val Ser Ser Lys Asp
1               5                   10                  15

<210> SEQ ID NO 61
<211> LENGTH: 14
<212> TYPE: PRT
<213> ORGANISM: Plasmodium falciparum

<400> SEQUENCE: 61

Tyr Ile Leu Gly Trp Glu Phe Gly Gly Gly Val Pro Glu His
1               5                   10

<210> SEQ ID NO 62
<211> LENGTH: 15
<212> TYPE: PRT
<213> ORGANISM: Plasmodium falciparum

<400> SEQUENCE: 62

Glu Glu Asn Met Leu Ser His Leu Tyr Val Ser Ser Lys Asp Lys
1               5                   10                  15

<210> SEQ ID NO 63
<211> LENGTH: 14
<212> TYPE: PRT
<213> ORGANISM: Plasmodium falciparum

<400> SEQUENCE: 63

Ile Leu Gly Trp Glu Phe Gly Gly Gly Val Pro Glu His Lys
1               5                   10

<210> SEQ ID NO 64
<211> LENGTH: 15
<212> TYPE: PRT
<213> ORGANISM: Plasmodium falciparum

<400> SEQUENCE: 64

Glu Asn Met Leu Ser His Leu Tyr Val Ser Ser Lys Asp Lys Glu
1               5                   10                  15

<210> SEQ ID NO 65
<211> LENGTH: 14
<212> TYPE: PRT
<213> ORGANISM: Plasmodium falciparum

```
<400> SEQUENCE: 65

Leu Gly Trp Glu Phe Gly Gly Gly Val Pro Glu His Lys Lys
1               5                   10

<210> SEQ ID NO 66
<211> LENGTH: 15
<212> TYPE: PRT
<213> ORGANISM: Plasmodium falciparum

<400> SEQUENCE: 66

Asn Met Leu Ser His Leu Tyr Val Ser Ser Lys Asp Lys Glu Asn
1               5                   10                  15

<210> SEQ ID NO 67
<211> LENGTH: 14
<212> TYPE: PRT
<213> ORGANISM: Plasmodium falciparum

<400> SEQUENCE: 67

Gly Trp Glu Phe Gly Gly Gly Val Pro Glu His Lys Lys Glu
1               5                   10

<210> SEQ ID NO 68
<211> LENGTH: 15
<212> TYPE: PRT
<213> ORGANISM: Plasmodium falciparum

<400> SEQUENCE: 68

Met Leu Ser His Leu Tyr Val Ser Ser Lys Asp Lys Glu Asn Ile
1               5                   10                  15

<210> SEQ ID NO 69
<211> LENGTH: 14
<212> TYPE: PRT
<213> ORGANISM: Plasmodium falciparum

<400> SEQUENCE: 69

Trp Glu Phe Gly Gly Gly Val Pro Glu His Lys Lys Glu Glu
1               5                   10

<210> SEQ ID NO 70
<211> LENGTH: 15
<212> TYPE: PRT
<213> ORGANISM: Plasmodium falciparum

<400> SEQUENCE: 70

Leu Ser His Leu Tyr Val Ser Ser Lys Asp Lys Glu Asn Ile Ser
1               5                   10                  15

<210> SEQ ID NO 71
<211> LENGTH: 14
<212> TYPE: PRT
<213> ORGANISM: Plasmodium falciparum

<400> SEQUENCE: 71

Glu Phe Gly Gly Gly Val Pro Glu His Lys Lys Glu Glu Asn
1               5                   10

<210> SEQ ID NO 72
<211> LENGTH: 15
<212> TYPE: PRT
<213> ORGANISM: Plasmodium falciparum

<400> SEQUENCE: 72
```

-continued

Ser His Leu Tyr Val Ser Ser Lys Asp Lys Glu Asn Ile Ser Lys
1               5                   10                  15

<210> SEQ ID NO 73
<211> LENGTH: 14
<212> TYPE: PRT
<213> ORGANISM: Plasmodium falciparum

<400> SEQUENCE: 73

Phe Gly Gly Gly Val Pro Glu His Lys Lys Glu Glu Asn Met
1               5                   10

<210> SEQ ID NO 74
<211> LENGTH: 15
<212> TYPE: PRT
<213> ORGANISM: Plasmodium falciparum

<400> SEQUENCE: 74

His Leu Tyr Val Ser Ser Lys Asp Lys Glu Asn Ile Ser Lys Glu
1               5                   10                  15

<210> SEQ ID NO 75
<211> LENGTH: 14
<212> TYPE: PRT
<213> ORGANISM: Plasmodium falciparum

<400> SEQUENCE: 75

Gly Gly Gly Val Pro Glu His Lys Lys Glu Glu Asn Met Leu
1               5                   10

<210> SEQ ID NO 76
<211> LENGTH: 15
<212> TYPE: PRT
<213> ORGANISM: Plasmodium falciparum

<400> SEQUENCE: 76

Leu Tyr Val Ser Ser Lys Asp Lys Glu Asn Ile Ser Lys Glu Asn
1               5                   10                  15

<210> SEQ ID NO 77
<211> LENGTH: 14
<212> TYPE: PRT
<213> ORGANISM: Plasmodium falciparum

<400> SEQUENCE: 77

Gly Gly Val Pro Glu His Lys Lys Glu Glu Asn Met Leu Ser
1               5                   10

<210> SEQ ID NO 78
<211> LENGTH: 15
<212> TYPE: PRT
<213> ORGANISM: Plasmodium falciparum

<400> SEQUENCE: 78

Tyr Val Ser Ser Lys Asp Lys Glu Asn Ile Ser Lys Glu Asn Glu
1               5                   10                  15

<210> SEQ ID NO 79
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base

```
<222> LOCATION: (18)..(18)
<223> OTHER INFORMATION: a, c, g, t, unknown or other

<400> SEQUENCE: 79
ggtgtgcatt cccaggtnca attggtrcar tcyg                               34

<210> SEQ ID NO 80
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gtccaagctt cgtacgttaa ctcacctgar gagacrgtga cc                      42

<210> SEQ ID NO 81
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ttgttattac tcgcggccca gccggtgcat tccgacatc                          39

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gtccaagctt cgtacgttaa cactcacgtt tgatctccag cctgg                   45

<210> SEQ ID NO 83
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ggtgtgcatt cccaggtgca attgcaggag tcsg                               34

<210> SEQ ID NO 84
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gtccaagctt cgtacgttaa cactcacgtt tgatctccac cc                      42

<210> SEQ ID NO 85
<211> LENGTH: 49
<212> TYPE: DNA
<213> ORGANISM: Artificial Sequence
<220> FEATURE:
<223> OTHER INFORMATION: Description of Artificial Sequence: Synthetic
```

-continued

```
    primer

<400> SEQUENCE: 85
gtccaagctt cgtacgttaa cttctactca cgtttgatyt ccaccttgg        49

<210> SEQ ID NO 86
<211> LENGTH: 24
<212> TYPE: PRT
<213> ORGANISM: Plasmodium falciparum

<400> SEQUENCE: 86

Glu Glu Asn Val Glu His Asp Ala Glu Glu Asn Val Glu His Asp Ala
1               5                   10                  15

Glu Glu Asn Val Glu Glu Asn Val
            20
```